United States Patent
Burris et al.

(10) Patent No.: US 11,746,097 B2
(45) Date of Patent: Sep. 5, 2023

(54) LXR INVERSE AGONISTS FOR TREATMENT OF CANCER

(71) Applicant: Saint Louis University, St. Louis, MO (US)

(72) Inventors: Thomas Burris, Columbia, MO (US); John K. Walker, St. Louis, MO (US); Colin Flaveny, St. Louis, MO (US); Arindam Chatterjee, St. Louis, MO (US)

(73) Assignee: Saint Louis University, Saint Louis, MO (US)

( * ) Notice: Subject to any disclaimer, the term of this patent is extended or adjusted under 35 U.S.C. 154(b) by 137 days.

(21) Appl. No.: 16/311,941

(22) PCT Filed: Jun. 23, 2017

(86) PCT No.: PCT/US2017/039116
§ 371 (c)(1),
(2) Date: Dec. 20, 2018

(87) PCT Pub. No.: WO2017/223514
PCT Pub. Date: Dec. 28, 2017

(65) Prior Publication Data
US 2020/0308135 A1 Oct. 1, 2020

Related U.S. Application Data

(60) Provisional application No. 62/354,507, filed on Jun. 24, 2016.

(51) Int. Cl.
| | | |
|---|---|---|
| C07D 401/04 | (2006.01) | |
| C07D 217/26 | (2006.01) | |
| C07D 401/12 | (2006.01) | |
| C07D 217/06 | (2006.01) | |
| C07D 417/04 | (2006.01) | |
| C07D 409/04 | (2006.01) | |
| C07D 215/38 | (2006.01) | |
| A61K 9/00 | (2006.01) | |

(52) U.S. Cl.
CPC ......... *C07D 401/04* (2013.01); *C07D 215/38* (2013.01); *C07D 217/06* (2013.01); *C07D 217/26* (2013.01); *C07D 401/12* (2013.01); *C07D 409/04* (2013.01); *C07D 417/04* (2013.01); *A61K 9/0019* (2013.01); *A61K 9/0053* (2013.01)

(58) Field of Classification Search
CPC .. C07D 401/04; C07D 215/38; C07D 217/06; C07D 217/26; C07D 401/12; C07D 409/04; C07D 417/04; A61K 9/0019; A61K 9/0053
USPC ....................................................... 514/256
See application file for complete search history.

(56) References Cited

U.S. PATENT DOCUMENTS

| | | |
|---|---|---|
| 2006/0270718 A1 | 11/2006 | Jiao et al. |
| 2007/0099960 A1 | 5/2007 | Lebreton et al. |
| 2009/0088459 A1 | 4/2009 | Dehmlow et al. |
| 2013/0197049 A1* | 8/2013 | Li .................. A61K 45/06 514/400 |

FOREIGN PATENT DOCUMENTS

| | | | |
|---|---|---|---|
| JP | 3850920 B2 * | 11/2006 | .......... C07D 217/14 |
| WO | WO 00/54759 | 9/2000 | |

OTHER PUBLICATIONS

Boss et al., Structure-Activity Relationship, Biological, and Pharmacological Characterization of the Proline Sulfonamide ACT-462206: a Potent, Brain-Penetrant Dual Orexin 1/Orexin 2 Receptor Antagonist, 2014, ChemMedChem, 9, 2486-2496 (Year: 2014).*
Andreu et al., Synthesis of new 8-arylisoquinoline derivatives by application of palladium-catalyzed Suzuki cross-coupling reactions, 2005, Tetrahedron, 61, 8282-8287 (Year: 2005).*
Nammalwar et al., Friedel-Crafts cyclization of tertiary alcohols using bismuth(III)triflate, 2013, Tetrahedron Letters, 54, 4330-4332 (Year: 2013).*
English translation of JP 3850920 B2 (Year: 2022).*
Chuu et al. "Antiproliferative effect of LXR agonists T0901317 and 22 (R)-hydroxycholesterol on multiple human cancer cell lines." *Anticancer Research* 30.9 (2010): 3643-3648.
International Preliminary Report on Patentability issued in International Application No. PCT/US2017/039116, dated Jan. 3, 2019.
International Search Report and Written Opinion issued in International Application No. PCT/US2017/039116, dated Sep. 13, 2017.
Jamroz-Wisniewska et al. "Liver X receptors (LXRs). Part II: Non-lipid effects, role in pathology, and therapeutic implications. Liver X receptors (LXR). Part II: Non-lipid-related activities, role in pathology and therapeutic implications." *Hig Med Progress Adv. (Online)* 61 (2007): 760-785.
Raccosta et al. "The oxysterol-CXCR2 axis plays a key role in the recruitment of tumor-promoting neutrophils." *Journal of Experimental Medicine* 210.9 (2013): 1711-1728.
Rough et al. "Anti-proliferative effect of LXR agonist T0901317 in ovarian carcinoma cells." *Journal of Ovarian Research* 3.1 (2010): 13.
Russo, Vincenzo. "Metabolism, LXR/LXR ligands, and tumor immune escape." *Journal of Leukocyte Biology* 90.4 (2011): 673-679.
Villablanca et al. "Tumor-mediated liver X receptor-α activation inhibits CC chemokine receptor-7 expression on dendritic cells and dampens antitumor responses." *Nature Medicine* 16.1 (2010): 98.

* cited by examiner (Continued)

*Primary Examiner* — Kristin A Vajda
(74) *Attorney, Agent, or Firm* — Parker Highlander PLLC

(57) ABSTRACT

In some aspects, the present disclosure provides compounds of the formula: (I) or (II) wherein the variables are as defined herein. In some embodiments, these compounds may be used to treat cancer or other hyperproliferative diseases, as well as atherosclerosis and coronary artery disease.

15 Claims, 2 Drawing Sheets

LXR INVERSE AGONISTS FOR TREATMENT OF CANCER

This application is a national phase application under 35 U.S.C. § 371 of International Application No. PCT/US2017/039116, filed Jun. 23, 2017, which claims benefit of priority to U.S. Provisional Application Ser. No. 62/354,507, filed Jun. 24, 2016, the entire contents of which are hereby incorporated by reference.

BACKGROUND

1. Field

The present disclosure relates generally to the field of oncology and chemotherapeutics. More particularly, it concerns new inverse agonists of Liver X Receptors (LXR) and their use in treating cancer or atherosclerosis.

2. Description of Related Art

Metabolism in cancer cells is primarily glycolytic even when oxygen is abundant (Warburg et al., 1927). Aerobic glycolysis or the Warburg effect is well characterized and has been shown to be driven by mitochondrial defects, oncogenic stimuli, hypoxia, and aberrantly enhanced expression of glycolytic enzymes (DeBerardinis et al., 2008; Warburg et al., 1927; Yeung et al., 2008). In particular, elevated glycolytic gene expression is pervasive in cancers of the breast, colon, prostate, and lung. Oncogenes such as mTOR, c-MYC, and hypoxia-inducible factor 1 (HIF-1) promote glycolytic activity by upregulating expression of glycolytic enzymes including phosphofructokinase 1 (PFK1), hexokinases, and pyruvate dehydrogenase kinase-3 (Dang et al., 1997; Jung et al., 2011; Koshiji and Huang, 2004; Lu et al., 2008). In addition, expression of glycolysis-stimulating genes such as PFK1 and phosophofructokinase-2 (PFK2) are strongly associated with highly aggressive and drug-resistant tumor types (DeBerardinis et al., 2008; Phan et al., 2014). Conversely, the tumor suppressor P53 has been shown to block cancer cell growth by suppressing glucose consumption, preventing the downregulation of mitochondrial aerobic respiration, inhibiting NADPH production, and disrupting pentose phosphate synthesis (Yeung et al., 2008). Therefore, the Warburg effect is a central component of the metabolic reprogramming involved in cancer etiology.

Glycolysis is less energy efficient compared to aerobic respiration because it produces significantly fewer molecules of ATP. However, by providing a surplus of metabolic substrates for analplerosis that would be unavailable through normal aerobic respiration, the Warburg effect confers a selective survival advantage to cancer cells. Substrates produced are funneled into other metabolic pathways such as de novo lipid synthesis (lipogenesis), nucleotide production and amino acid synthesis, all of which are indispensable for rapid cancer cell growth. Lactate, produced in abundance in tumors, is instrumental in altering the intracellular redox balance, which promotes cancer cell invasiveness (Bonuccelli et al., 2010; Martinez-Outschoorn et al., 2011; Vander Heiden et al., 2009). Therefore, the Warburg effect functions as the metabolic foundation of oncogenic growth, tumor progression, and tumor resistance to treatment. Despite displaying elevated glycolytic gene expression, cancer cells within the tumor microenvironment can have distinct metabolic profiles depending on pH and oxygen availability (Dang, 2007; Fritz et al., 2010; Huang et al., 2012; Vander Heiden et al., 2009; Yeung et al., 2008). This metabolic plasticity allows cancer cells to evade cell death. Despite the variety of "druggable" targets identified, most glycolysis inhibitors show substantial toxicity in normal tissues and limited therapeutic applications in select cancer types (Pelicano et al., 2006).

The surplus glycolysis metabolites produced by the Warburg effect are integrated into lipogenesis and other metabolic pathways in tumor cells. Glycolysis products are used to synthesize short-, medium-, and long-chain fatty acids that are fundamental building blocks for cell membranes and organelles. Typically, cancer cells show elevated expression of lipogenesis enzymes and endogenous production of lipids, whereas normal cells obtain lipids primarily from exogenous sources (Vander Heiden et al., 2009). Like glycolysis, lipogenic enzyme expression is enhanced in tumors via oncogenic signaling. Although both pathways are linked, compared to tumor glycolysis, lipogenesis is not regulated by changes within the tumor microenvironment such as pH and the availability of oxygen (Blancher and Harris, 1998). Lipids are synthesized by enzymes such as fatty acid synthase (FASN), stearoyl-CoA desaturase (SCD1), and acetyl-CoA carboxylase-1 (ACC1) acting downstream of glycolysis. Lipogenesis also facilitates immune system evasion and intercellular signaling that promote tumor growth (Phan et al., 2014). Lipid metabolites also provide valuable reducing power within the low nutrient and highly oxidative microenvironment of tumors (Carracedo et al., 2013; Zaytseva et al., 2012). Accordingly, lipogenic gene expression directly correlates with cancer aggressiveness, staging, and drug resistance (Notarmcola et al., 2006, 2012; Ogino et al., 2009; Zaytseva et al., 2012). Increased expression of FASN, SCD1, and ACC1 as well as the sterol-regulatory element binding protein-1c (SREBP1c), a transcription factor that regulates lipogenic gene expression, is associated with numerous forms of cancer (Furuta et al., 2010; Mason et al., 2012). Lipogenesis inhibitors that block FASN, ACC1, SCD1, and SREBP1c activity have been shown to reduce proliferation and induce apoptosis in cancer cells (Chajes et al., 2006; Mason et al., 2012; Notarmcola et al., 2006, 2012; Scaglia et al., 2009). However, clinically viable therapies that effectively block lipogenesis in vivo have not been forthcoming due to adverse side effects such as anorexia and severe weight loss (Clegg et al., 2002; Tu et al., 2005).

SUMMARY

In some aspects, the present disclosure provides compounds which may be used as liver X receptor inverse agonists. In some embodiments, the compounds are further defined as:

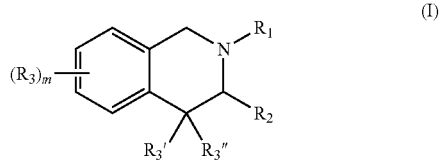

(I)

wherein:
  $R_1$ is —C(O)$R_4$, —S(O)$_2R_4$, —S(O)$R_4$, or —CH$_2R_4$;
    wherein:
      $R_4$ is aryl$_{(C \leq 12)}$, heteroaryl$_{(C \leq 12)}$, or a substituted version of either of these groups;

$R_2$ is hydrogen, $-(CH_2)_nOR_5$, $-(CH_2)_nC(O)OR_5$, $-(CH_2)_nC(O)NR_5R_6$, or $-(CH_2)_nNR_5R_6$; wherein:
  $R_5$ and $R_6$ are each independently hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these five groups;
  n is 0, 1, 2, or 3;
$R_3$ is hydrogen, halo, aryl$_{(C\leq12)}$, substituted aryl$_{(C\leq12)}$, heteroaryl$_{(C\leq12)}$, or substituted heteroaryl$_{(C\leq12)}$;
$R_3'$ and $R_3''$ are each independently hydrogen, alkyl$_{(C\leq8)}$, or substituted alkyl$_{(C\leq8)}$; and
m is 1, 2, 3, or 4; or
a compound of the formula:

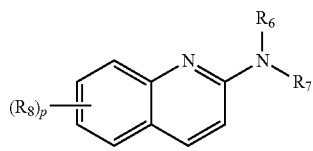
(II)

wherein:
  $R_6$ is $-C(O)R_9$, $-S(O)_2R_9$, $-S(O)R_9$, or $-CH_2R_9$; wherein:
    $R_9$ is alkyl$_{(C\leq12)}$, aryl$_{(C\leq12)}$, heteroaryl$_{(C\leq12)}$, or a substituted version of these groups;
  $R_7$ is hydrogen, alkyl$_{(C\leq12)}$, or substituted alkyl$_{(C\leq12)}$;
  $R_8$ is hydrogen, halo, aryl$_{(C\leq12)}$, substituted aryl$_{(C\leq12)}$, heteroaryl$_{(C\leq12)}$, or substituted heteroaryl$_{(C\leq12)}$; and
  p is 1, 2, 3, or 4;
or a pharmaceutically acceptable salt thereof.

In some embodiments, the present disclosure provides compounds of the formula:

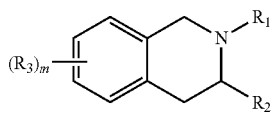
(I)

wherein:
  $R_1$ is $-C(O)R_4$, $-S(O)_2R_4$, $-S(O)R_4$, or $-CH_2R_4$; wherein:
    $R_4$ is aryl$_{(C\leq12)}$, heteroaryl$_{(C\leq12)}$, or a substituted version of either of these groups;
  $R_2$ is hydrogen, $-(CH_2)_nOR_5$, $-(CH_2)_nC(O)OR_5$, or $-(CH_2)_nNR_5R_6$; wherein:
    $R_5$ and $R_6$ are each independently hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these five groups;
  $R_3$ is hydrogen, halo, aryl$_{(C\leq12)}$, substituted aryl$_{(C\leq12)}$, heteroaryl$_{(C\leq12)}$, or substituted heteroaryl$_{(C\leq12)}$; and
  m is 1, 2, 3, or 4; or
a compound of the formula:

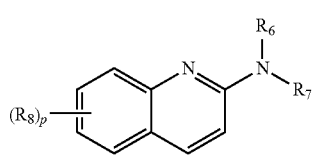
(II)

wherein:
  $R_6$ is $-C(O)R_9$, $-S(O)_2R_9$, $-S(O)R_9$, or $-CH_2R_9$; wherein:
    $R_9$ is aryl$_{(C\leq12)}$, heteroaryl$_{(C\leq12)}$, or a substituted version of either of these groups;
  $R_7$ is hydrogen, alkyl$_{(C\leq12)}$, or substituted alkyl$_{(C\leq12)}$;
  $R_8$ is hydrogen, halo, aryl$_{(C\leq12)}$, substituted aryl$_{(C\leq12)}$, heteroaryl$_{(C\leq12)}$, or substituted heteroaryl$_{(C\leq12)}$; and
  p is 1, 2, 3, or 4;
or a pharmaceutically acceptable salt thereof.

The compound may be further defined as:

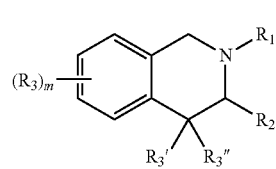
(I)

wherein:
  $R_1$ is $-C(O)R_4$, $-S(O)_2R_4$, $-S(O)R_4$, or $-CH_2R_4$; wherein:
    $R_4$ is aryl$_{(C\leq12)}$, heteroaryl$_{(C\leq12)}$, or a substituted version of either of these groups;
  $R_2$ is hydrogen, $-(CH_2)_nOR_5$, $-(CH_2)_nC(O)OR_5$, $-(CH_2)_nC(O)NR_5R_6$, or $-(CH_2)_nNR_5R_6$; wherein:
    $R_5$ and $R_6$ are each independently hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these five groups;
    n is 0, 1, 2, or 3;
  $R_3$ is hydrogen, halo, aryl$_{(C\leq12)}$, substituted aryl$_{(C\leq12)}$, heteroaryl$_{(C\leq12)}$, or substituted heteroaryl$_{(C\leq12)}$;
  $R_3'$ and $R_3''$ are each independently hydrogen, alkyl$_{(C\leq8)}$, or substituted alkyl$_{(C\leq8)}$; and
  m is 1, 2, 3, or 4;
or a pharmaceutically acceptable salt thereof.

The compound may be further defined as:

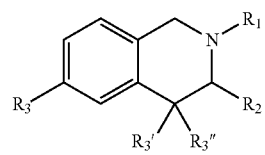
(IV)

wherein:
  $R_1$ is $-C(O)R_4$, $-S(O)_2R_4$, $-S(O)R_4$, or $-CH_2R_4$; wherein:
    $R_4$ is aryl$_{(C\leq12)}$, heteroaryl$_{(C\leq12)}$, or a substituted version of either of these groups;
  $R_2$ is hydrogen, $-(CH_2)_nOR_5$, $-(CH_2)_nC(O)OR_5$, $-(CH_2)_nC(O)NR_5R_6$, or $-(CH_2)_nNR_5R_6$; wherein:
    $R_5$ and $R_6$ are each independently hydrogen or alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these five groups; and
    n is 0, 1, 2, or 3;
  $R_3$ is hydrogen, halo, aryl$_{(C\leq12)}$, substituted aryl$_{(C\leq12)}$, heteroaryl$_{(C\leq12)}$, or substituted heteroaryl$_{(C\leq12)}$; and
  $R_3'$ and $R_3''$ are each independently hydrogen, alkyl$_{(C\leq8)}$, or substituted alkyl$_{(C\leq8)}$;
or a pharmaceutically acceptable salt thereof.

The compound may be further defined as:

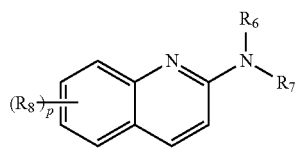

wherein:
R$_6$ is —C(O)R$_9$, —S(O)$_2$R$_9$, —S(O)R$_9$, or —CH$_2$R$_9$;
  wherein:
    R$_9$ is alkyl$_{(C≤12)}$, aryl$_{(C≤12)}$, heteroaryl$_{(C≤12)}$, or a substituted version of these groups;
R$_7$ is hydrogen, alkyl$_{(C≤12)}$, or substituted alkyl$_{(C≤12)}$;
R$_8$ is hydrogen, halo, aryl$_{(C≤12)}$, substituted aryl$_{(C≤12)}$, heteroaryl$_{(C≤12)}$, or substituted heteroaryl$_{(C≤12)}$; and
p is 1, 2, 3, or 4;
or a pharmaceutically acceptable salt thereof.

The compound may be further defined as:

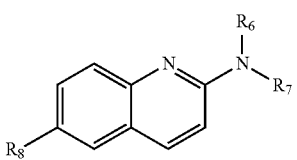

wherein:
R$_6$ is —C(O)R$_9$, —S(O)$_2$R$_9$, —S(O)R$_9$, or —CH$_2$R$_9$;
  wherein:
    R$_9$ is alkyl$_{(C≤12)}$, aryl$_{(C≤12)}$, heteroaryl$_{(C≤12)}$, or a substituted version of these groups;
R$_7$ is hydrogen, alkyl$_{(C≤12)}$, or substituted alkyl$_{(C≤12)}$; and
R$_8$ is hydrogen, halo, aryl$_{(C≤12)}$, substituted aryl$_{(C≤12)}$, heteroaryl$_{(C≤12)}$, or substituted heteroaryl$_{(C≤12)}$;
or a pharmaceutically acceptable salt thereof.

The compound above may have R$_1$ as —S(O)$_2$R$_4$, and optionally have R$_4$ as aryl$_{(C≤12)}$ or substituted aryl$_{(C≤12)}$, including R$_4$ as 2,4,6-trimethylphenyl, 3,4-dimethylphenyl, 3-trifluoromethylphenyl, 4-trifluoromethylphenyl, 3-chlorophenyl, and 4-chlorophenyl. In some embodiments, R$_4$ is 2,4,6-trimethylphenyl. R$_4$ may also be heteroaryl$_{(C≤12)}$ or substituted heteroaryl$_{(C≤12)}$, such as N-methylimidazolyl.

The compound may R$_2$ as hydrogen, or as —(CH$_2$)$_n$C(O)NR$_5$R$_6$, such as n is 0 or 1, wherein R$_5$ is hydrogen, or alkyl$_{(C≤6)}$ or substituted alkyl$_{(C≤6)}$, and wherein R$_6$ is aralkyl$_{(C≤12)}$ or substituted aralkyl$_{(C≤12)}$, in particular benzyl or 2-phenylethyl or 3-cyanobenzyl or 2-(3-cyanophenyl)ethyl. Alternatively, R$_6$ may be aryl$_{(C≤12)}$ or substituted aryl$_{(C≤12)}$ such as phenyl. In other embodiments, R$_6$ is heteroaralkyl$_{(C≤12)}$ or substituted heteroaralkyl$_{(C≤12)}$ such as 3-N-pyrazolylbenzyl, 4-N-pyrazolylbenzyl, or 2-(4-N-pyrazolylphenyl)-ethyl. In other embodiments, R$_2$ is —C(O)OR$_5$ wherein R$_5$ is hydrogen.

The compound may have R$_3$ as hydrogen, halo, or aryl$_{(C≤12)}$ or substituted aryl$_{(C≤12)}$, in particular 3-(methylsulfinyl)phenyl or 3-methoxyphenyl, and R$_6$ may independently be —C(O)R$_9$, such as aryl$_{(C≤12)}$ or substituted aryl$_{(C≤12)}$, including substituted aryl$_{(C≤12)}$ such as 3-(methylsulfonyl)phenyl, 4-(methylsulfonyl)phenyl, 2-cyanophenyl, 3-cyanophenyl, 4-cyanophenyl, 2-trifluoromethylphenyl, 3-trifluoromethylphenyl, 4-trifluoromethylphenyl, 2-fluorophenyl, 3-fluorophenyl, 4-fluorophenyl, 2-methoxyphenyl, 3-methoxyphenyl, 4-methoxyphenyl, 3-aminophenyl, 3-aminomethylphenyl, 4-aminomethylphenyl, 3-N-t-butoxycarbonylaminomethylphenyl or 3-N-t-butoxycarbonylaminophenyl. Alternatively, R$_3$ is heteroaryl$_{(C≤12)}$ or substituted heteroaryl$_{(C≤12)}$ including heteroaryl$_{(C≤12)}$ such as 2-pyridinyl, 3-pyridinyl, 4-pyridinyl, 2-thiophenyl, 3-thiophenyl, 6-benzothiazolyl, or 5-pyrimidinyl.

In some embodiments, R$_3$' is hydrogen. In other embodiments, R$_3$' is alkyl$_{(C≤8)}$ such as methyl. In some embodiments, R$_3$" is hydrogen. In other embodiments, R$_3$" is alkyl$_{(C≤8)}$ such as methyl.

The compound may have R$_6$ is —S(O)$_2$R$_9$, wherein R$_9$ is aryl$_{(C≤12)}$ or substituted aryl$_{(C≤12)}$ such as phenyl, 2,4,6-trimethylphenyl, 3,4-dimethylphenyl, or 3-chlorophenyl. In some embodiments, R$_9$ is 2,4,6-trimethylphenyl. In other embodiments, R$_9$ is alkyl$_{(C≤12)}$ or substituted alkyl$_{(C≤12)}$. Alternatively, the compound may have R$_6$ is —C(O)R$_9$. In some embodiments, R$_9$ is alkyl$_{(C≤12)}$ or substituted alkyl$_{(C≤12)}$. In other embodiments, R$_9$ is aryl$_{(C≤12)}$ or substituted aryl$_{(C≤12)}$ such as phenyl, 2,4,6-trimethylphenyl, 3,4-dimethylphenyl, or 3-chlorophenyl. In other embodiments, R$_9$ is heteroaryl$_{(C≤12)}$ or substituted heteroaryl$_{(C≤12)}$.

The compound may have R$_7$ is hydrogen, alkyl$_{(C≤6)}$ or substituted alkyl$_{(C≤6)}$. R$_8$ may independently be hydrogen, such halo or bromo. Alternatively, R$_8$ may independently be aryl$_{(C≤12)}$ or substituted aryl$_{(C≤12)}$, such as phenyl, 3-methylsulfonylphenyl, 4-methylsulfonylphenyl, 3-methoxyphenyl, 4-methoxyphenyl, 3-trifluoromethylphenyl, 4-trifluoromethylphenyl, 3-cyanophenyl, 4-cyanophenyl, 3-formylphenyl, 4-formylphenyl, 3-acetylphenyl, 4-acetylphenyl, 3-carbamoylphenyl, 4-carbamoylphenyl, or 3-aminomethylphenyl.

The compound may have p as 1 or 2, and/or m as 1 or 2.

In some embodiments, the compound is further defined as:

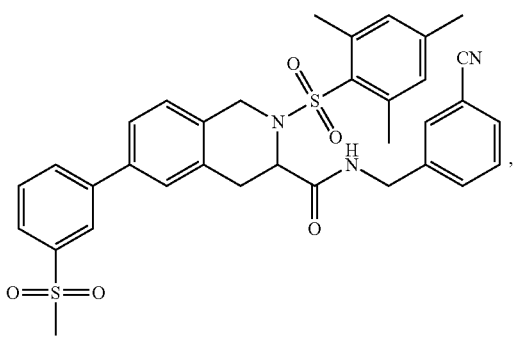

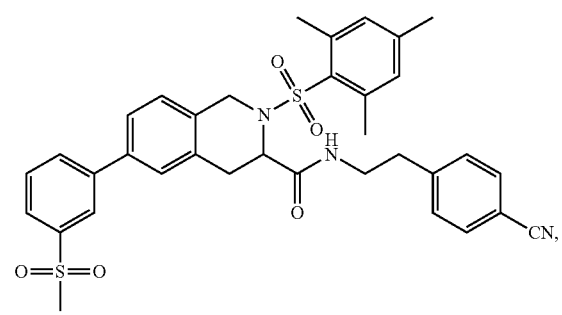

-continued
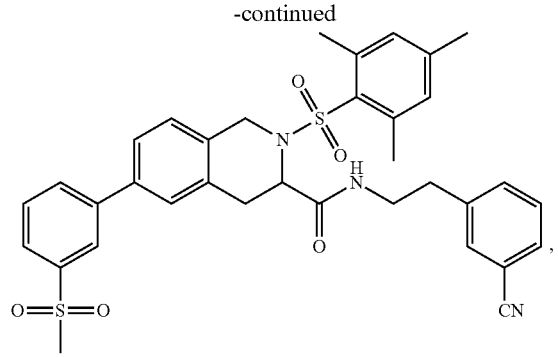
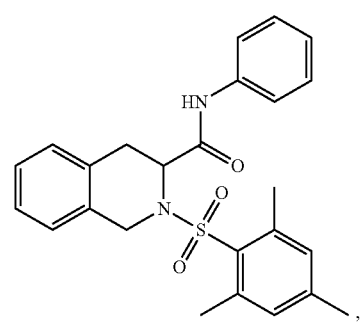
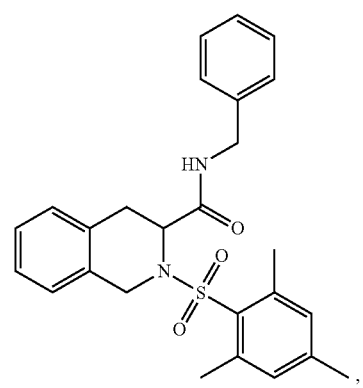
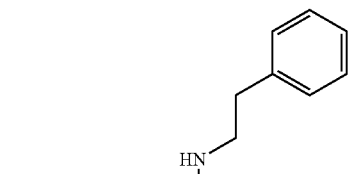
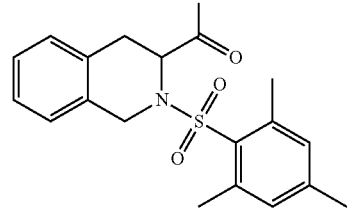
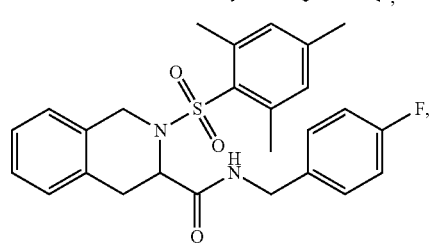
-continued
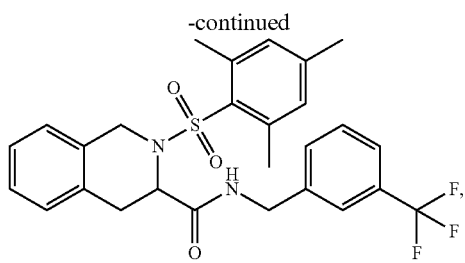
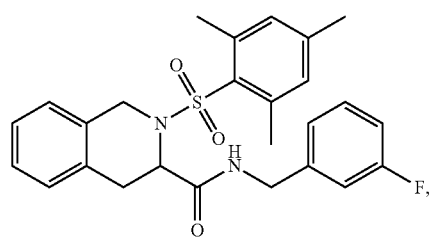
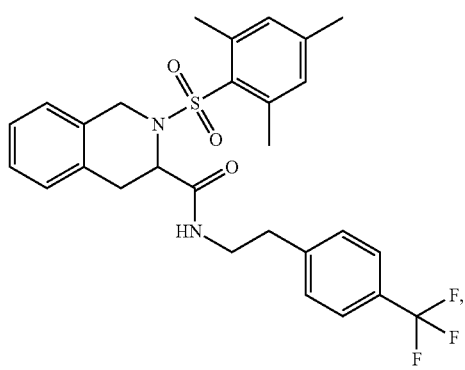
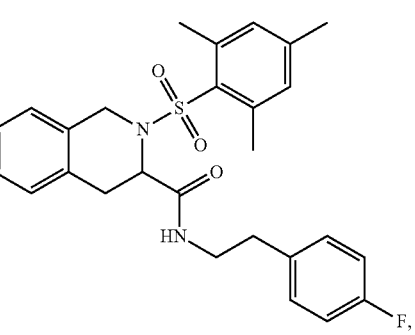
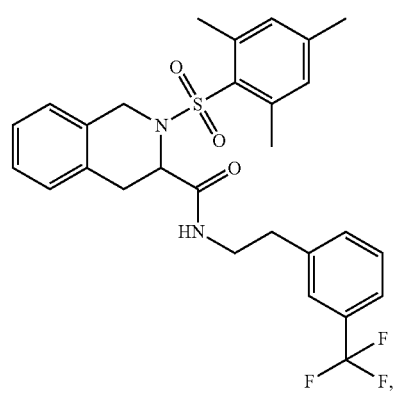

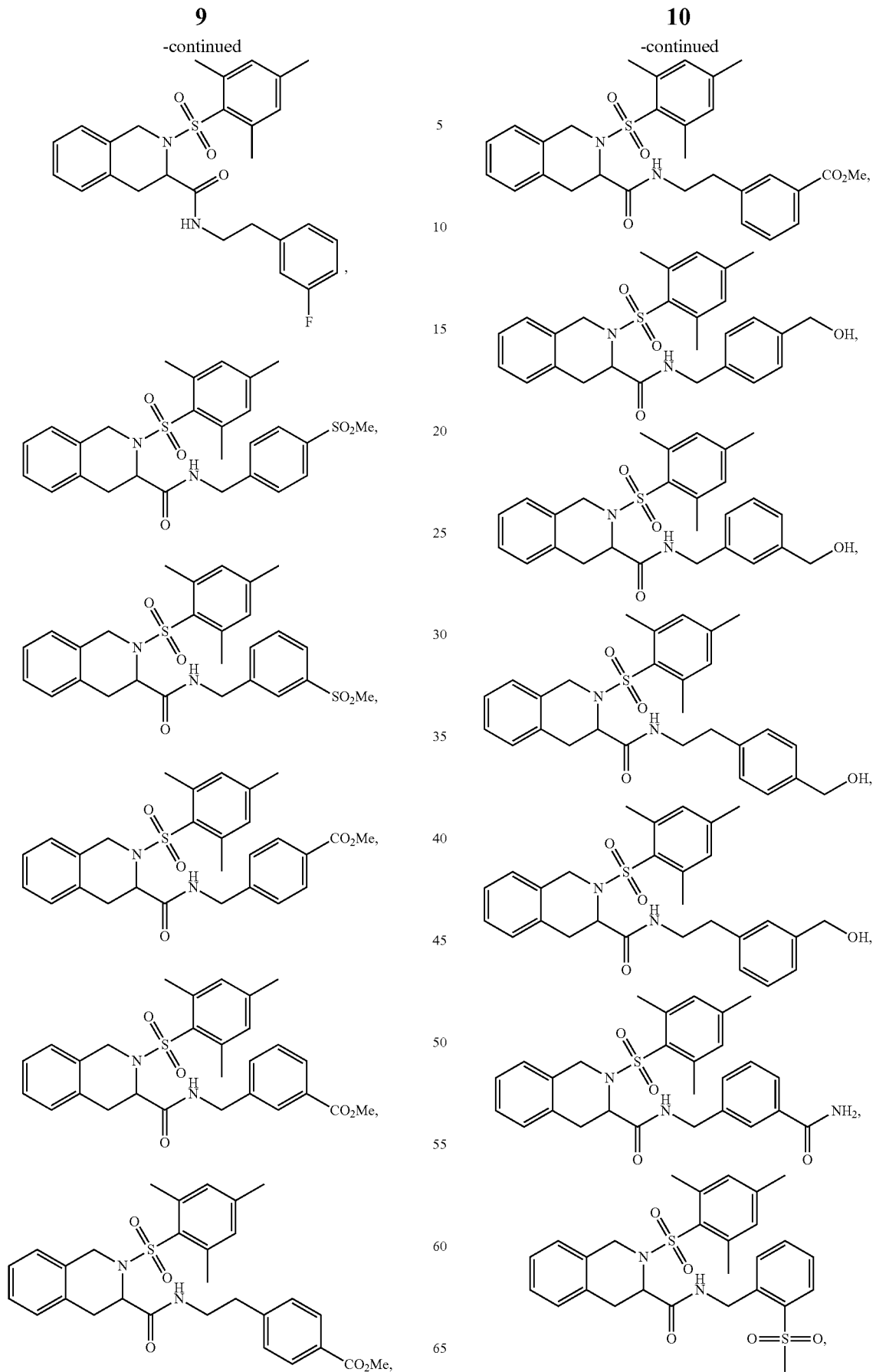

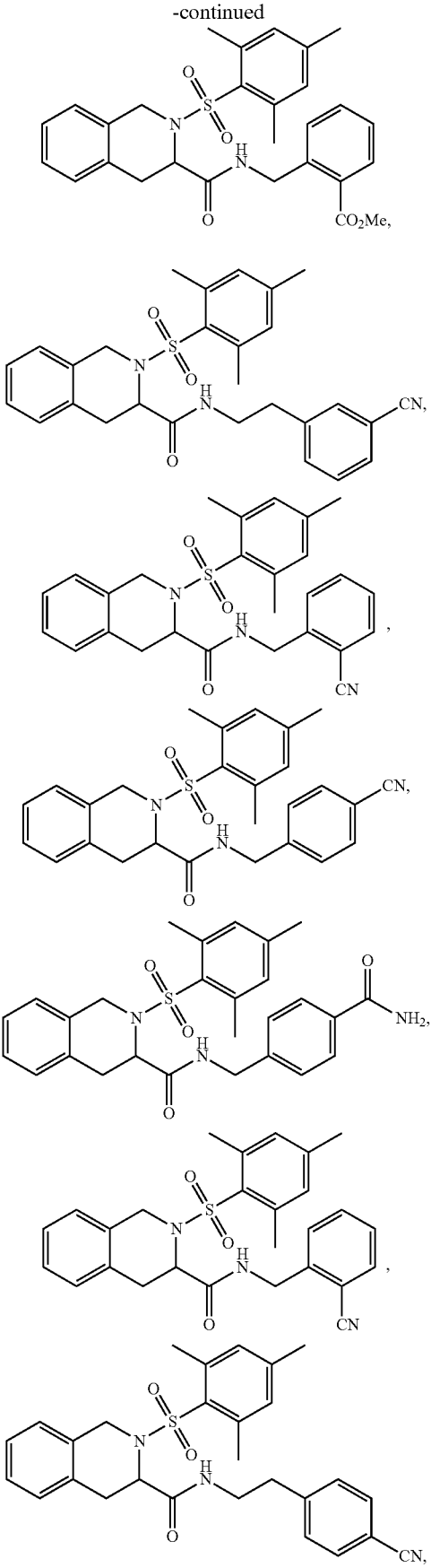
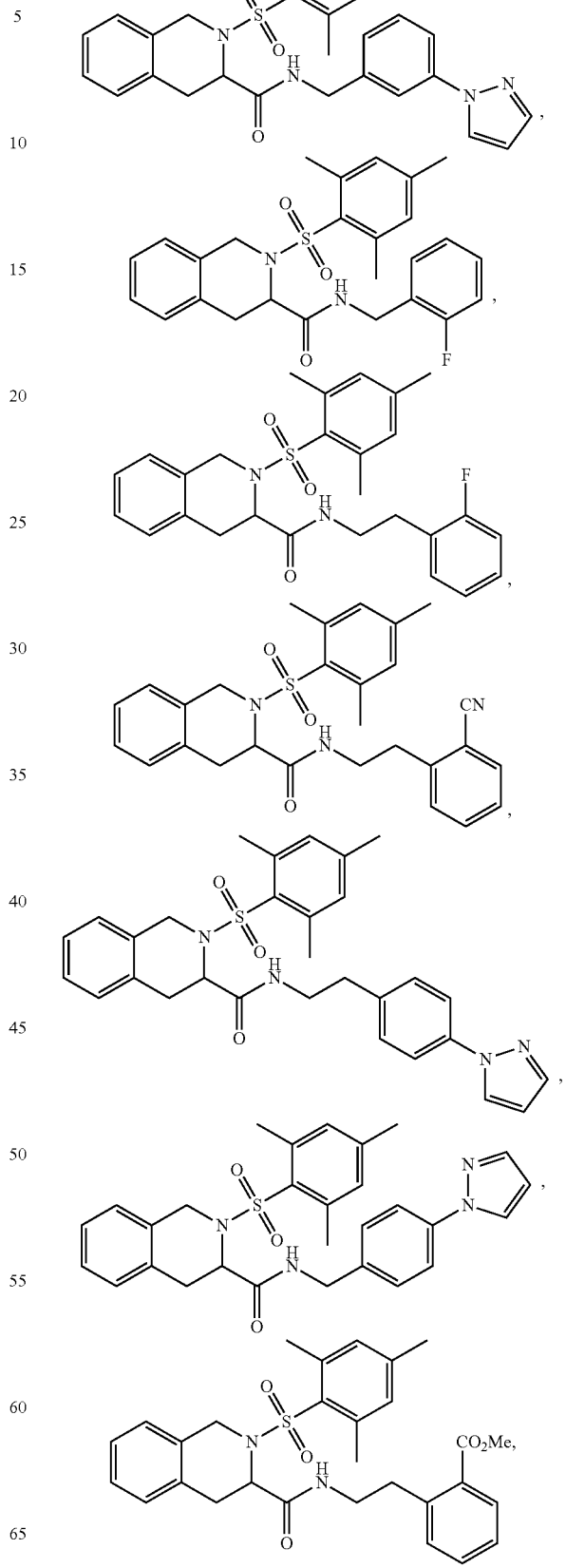

-continued
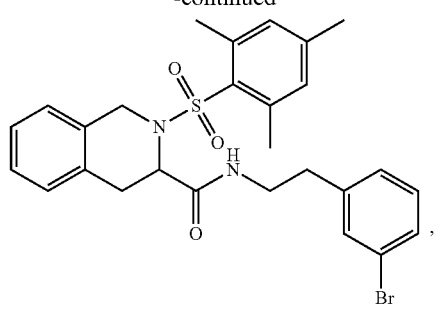
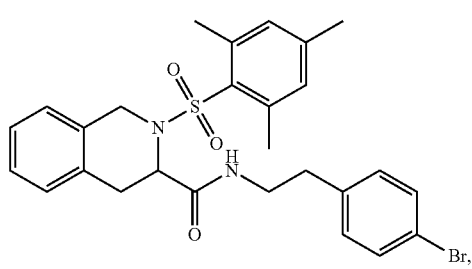
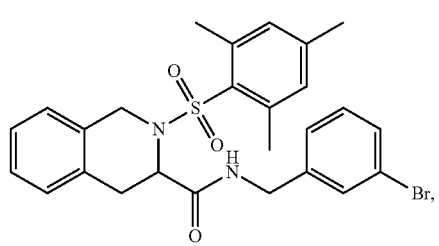
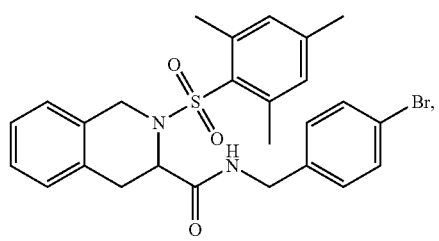
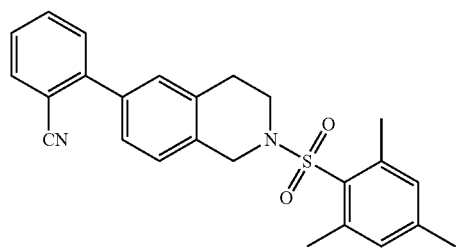
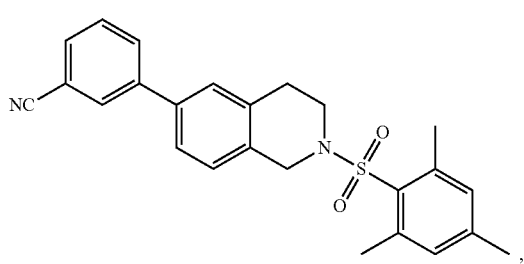
-continued
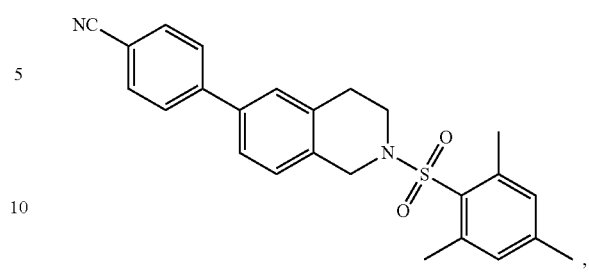
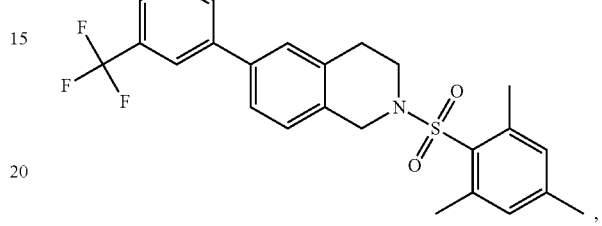
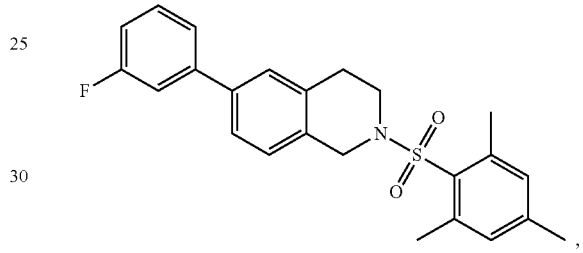
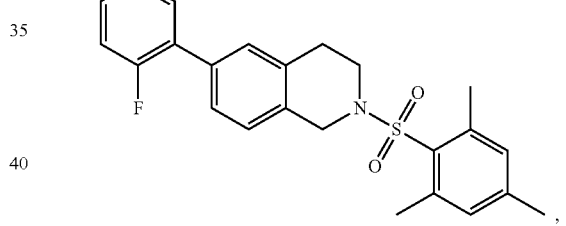
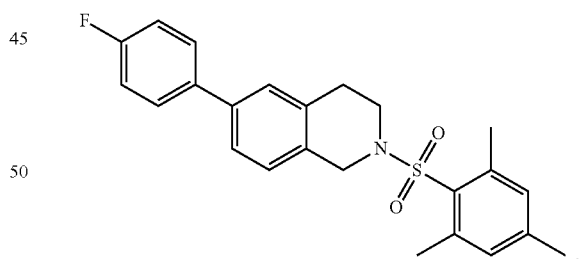
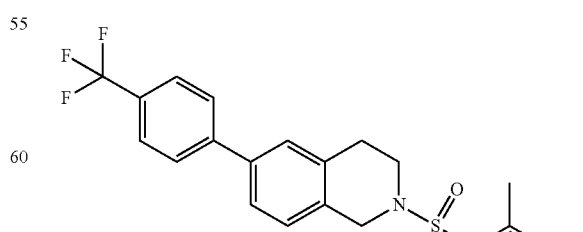

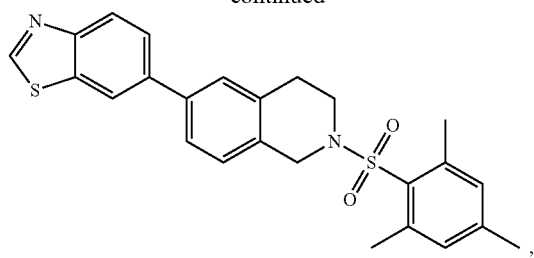
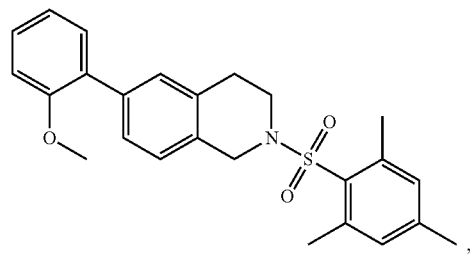
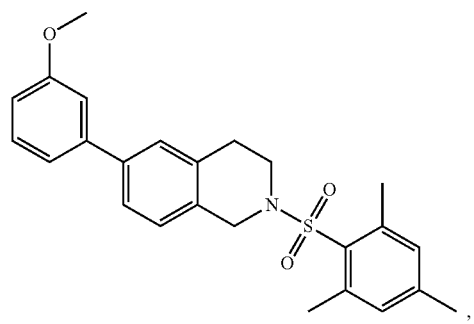
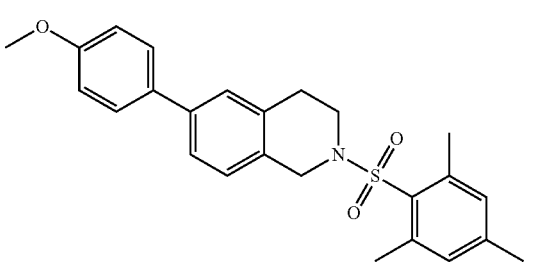
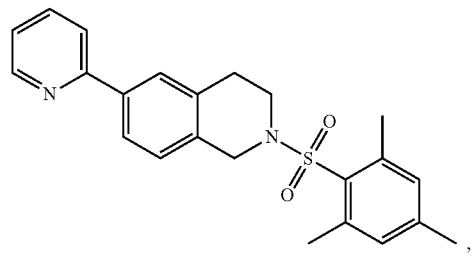
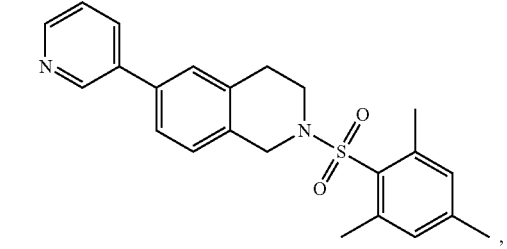
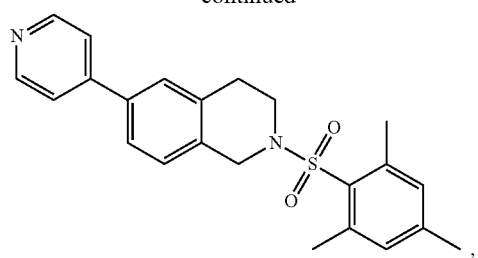
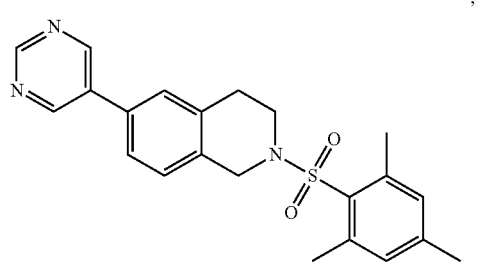
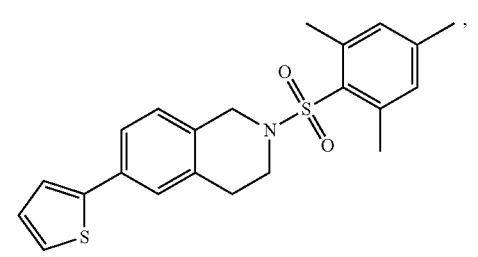
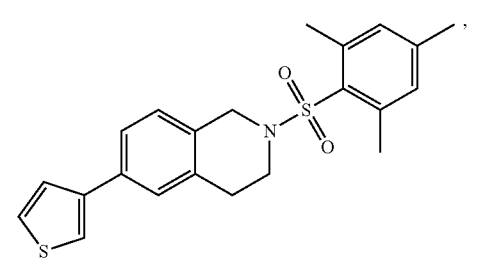
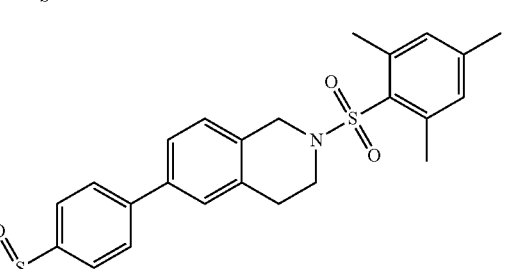
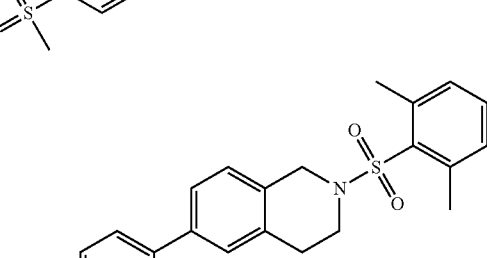

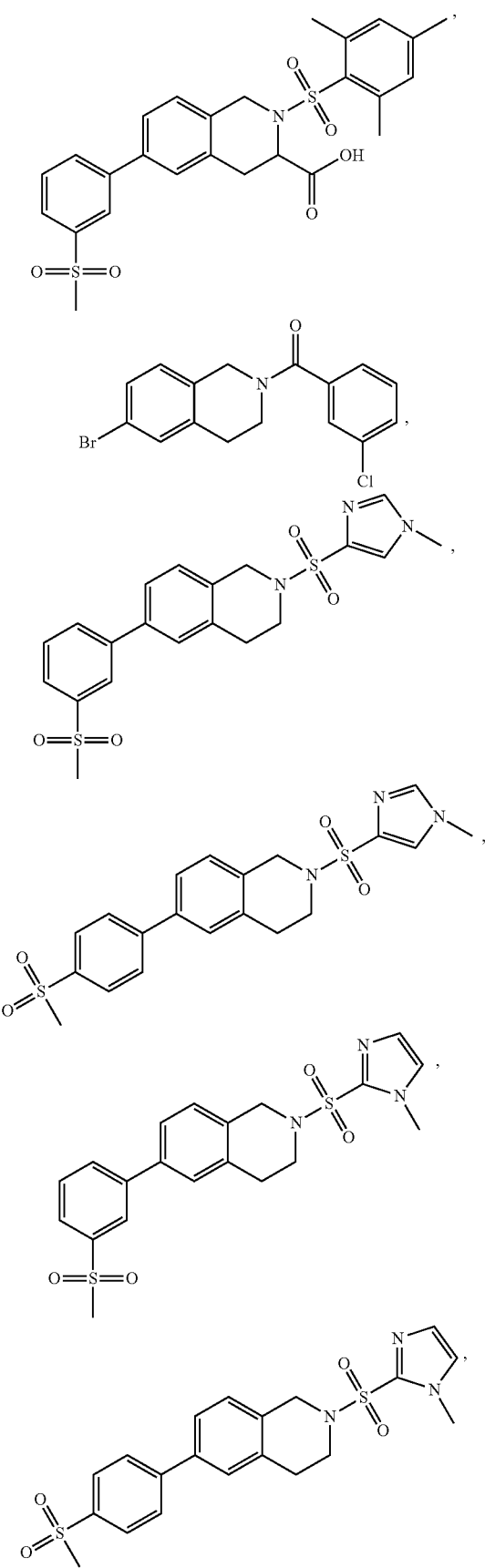
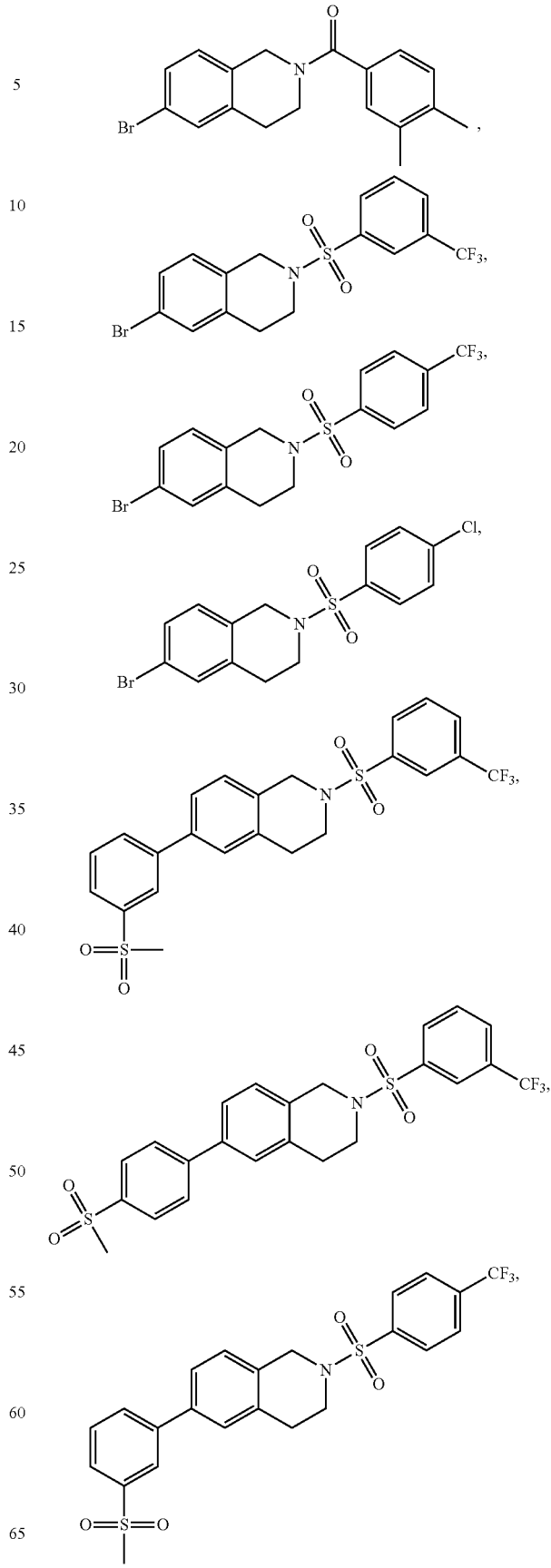

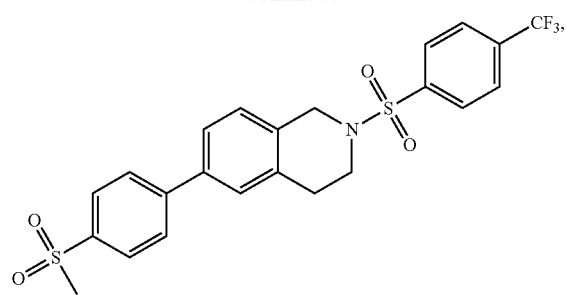
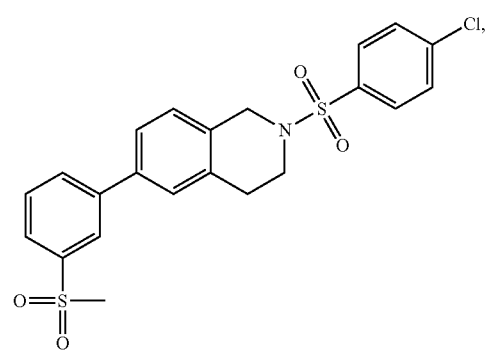
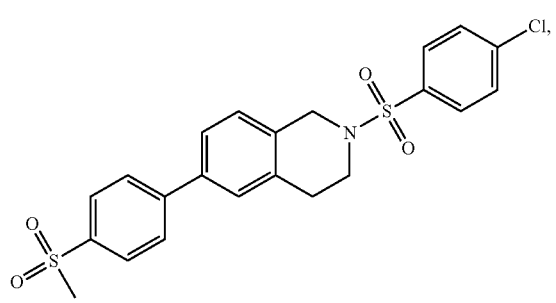
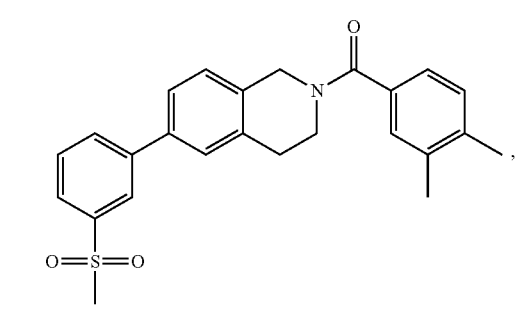
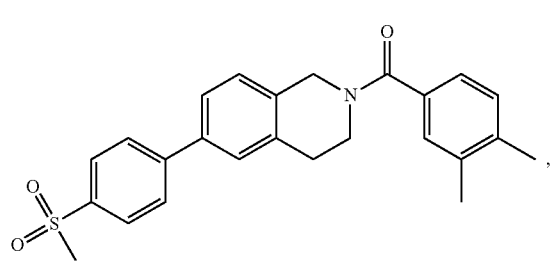
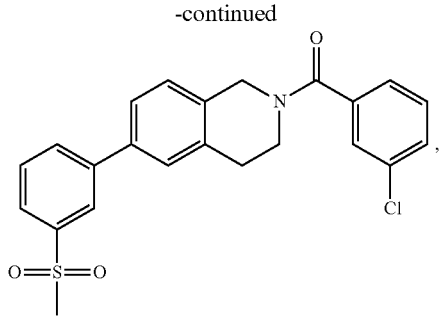
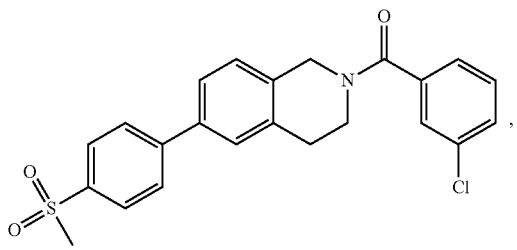
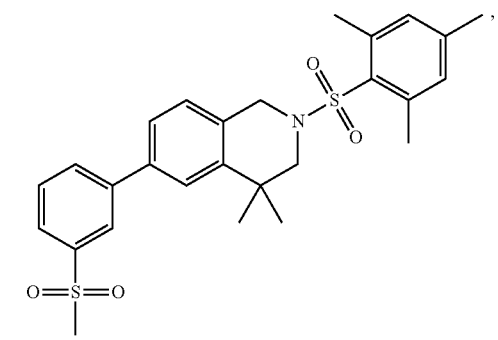
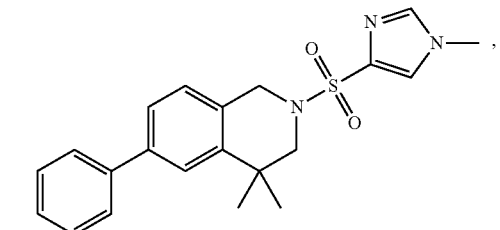
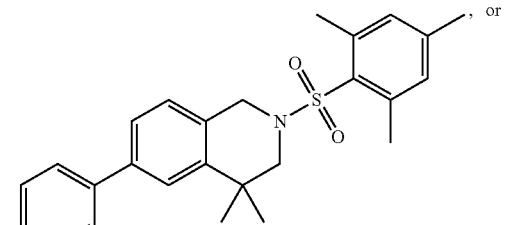
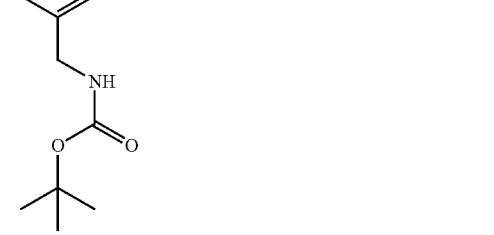

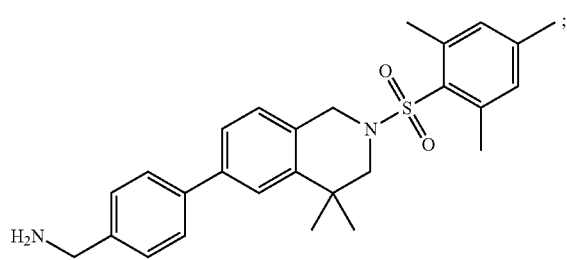
or a pharmaceutically acceptable salt thereof. In other embodiments, the compound is further defined as:
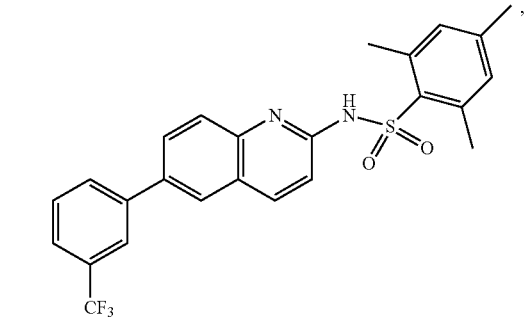
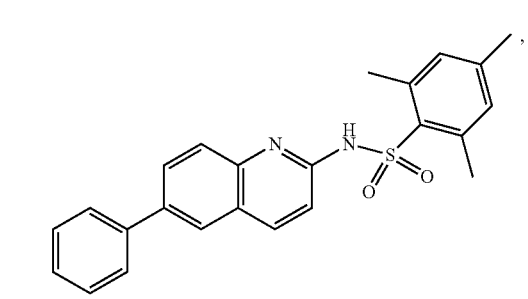
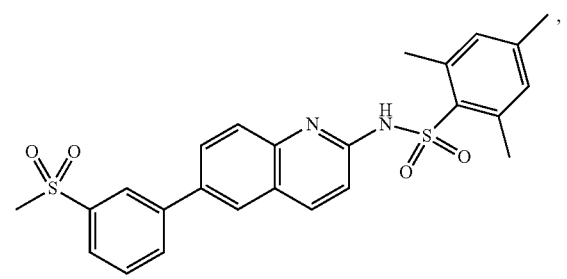
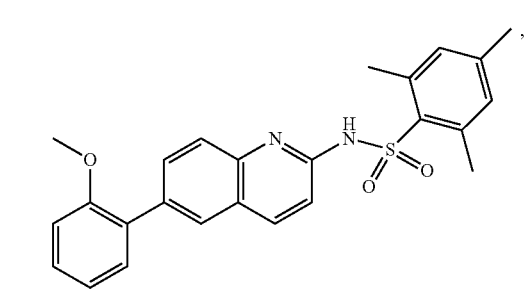
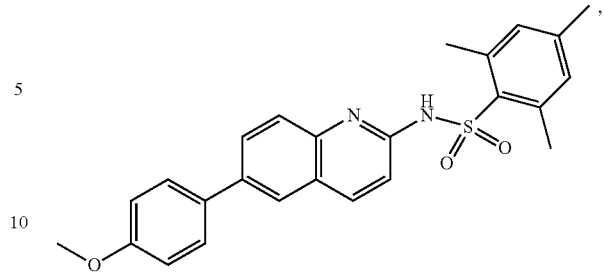
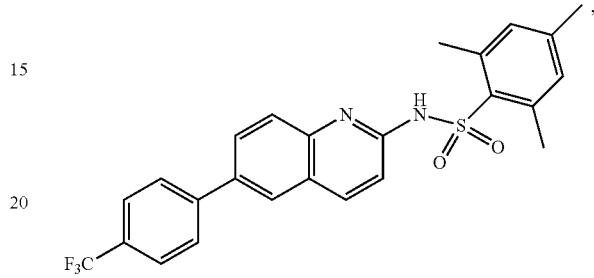
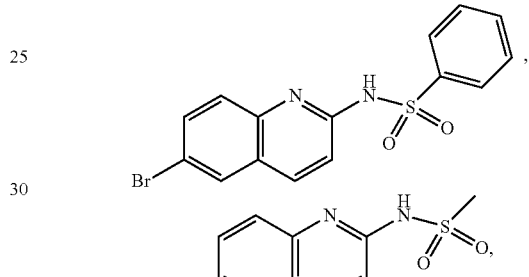
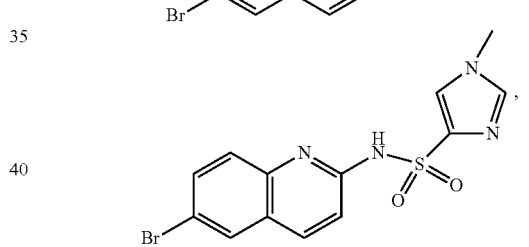
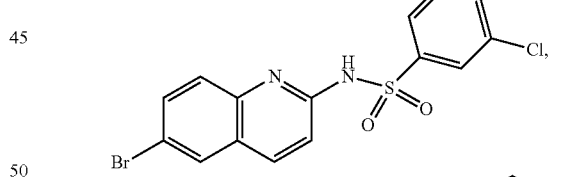
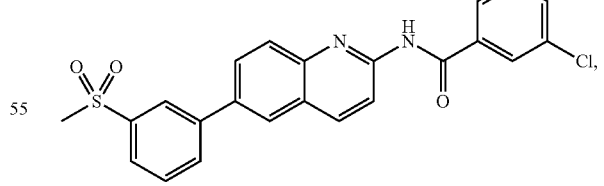
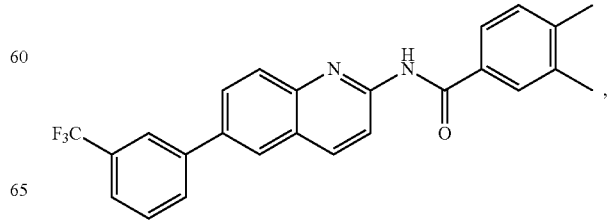

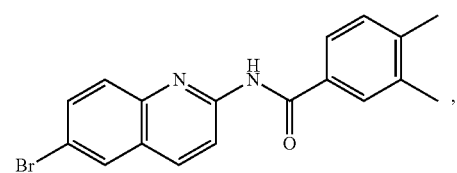
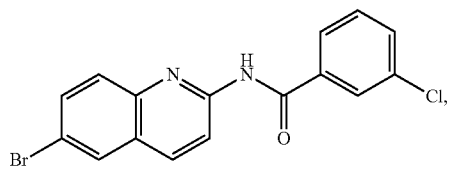
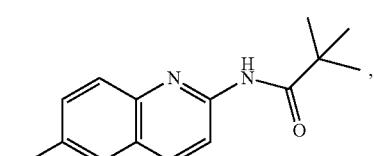
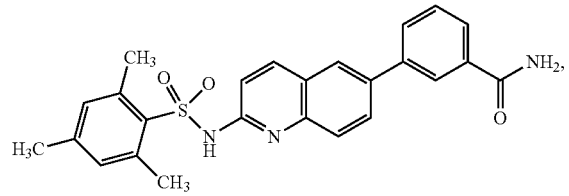
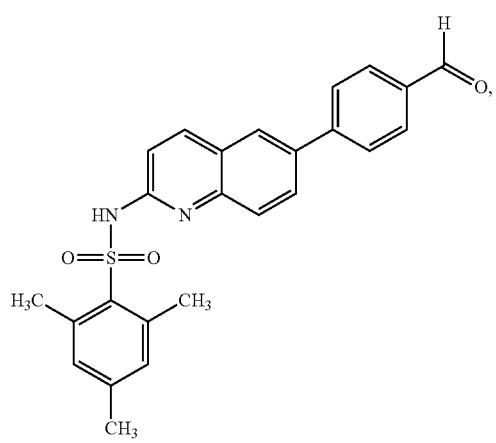
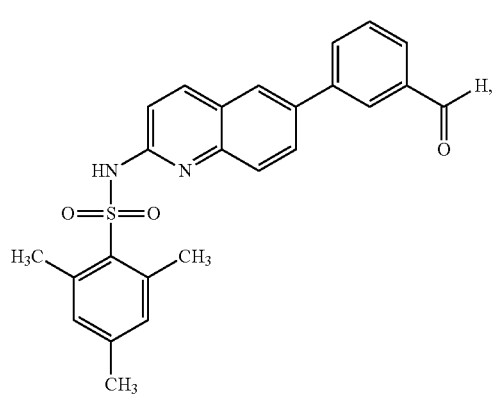
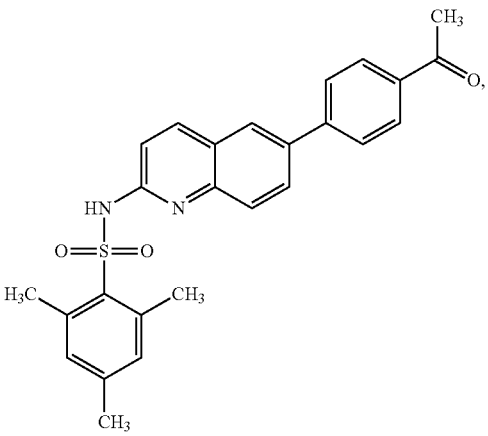
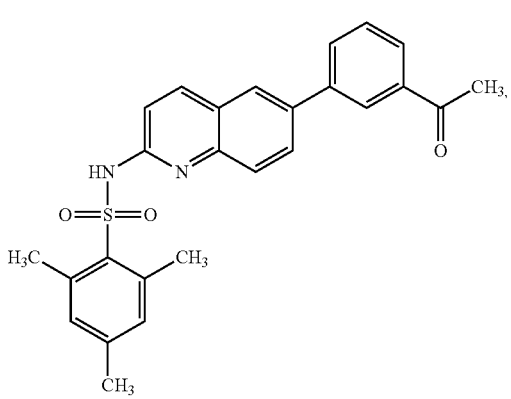
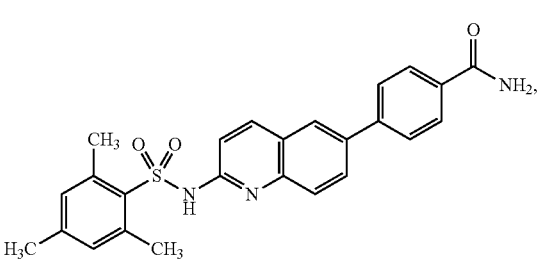
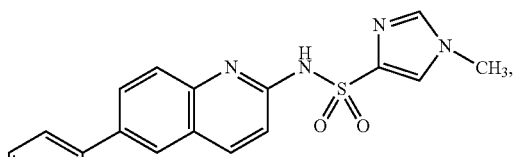
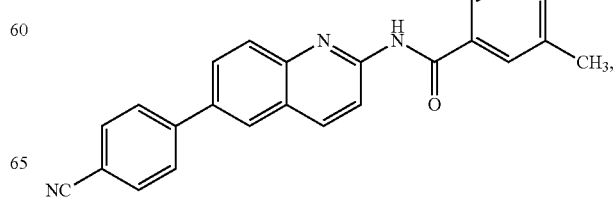

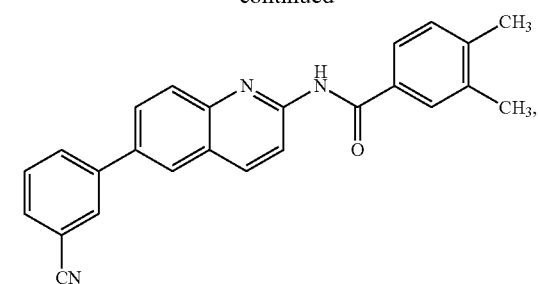
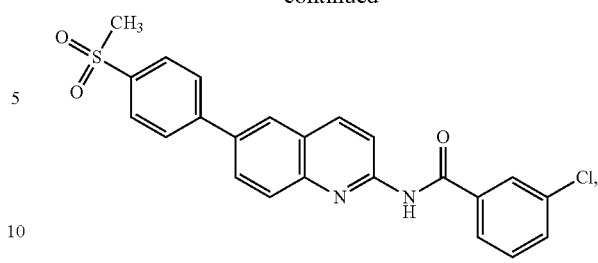
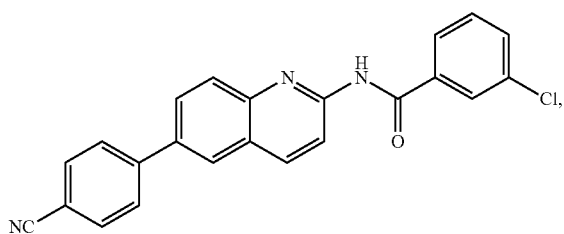
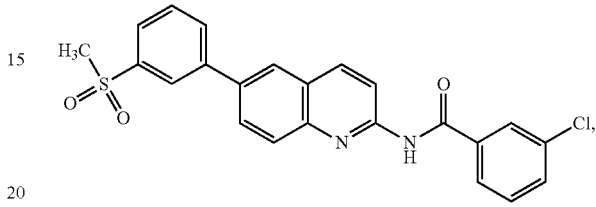
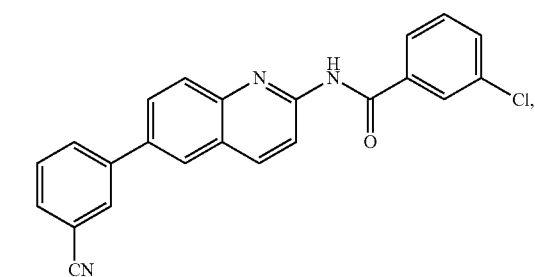
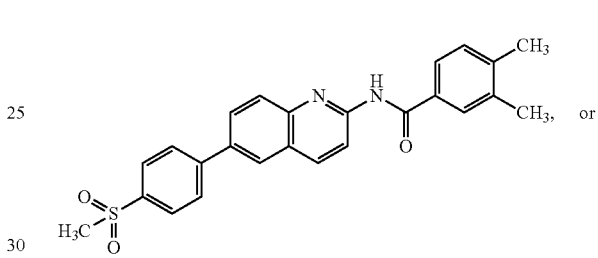
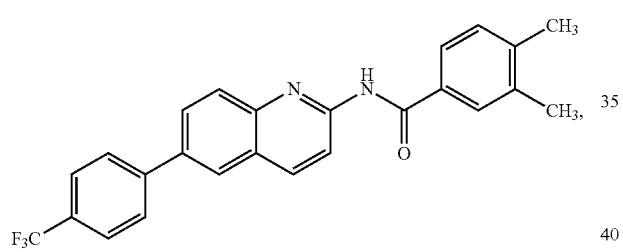
or
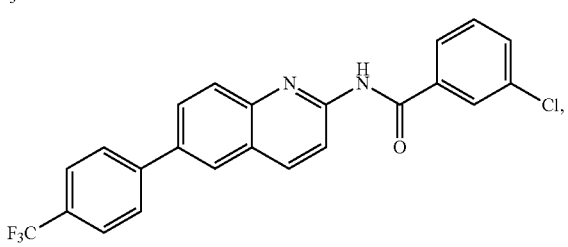
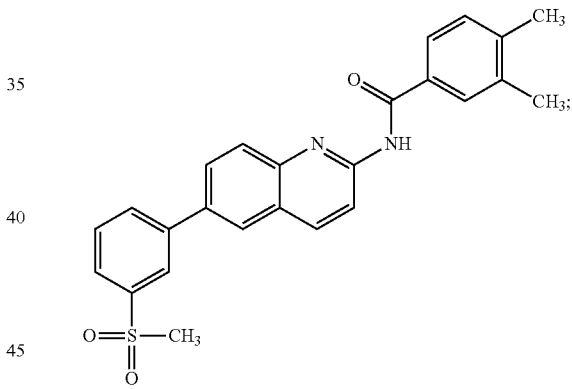
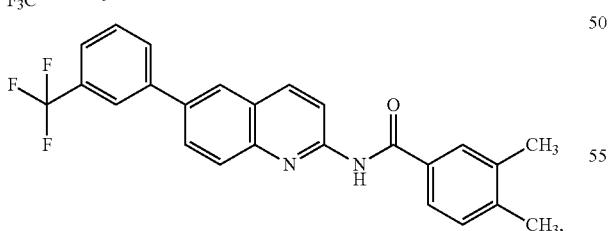
or a pharmaceutically acceptable salt thereof. In some embodiments, the compound is:
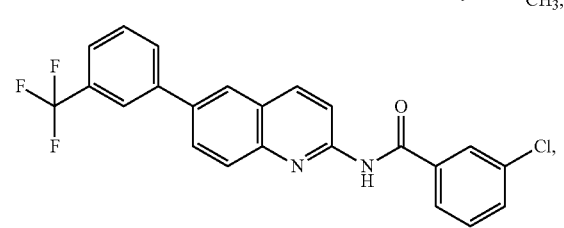
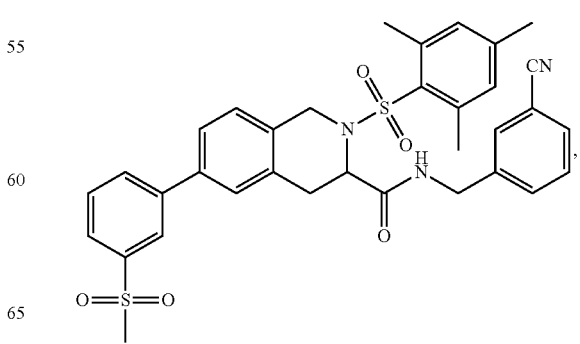

-continued
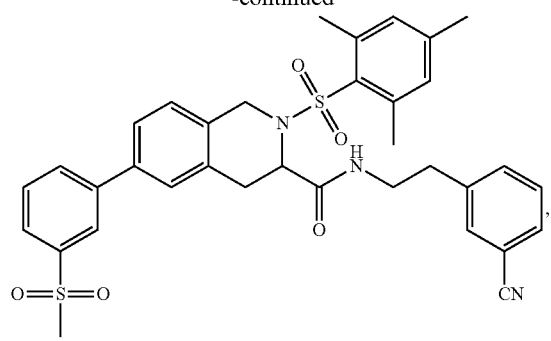
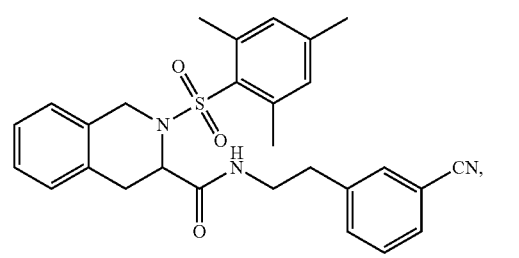
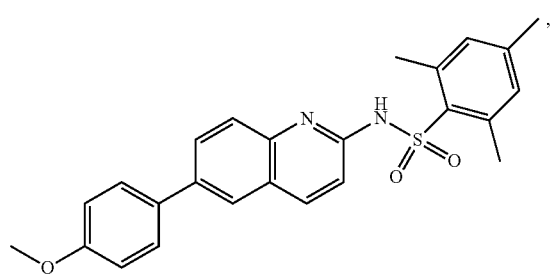
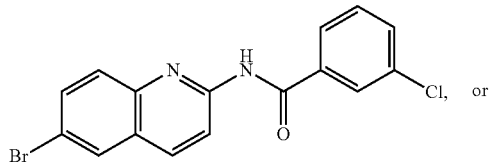
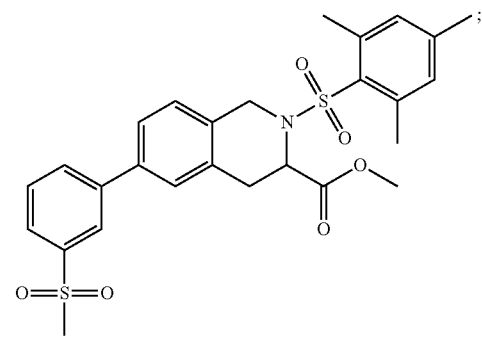 [SMILES: COC(=O)C1Cc2cc(-c3cccc(S(C)(=O)=O)c3)ccc2CN1S(=O)(=O)c1c(C)cc(C)cc1C]
The compound may in particular be defined as:
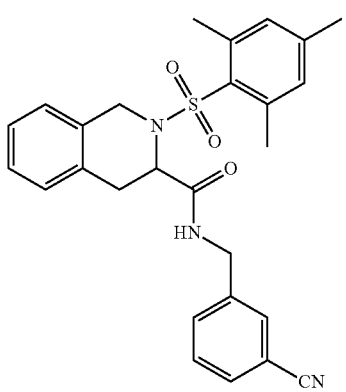
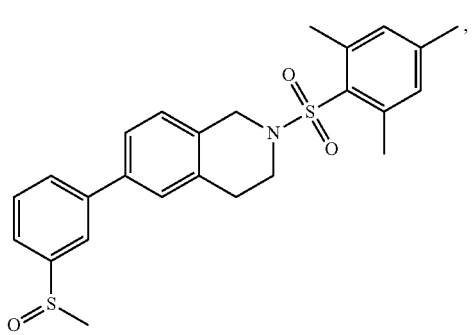
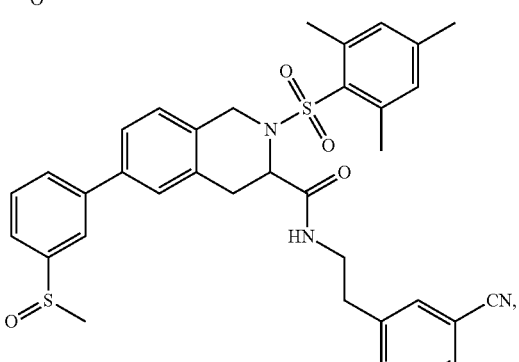
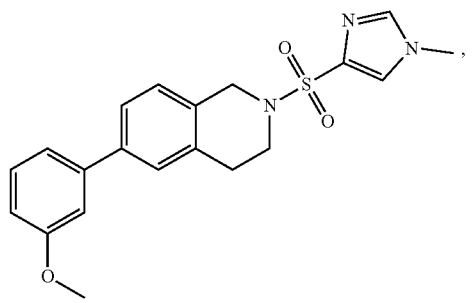
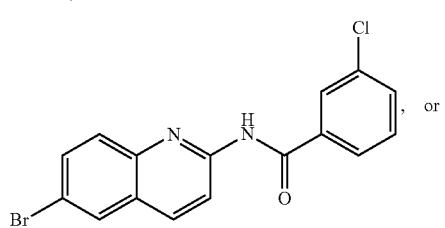

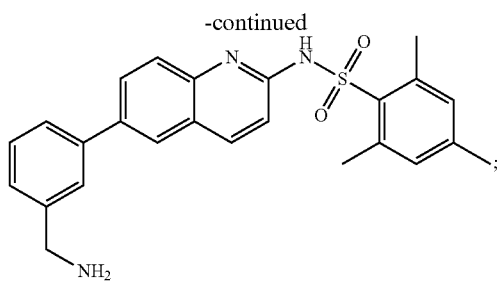

or a pharmaceutically acceptable salt thereof.

The compound may be an liver X receptor inverse agonist, such as one that results in a decrease of 10%, 20%, 30%, 40%, 50%, 60% or 70%, or ranges of 10-20%, 10-30%, 10-40%, 10-50%, 10-60% or 10-70% of the activity of the liver X receptor.

Also provided is pharmaceutical composition comprising (a) a compound disclosed herein; and (b) an excipient. The pharmaceutical composition may be formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. The pharmaceutical composition may be formulated for oral administration, intraarterial administration, intravenous administration, or intraperitoneal administration. The pharmaceutical composition may be formulated as a unit dose. The pharmaceutical composition may further comprise a second anti-cancer therapy. The second anti-cancer therapy may be a second chemotherapeutic agent, such as 5-fluorouracil, cisplatin, abiraterone acetate, enzalutamide, cabazitaxel, methotrexate, carboplatin, gemcitabine, paclitaxel, cyclophosphamide, doxorubicin, mitoxantrone, estramustine, irinotican, capecitabine, etoposide or vincristine. The second anti-cancer therapy is an immunotherapy, such as sipuleucel-T, ipilimumab, bevacizumab, nivolumab, pembrolizumab, Baccilus Calmette Guerin, imiquimod, panitumumab, pertuzumab, trastuzumab, cetuximab or denosumab.

In yet another embodiment, there is provided a method of treating a disease or disorder in a patient comprising administering to the patient a therapeutically effective amount of a compound or composition described above. The disease or disorder may be cancer, such as a carcinoma, sarcoma, lymphoma, leukemia, melanoma, mesothelioma, multiple myeloma, or seminoma, or a cancer of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In particular, the the cancer is breast cancer, colon cancer, lung cancer, pancreatic cancer, prostate cancer, lymphoma, leukemia, glioblastoma, medulloblastoma, melanoma, head and neck cancer, basal cell carcinoma, ovarian cancer, bladder cancer. The method may further comprise providing a second anti-cancer therapy, such as surgery, radiotherapy, immunotherapy, or a second chemotherapeutic agent. The second anti-cancer therapy may be an immunotherapy, such as sipuleucel-T, ipilimumab, bevacizumab, nivolumab, pembrolizumab, Baccilus Calmette Guerin, imiquimod, panitumumab, pertuzumab, trastuzumab, cetuximab or denosumab. The second anti-cancer therapy is a second chemotherapeutic agent, such as 5-fluorouracil, cisplatin, abiraterone acetate, enzalutamide, cabazitaxel, methotrexate, carboplatin, gemcitabine, paclitaxel, cyclophosphamide, doxorubicin, mitoxantrone, estramustine, irinotican, capecitabine, etoposide or vincristine.

The disease or disorder may be associated with elevated cholesterol levels, such as atherosclerosis. The method may further comprise a second therapy, such as a change in diet, surgery, or administration of a second agent. The second agent may be an HMG-CoA reductase inhibitor, such as a statin. The method may further comprise administering the compound once, or two or more times. The patient may be a mammal, such as a human.

In still a further embodiment, there is provided a method of inhibiting activity of a liver X receptor comprising contacting the liver X receptor with a compound or composition as described above. The method may be performed in vivo or in vitro. The method may results in a 10%, 20%, 30%, 40%, 50%, 60% or 70%, including ranges of 10-20%, 10-30%, 10-40%, 10-50%, 10-60% or 10-70% decrease in liver X receptor activity. The method may be sufficient to inhibit glycolysis or lipogenesis, such as sufficient to inhibit glycolysis and/or to inhibit lipogenesis.

In another aspect, the present disclosure provides pharmaceutical compositions comprising:

(A) a compound described herein; and
(B) an excipient.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In some embodiments, the pharmaceutical composition is formulated as a unit dose.

In still another aspect, the present disclosure provides methods of treating cancer in a patient comprising administering to the patient in need thereof a therapeutically effective amount of a compound or composition described herein. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the method comprises a second anti-cancer therapy. In some embodiments, the second anti-cancer therapy is a second chemotherapeutic agent, radiotherapy, immunotherapy, or surgery. In some embodiments, the patient is a mammal such as a human. In some embodiments, the method comprises administering the compound once. In other embodiments, the method comprises administering the compound two or more times.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Cultured dendritic cell chemokine expression is inhibited by LXR agonists and tumor specific LXR ligands that is disrupted by SR9243. (FIG. 1B) SR9243 induces cytotoxic T-cell activity and dendritic cell activity in lung and breast tumor bearing mice.

DESCRIPTION OF ILLUSTRATIVE EMBODIMENTS

Figure 1A:
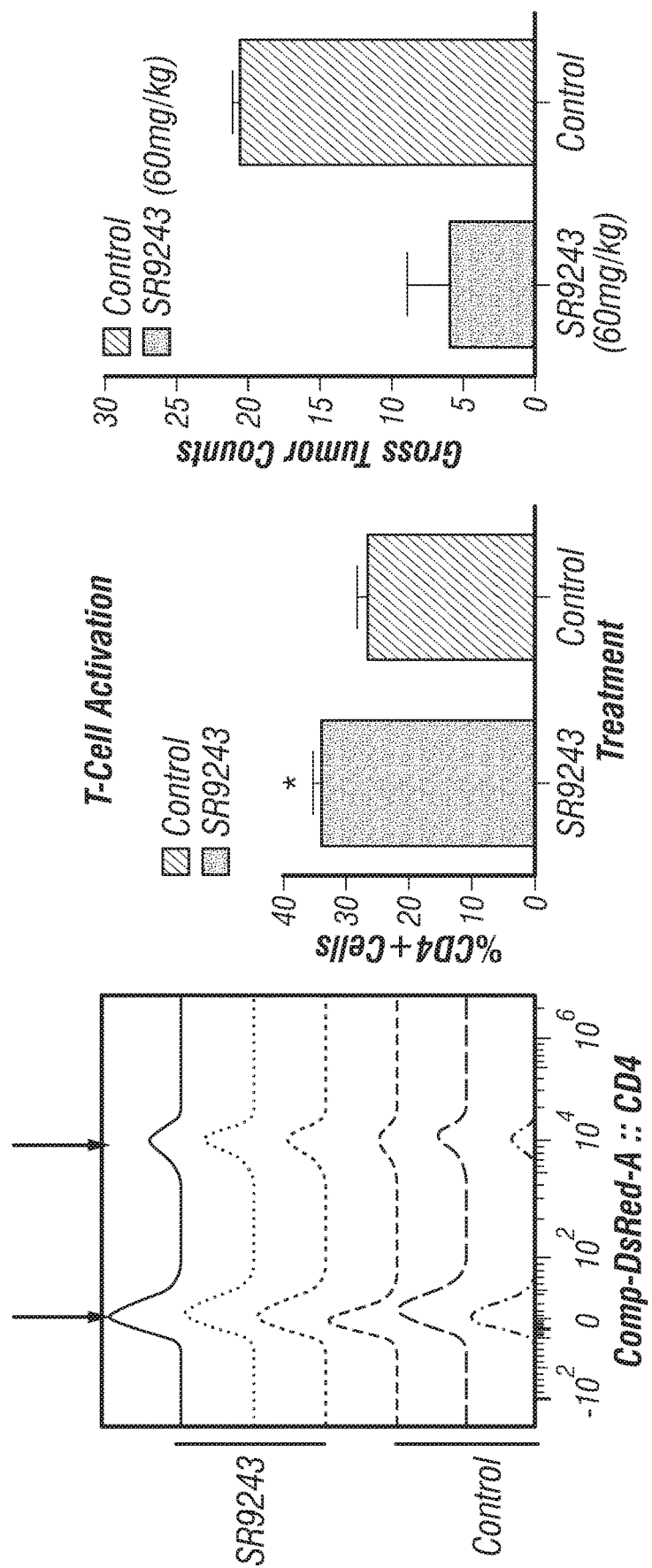
FIG. 1A-B—Inhibition of LXR activation stimulates tumor specific immune response.
Figure 1B:
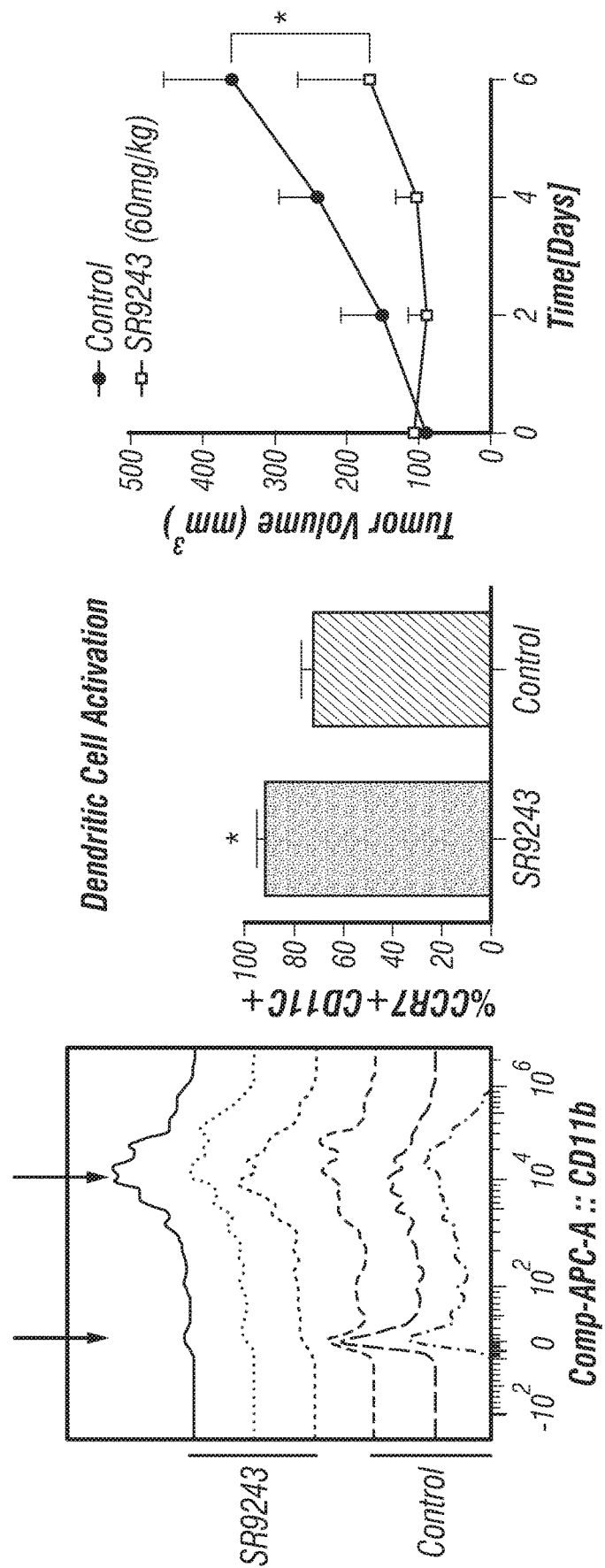

Because LXR is a key regulator of glycolysis and lipogenesis, enzymes that mediated the Warburg effect and tumor lipogenesis respectively, the inventros decided to target LXR to disrupt cancer cell growth. They designed LXR inverse agonists to lower the basal transcriptional activity of LXRs and promote suppression of the Warburg effect and lipogenesis, thereby offering broad based anti-cancer therapeutic activity. Thus, the present disclosure provides new LXR inverse agonists, which may be used in the treatment of cancer. These compounds may be used in pharmaceutical formulations and/or in methods of treating cancer or other hyperproliferative disease.

In particular, in the context of cancer immunotherapy, tumors produce LXR agonists that suppress dendritic cell lymphoid homing activity leading to a blunting of immune-mediated detection and clearance of tumor cells. LXR activation in dendritic cells within the tumor microenvironment results in reduced expression of the chemokine receptor CCR7, which is vital to dendritic migration to lymph nodes in response to exposure to tumor antigens. LXR inverse agonists can enhance CCR7 expression in dendritic cells, increase dendritic cell homing to lymph nodes and as a result stimulates immune-mediated tumor clearance. Therefore LXR inverse agonists can act as cancer immunotherapy agents.

I. Liver X Receptors and Inverse Agonists Thereof

A. LXRs

The liver-X-receptors, LXRa and LXRb (NR1H3 and NR1H2, respectively) are nuclear receptors and key regulators of lipid, cholesterol, and carbohydrate metabolism and homeostasis (Kim et al., 2009; Laffitte et al., 2003; Wang et al., 2008; Zhao et al., 2012). LXRb is ubiquitously expressed, whereas LXRa is expressed in macrophages, liver, adipose, adrenal, intestinal, and lung tissue. Both isoforms form obligate heterodimers with the retinoid-X-receptor (RXR) and bind to endogenous agonists such as the oxysterols 22(R)-hydroxycholesterol and 24(S)-hydroxycholesterol (Baranowski, 2008). LXRs regulate gene expression by directly binding to LXR-responsive elements (LXREs) within the promoter region of LXR-regulated genes. Unliganded LXRs selectively recruit corepressors such as nuclear corepressor 1 and 2 (NCoR1 and SMRT) to form repressor complexes at LXR-target gene promoters (Phelan et al., 2008; Wagner et al., 2003). Through this mechanism, LXRs silence target gene expression in the absence of ligand activation. Conversely, LXR agonist binding induces dissociation of corepressor complexes and recruitment of LXR coactivators such as thyroid hormone receptor-associated protein (TRAP220/DRIP-2). Coactivator recruitment by ligand-activated LXRs initiates transcription of LXR target genes such as glycolysis enzymes; PFK2 and GCK1 (Kim et al., 2009; Zhao et al., 2012) and lipogenesis genes; SREBP1c, FASN, and SCD1 (Darimont et al., 2006; Joseph et al., 2002; Zhang et al., 2006). Apart from their role in glycolysis and lipogenesis gene regulation, LXRs are also known to attenuate immune function as evidenced by LXR aberrant inflammatory signaling in LXR knockout mice (Jamroz-Wisniewska et al., 2007; Wojcicka et al., 2007). Moreover, LXR activation stimulates cholesterol efflux via stimulation of activation of ABC transporters (Beyea et al., 2007; Grefhorst et al., 2002). Therefore, LXR has been the focus of a number of studies aimed at developing cholesterol lowering drugs and treatments for atherosclerosis. Unfortunately, LXR agonists are known to promote hepatic steatosis due to enhanced hepatic lipid synthesis, which limits the potential use of LXR agonists as anti-artherogenic drugs in the clinic (Grefhorst et al., 2002; Viennois et al., 2012).

Recent studies have highlighted the emerging role of LXR in cancer metabolism, progression, and immune evasion (Russo, 2011; Villablanca et al., 2010). LXR agonists have been demonstrated to significantly lower intracellular cholesterol levels in cancer cells and therefore exhibit antineoplastic activity (Chuu and Lin, 2010; Rough et al., 2010). As a result, LXR agonists have been extensively investigated as pre-clinical anti-cancer drugs. In contrast, tumor cells have been shown to secrete LXR agonists that promote tumor immune evasion and survival (Russo, 2011; Villablanca et al., 2010). Similarly, inhibition of LXR activity also stimulated dendritic cell-mediated tumor cell clearance, enhanced tumor rejection, and prevented tumor recurrence in mice (Jamroz-Wisniewska et al., 2007; Russo, 2011; Villablanca et al., 2010). Furthermore, other investigations suggest that synthetic LXR agonists may be somewhat antagonistic to chemotherapy treatment (Miller et al., 2011). LXR agonists have been extensively investigated as anti-cancer agents despite the deleterious side effects. However, targeted inhibition of LXR activity to disrupt cancer growth has been left unexplored.

B. Inverse Agonists of the Present Disclosure

The LXR inverse agonists of the present disclosure are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All of the LXR inverse agonists of the present disclosure may be useful for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the LXR inverse agonists of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the LXR inverse agonists of the present disclosure have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

The LXR inverse agonists of the present disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the LXR inverse agonists of the present disclosure can have the S or the R configuration.

Chemical formulas used to represent the LXR inverse agonists of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the LXR inverse agonists of the present disclosure are intended to include all isotopic forms of such atoms. Isotopes, as used herein, include those atoms having the same atomic number but different mass numbers. By way of general example and without limitation, isotopes of hydrogen include tritium and deuterium, isotopes of carbon include $^{13}C$ and $^{14}C$, isotopes of oxygen include $^{17}O$ and $^{18}O$, and isotopes of nitrogen include $^{15}N$.

The LXR inverse agonists of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of the LXR inverse agonists of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. Cancer and Other Hyperproliferative Diseases

A. Oncogensis and the Warburg Effect

The metabolic profiles of cancer cells are distinct from those normal cells due to the Warburg effect and lipogenesis. These are key metabolic pathways that drive cancer progression, growth, survival, immune evasion, resistance to treatment, and disease recurrence (Fritz et al., 2010; Huang et al., 2012; Vander Heiden et al., 2009; Yeung et al., 2008). Therefore, by targeting glycolysis and lipogenesis, a broad range of cancers can be treated. This work establishes that targeted repression of glycolysis and lipogenesis can be achieved via suppression of LXR target-gene expression. Notably, LXR signaling has not been shown to initiate the Warburg effect in tumor cells. LXRs, however, directly regulate a number of key glycolytic and lipogenic enzymes that facilitate the Warburg effect and tumor lipogenesis, respectively. Therefore, we used an LXR inverse agonist to "hijack" the unliganded LXR and promote corepressor recruitment and formation of repressor complexes at the promoters of LXR-regulated genes. This approach reduced LXR transcriptional activity to below basal levels and therefore suppressed lipogenic and glycolytic gene expression, thereby inhibiting tumor growth.

The past few decades the Warburg effect and lipogenesis has been extensively studied with the goal of identifying targeted therapies that are selectively cytotoxic to cancer cells. A number of enzyme-specific inhibitors that target glycolysis enzymes and lipogenesis enzymes have been tested in rodent cancer models. Despite these efforts, no clinically viable cancer metabolism glycolysis inhibitor, 2-deoxy-glucose, has made it to phase II clinical trials (Mohanti et al., 1996). The challenges of using enzyme-specific glycolysis and lipogenesis inhibitors for treating solid tumors may be inherently flawed due to their mode of action. Ideally, to effectively inhibit glycolytic and lipogenic enzyme activity, enzyme inhibitors must block the catalytic activity of overexpressed enzymes in tumor tissues. Cancer cells have a surplus pool of catalytically active enzyme molecules relative to normal cells. Therefore, to effectively disrupt tumor metabolism, enzyme-specific inhibitors are expected to selectively target and disrupt metabolic processes in relatively more metabolically active tumor cells while sparing less active nonmalignant cells. Therefore, the dosage of enzyme inhibitor required to obtain the desired therapeutic effects in vivo also adversely affects the metabolic functions of normal cells. These limitations restrict the "therapeutic window" significantly for enzyme-specific inhibitors as clinical treatments for solid tumors.

B. Cancers

While hyperproliferative diseases can be associated with any disease, which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the LXR inverse agonists described herein may be used to lead to decreased cell counts and as such can potentially be used to treat a variety of types of cancer lines. In some aspects, it is anticipated that the LXR inverse agonists described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. Atherosclerosis and Coronary Artery Diseases

In certain aspects, this disclosure relates to the use of LXR inverse agonists as agents to treat atherosclerosis, as well as related conditions such as coronary arter disease and heart disease. Atherosclerosis (also known as arteriosclerotic vascular disease or ASVD) is a specific form of arteriosclerosis in which an artery-wall thickens as a result of invasion and accumulation of white blood cells (WBCs) (foam cell) and proliferation of intimal-smooth-muscle cell creating a fibro-fatty plaque. The accumulation of the white blood cells is termed "fatty streaks" early on because of the appearance being similar to that of marbled steak. These accumulations contain both living, active WBCs (producing inflammation) and remnants of dead cells, including cholesterol and triglycerides. The remnants eventually include calcium and other crystallized materials within the outermost and oldest plaque. The "fatty streaks" reduce the elasticity of the artery walls. However, they do not affect blood flow for decades because the artery muscular wall enlarges at the locations of plaque. The wall stiffening may eventually increase pulse pressure; widened pulse pressure is one possible result of advanced disease within the major arteries.

Atherosclerosis is therefore a syndrome affecting arterial blood vessels due to a chronic inflammatory response of WBCs in the walls of arteries. This is promoted by low-density lipoproteins (LDL, plasma proteins that carry cholesterol and triglycerides) without adequate removal of fats and cholesterol from the macrophages by functional high-density lipoproteins (HDL). It is commonly referred to as a "hardening" or furring of the arteries. It is caused by the formation of multiple atheromatous plaques within the arteries.

The plaque is divided into three distinct components: (i) the atheroma, which is the nodular accumulation of a soft, flaky, yellowish material at the center of large plaques, composed of macrophages nearest the lumen of the artery; (ii) underlying areas of cholesterol crystals; and (iii) calcification at the outer base of older or more advanced lesions.

Atherosclerosis is a chronic disease that remains asymptomatic for decades. Atherosclerotic lesions, or atherosclerotic plaques, are separated into two broad categories: Stable and unstable (also called vulnerable). The pathobiology of atherosclerotic lesions is very complicated, but generally, stable atherosclerotic plaques, which tend to be asymptomatic, are rich in extracellular matrix and smooth muscle cells. On the other hand, unstable plaques are rich in macrophages and foam cells, and the extracellular matrix separating the lesion from the arterial lumen (also known as the fibrous cap) is usually weak and prone to rupture. Ruptures of the fibrous cap expose thrombogenic material, such as collagen, to the circulation and eventually induce thrombus formation in the lumen. Upon formation, intraluminal thrombi can occlude arteries outright (e.g., coronary occlusion), but more often they detach, move into the circulation, and eventually occlude smaller downstream branches causing thromboembolism. Apart from thromboembolism, chronically expanding atherosclerotic lesions can cause complete closure of the lumen. Chronically expanding lesions are often asymptomatic until lumen stenosis is so severe (usually over 80%) that blood supply to downstream tissue(s) is insufficient, resulting in ischemia.

These complications of advanced atherosclerosis are chronic, slowly progressive and cumulative. Most commonly, soft plaque suddenly ruptures (see vulnerable plaque), causing the formation of a thrombus that will rapidly slow or stop blood flow, leading to death of the tissues fed by the artery in approximately five minutes. This catastrophic event is called an infarction. One of the most common recognized scenarios is called coronary thrombosis of a coronary artery, causing myocardial infarction (a heart attack). The same process in an artery to the brain is commonly called stroke. Another common scenario in very advanced disease is claudication from insufficient blood supply to the legs. Atherosclerosis affects the entire artery tree, but mostly larger, high-pressure vessels such as the coronary, renal, femoral, cerebral, and carotid arteries. These are termed clinically "silent" because the person having the infarction does not notice the problem and does not seek medical help, or when they do, physicians do not recognize what has happened.

Coronary Artery Diseases (CAD) are diseases of the arteries that supply the heart muscle with blood. This particular type of cardiovascular disease is the most common form of heart disease in industrialized nations and far and away the leading cause of heart attacks. Coronary artery disease generally means that blood flow through the arteries has become impaired. The most common way such obstructions develop is through a condition called atherosclerosis, a largely preventable type of vascular disease. These arteries, whose inner lining is normally smooth, may slowly become clogged with deposits of fats, cholesterol and other material, called atherosclerotic plaques. As a result of the buildup of these atherosclerotic plaques, the supply of blood, which supplies nutrients and oxygen to the heart muscle, is choked off resulting in a myocardial ischemia. Chest pain, or angina pectoris, occurs in cases when the oxygen demand of the heart muscle exceeds the oxygen supply as a result of the buildup of these plaques. When the imbalance of oxygen supply lasts for more than a few minutes, heart muscle can begin to die, causing a heart attack also known as a myocardial infarction. Heart attacks may occur without symptoms (silent heart attack), especially in people with diabetes. Furthermore, a heart attack may lead to congestive heart failure. Additionally, the lack of blood, even briefly, may lead to serious disorders of the heart rhythm such as arrhythmias or dysrhythmias. Coronary artery disease can even cause sudden death from an arrhythmia without any prior warning. Other non-limiting examples of cardiovascular diseases include cardiomyopathy, valvular heart disease, pericardial disease, congenital heart disease, and congestive heart failure. Some non-limiting examples of diseases of the blood vessels include high blood pressure, aneurysms, occlusive artery disease, vasculitis, and venous thrombosis.

IV. Pharmaceutical Formulations and Routes of Administration

For the purpose of administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of an LXR inverse agonist of the present disclosure formulated with one or more excipients and/or drug carriers appropriate to the indicated route of administration. In some embodiments, the compounds of the present disclosure are formulated in a manner amenable for the treatment of human and/or veterinary patients. In some embodiments, formulation comprises admixing or combining one or more of the compounds of the present disclosure with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. Pharmaceutical formulations may be subjected to conventional pharmaceutical operations, such as sterilization and/or may contain drug carriers and/or excipients such as preservatives, stabilizers, wetting agents, emulsifiers, encapsulating agents such as lipids, dendrimers, polymers, proteins such as albumin, or nucleic acids, and buffers, etc.

Pharmaceutical formulations may be administered by a variety of methods, e.g., orally or by injection (e.g., subcutaneous, intravenous, intraperitoneal, etc.). Depending on the route of administration, the LXR inverse agonists of the present disclosure may be coated in a material to protect the compound from the action of acids and other natural conditions which may inactivate the compound. To administer the active compound by other than parenteral administration, it may be necessary to coat the compound with, or co-administer the compound with, a material to prevent its inactivation. For example, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The LXR inverse agonists of the present disclosure may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The LXR inverse agonists of the present disclosure can be administered orally, for example, with an inert diluent or an assimilable edible carrier. The compounds and other ingredients may also be enclosed in a hard or soft shell gelatin capsule, compressed into tablets, or incorporated directly into the subject's diet. For oral therapeutic administration, the compounds of the present disclosure may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

In some embodiments, the therapeutic compound may also be administered topically to the skin, eye, or mucosa. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. In some embodiments, the specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In general a human equivalent dose (HED) in mg/kg can be calculated in accordance with the following formula (see, e.g., Reagan-Shaw et al., FASEB J., 22(3): 659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of LXR inverse agonists of the present disclosure or composition comprising LXR inverse agonists of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the subject has eaten or will eat.

V. Methods of Treatment

In particular, the compositions that may be used in treating cancer or atherosclerosis in a subject (e.g., a human subject) are disclosed herein. The compositions described above are administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently.

In the context of cancer therapy, composition as described herein is typically administered at a dosage that inhibits the growth or proliferation of a cancer cell or induces death of cancerous cells (e.g., induces apoptosis of a cancer cell), as assayed by identifying a reduction in hematological parameters (complete blood count—CBC), or cancer cell growth or proliferation. In some embodiments, amounts of the LXR inverse agonists described herein used will be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the LXR inverse agonists described herein may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects' "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

VI. Combination Therapies

A. Cancer

It is envisioned that the LXR inverse agonists described herein may be used in combination therapies with one or more cancer therapies or a compound, which mitigates one, or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the LXR inverse agonists described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A; uncialamycin and derivatives thereof; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

In one aspect of immunotherapy focuses on checkpoint blockade in which tumor cells express inhibitor receptors (MHC-1, B7-1, B7-2, MHCII) or receptor ligands (PDL-1 that stimulate T-cell anergy/apoptosis and thereby suppress immune response to tumor growth. Therapeutic antibodies or checkpoint blockade inhibitors have been designed to disrupt tumor mediated immune suppression. Common therapeutically targeted immune checkpoint proteins include the immune inhibitory PD-1, PDL-1, A2AR, CTLA-4, IDO, MR and TIM-3 or the immune stimulatory OX40, A2AR, GITR, LAG3 and ICOS. Targeting these immune-modulatory proteins has been shown to have anti-cancer effects.

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MCP-1β, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyerproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

B. Atherosclerosis, CAD and Heart Disease

In another embodiment, the combination therapy may involve the use of the disclosed LXR inverse agonists with other agents that treat atherosclerosis, CAD and heart disease. In general, the combination will follow the outline set out above for cancer, but will employ other "second" agents, such as Antihyperlipoproteinemics ((aryloxyalkanoic/fibric acid derivative, a resin/bile acid sequesterant, an HMG CoA reductase inhibitor, a nicotinic acid derivative, a thyroid hormone or thyroid hormone analog), and other miscellaneous antihyperlipoproteinemics including acifran, azacosterol, benfluorex, b-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, g-oryzanol, pantethine, pentaerythritol tetraacetate, α-phenylbutyramide, pirozadil, probucol (lorelco), b-sitosterol, sultosilic acid-piperazine salt, tiadenol, triparanol and xenbucin.

Anti-arteriosclerotics, antithrombotics/fibrinolytics, anticoagulants, antiplatelets, thrombolytics, antiarrhythmic agents (Clas I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers)), antihypertensives, diuretics, inotropic agents and antianginal agents are contemplated as well.

VII. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

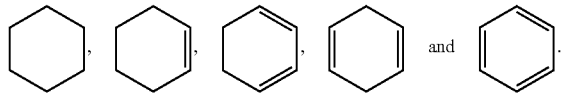

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "〜〜〜", when drawn perpendicularly across a bond

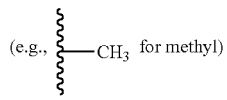

indicates a point of attachment of the group. It is noted that the point of attachment is typically only identified in this manner for larger groups in order to assist the reader in unambiguously identifying a point of attachment. The symbol "◄■" means a single bond where the group attached to the thick end of the wedge is "out of the page." The symbol "◁▥" means a single bond where the group attached to the thick end of the wedge is "into the page". The symbol "〜〜〜" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

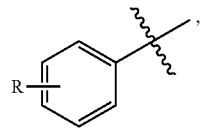

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

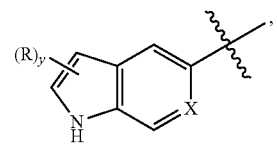

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C≤10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups $CH_3$ (Me), $-CH_2CH_3$ (Et), $-CH_2CH_2CH_3$ (n-Pr or propyl), $-CH(CH_3)_2$ (i-Pr, $^i$Pr or isopropyl), $-CH_2CH_2CH_2CH_3$ (n-Bu), $-CH(CH_3)CH_2CH_3$ (sec-butyl), $-CH_2CH(CH_3)_2$ (isobutyl), $-C(CH_3)_3$ (tert-butyl, t-butyl, t-Bu or $^t$Bu), and $-CH_2C(CH_3)_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $-CH_2-$ (methylene), $-CH_2CH_2-$, $-CH_2C(CH_3)_2CH_2-$, and $-CH_2CH_2CH_2-$ are non-limiting examples of alkanediyl groups. The term "alkylidene" when used without the "substituted" modifier refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, $-NH_2$, $-NO_2$, $-CO_2H$, $-CO_2CH_3$, —CN, —SH, $-OCH_3$, $-OCH_2CH_3$, —C(O)H, $-C(O)CH_3$, $-NHCH_3$, $-NHCH_2CH_3$, $-N(CH_3)_2$, $-C(O)NH_2$, $-C(O)NHCH_3$, $-C(O)N(CH_3)_2$, $-OC(O)CH_3$, $-NHC(O)CH_3$, $-NHC(O)OC(CH_3)_3$, $-S(O)CH_3$, $-S(O)_2CH_3$, $-S(O)_2OH$, or $-S(O)_2NH_2$. The following groups are non-limiting examples of substituted alkyl groups: $-CH_2OH$, $-CH_2Cl$, $-CF_3$, $-CH_2CN$, $-CH_2C(O)OH$, $-CH_2C(O)OCH_3$, $-CH_2C(O)NH_2$, $-CH_2C(O)CH_3$, $-CH_2OCH_3$, $-CH_2OC(O)CH_3$, $-CH_2NH_2$, $-CH_2N(CH_3)_2$, and $-CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, $-CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups $-CH_2F$, $-CF_3$, and $-CH_2CF_3$ are non-limiting examples of fluoroalkyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, $-C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

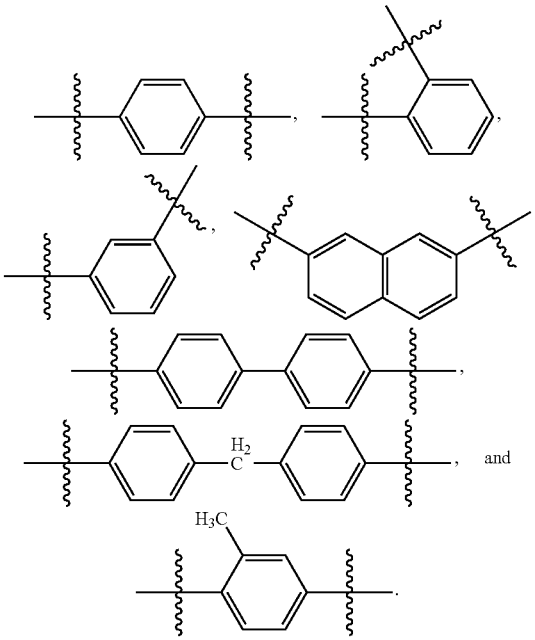

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, $-NH_2$, $-NO_2$, $-CO_2H$, $-CO_2CH_3$, —CN, —SH, $-OCH_3$, —OCH$_2$CH$_3$, —C(O)H, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —NHC(O)OC(CH$_3$)$_3$, —S(O)CH$_3$, —S(O)$_2$CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —NHC(O)OC(CH$_3$)$_3$, —S(O)CH$_3$, —S(O)$_2$CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —NHC(O)C(CH$_3$), —NHC(O)OC(CH$_3$)$_3$, —S(O)CH$_3$, —S(O)$_2$CH$_3$, —S(O)$_2$OH, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. When the term aralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)H, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —NHC(O)OC(CH$_3$)$_3$, —S(O)CH$_3$, —S(O)$_2$CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living organism, such as a human, monkey, horse, cow, sheep, goat, dog, cat, mouse, rat, guinea pig, or transgenic species thereof. In some embodiments, the patient or subject is a mammal. In some embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2', where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VIII. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Biochemical NR—Cofactor Peptide Interaction Assay (TR-FRET) Assay (Life Technologies kit). Purified human LXRα-LBD (GST), LXRβ-LBD (GST), fluorescein (FL)-labeled peptides, terbium (TB)-labeled anti-GST tag antibody, and all buffers were purchased from Life Technologies. All LXR assays were conducted in 384-well black medium-binding polystyrene assay plates (Greiner Bio-One). Test compound stock solutions and subsequent serial dilutions were prepared at 100× the final concentration in DMSO, and then were diluted to the final assay concentration of 2× in assay buffer and dispensed into assay plates. LXR-LBDs were added to assay plates and then a mixture of FL-peptide/TB-anti-GST was added to each well containing either a test compound or DMSO control for final concentrations of 2.5 nM LXRα-LBD, 5 nM LXRβ-LBD, 10 nM TB-anti-GST, and 250 nM FL-peptide. Assay plates were protected from light and incubated with gentle shaking for 3.5 hours at room temperature. The TR-FRET ratio (520 nm/492 nm) of each assay well was measured using the Perkin Elmer EnVision plate reader. An excitation filter at 340 nm was used to excite the TB-anti-GST and emission filters 492 nm and 520 nm were used to detect terbium and fluorescein emission signals respectively. A delay of 100 μs followed by a 200 μs integration time was used to collect the time-resolved emission signals.

The assay is identical except we use His-tagged LXR (made in house) and TB-labeled anti-His antibody (Life Technologies). FL-labeled peptides (Life Technologies) are:
NCOR-ID1 NCOR-ID2 SMRT SRC1-2 SRC2-3 TRAP/DRIP Transfection Assays. Twenty-four hours prior to transfection, HEK293 cells were seeded in 96-well plates at density of 15×10³ cells per well (Day 1). Transfections were performed using Lipofectamine 2000 (Invitrogen; Day 2). Twenty-four hours after the transfection, the cells were treated with vehicle or compound and incubated at 37° C. for another twenty-four hours (Day 3). Luciferase activity was measured using the Dual-Glo luciferase assay system (Promega) and analyzed using GraphPad Prism software (Day 4). Data were normalized to *Renilla* luciferase activity.

Example 2

Synthetic Procedures.

Compounds of the present invention that can be classified as di-substituted tetrahydroquinoline are summarized below. Compounds belonging to type A can be prepared from commercially available ester 1 and reaction with the requisite sulfonyl chloride as described in the literature (X) gives sulfonamide intermediate 1. Hydrolysis of the ester using an aqueous solution of a base such as lithium or sodium hydroxide gives the acid intermediate 2. Coupling of intermediate 2 with the requisite primary and secondary amines in the presence of an appropriate dehydrating agent gives compounds of type A. Compounds of type B were prepared using commercial starting material 2. Formation of the sulfonamide gives intermediate 3. Alternatively, acylation of 2 with the appropriate acid chloride or with a carboxylic acid using the appropriate dehydrating agent gives rise to amide intermediate 4. Performing a metal mediated cross coupling of intermediates 3 or 4 with an aryl-boronic acid (Suzuki coupling) using an appropriate palladium catalyst gives rise to compounds of type B and C. These types of transformations are well established in the literature. These examples lead to compounds of structural formula I.

Scheme 1: Synthetic Procedures to di-substituted tetrahydroquinoline derived compounds

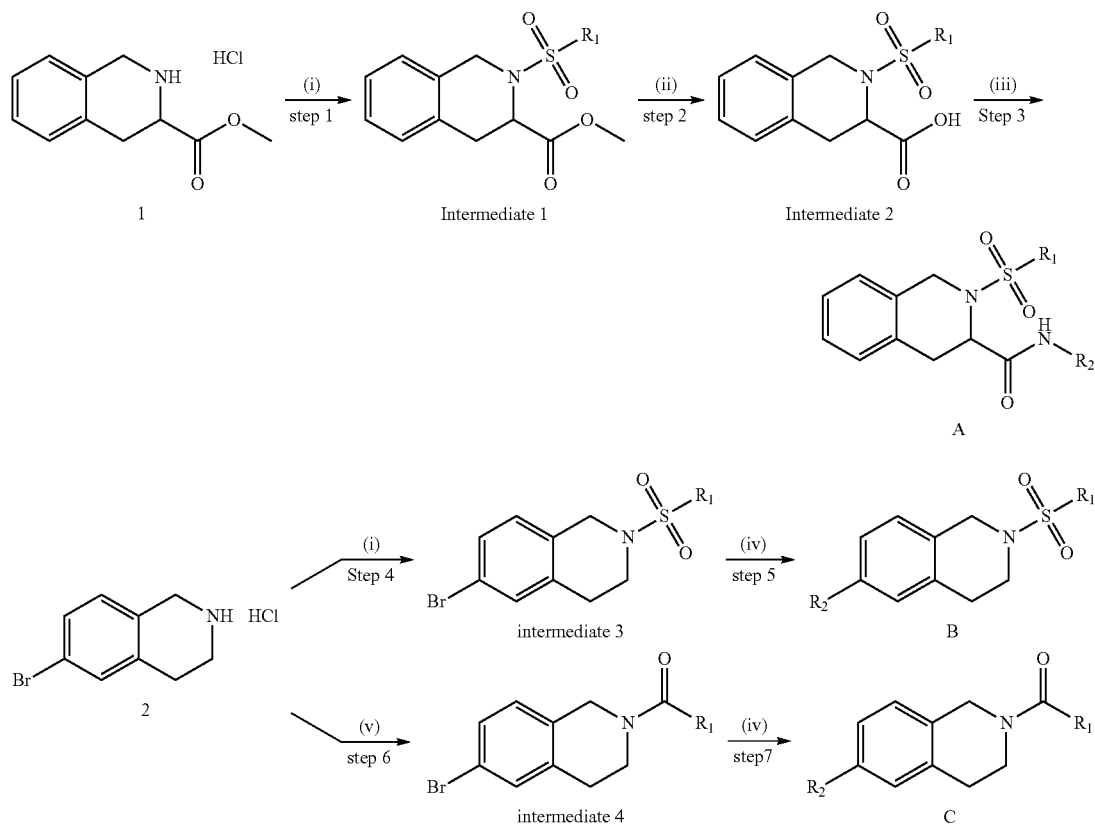

Reagents and conditions: (i) Sulfonyl chloride, K₂CO₃, acetone, rt; (ii) LiOH (4 eq) THF—H₂O (5-1), rt; (iii) amine, TBTU, iPr₂Net, CH₂Cl₂, rt; (iv) Boronic acid, Pd(dppf)Cl₂, CH₂Cl₂, Cs₂CO₃, dioxane-H₂O, 70° C.; (iv) R₁CO₂H, HBTU, iPr₂Net, CH₂Cl₂, rt.

Compounds classified as tri-substituted tetrahydroquinolines were prepared as outlined in Scheme 2. Synthesis of known bromide 8 (Horio 1996) was prepared in 5 steps from 3-bromophenyl alanine (3). Methylation of 3 using known procedure (Hein, Geary et al. 2005) gave ester 4. Protection of the amine as the ethyl carbamate followed by cyclization led to the protected tetrahydroquinoline gave compound 6 according to methodology employed to make related examples (Beadle, Coates et al. 2014, Kamenecka and Burris 2015). Deprotection and esterification gives compound 8. The sulfonamide Intermediate 5 was prepared as described above in Scheme 1. A Suzuki Miyaura cross coupling reaction of intermediate 5 (Wlochal and Bailey 2015) with the requisite boronic acids gives intermediate 6. Compounds of type D can then be prepared in two steps from intermediate 5 via hydrolysis of the ester and then coupling of the acid intermediate 7 with the desired primary and secondary amines in the presence of the appropriate dehydrating agent. Compounds of type E can be prepared by known procedures of reduction, oxidation and subsequent Wittig reaction (House 1972). Compounds of type F, where $R_5$=Ph groups, can be prepared from intermediate 8 which results from reduction of the ester using known protocols followed by a Mitsunobu reaction (Mitsunobu 1981) with the desired phenol reagents. Alternatively, where $R_5$=alkyl groups, the hydroxyl intermediate 8 can be deprotonated and treated with alkyl or benzyl halide reagents to give the alkyl ethers of type F. Finally, intermediate 8 when oxidized to the aldehyde using standard oxidation conditions gives intermediate 9. Compounds of type G can then be prepared via by reductive amination (Abdel-Magid, Carson et al. 1996) with the desired primary or secondary amines. Compounds in this example fall within structural formula I.

Scheme 2: Synthesis of tri-substituted dihydroquinoline compounds

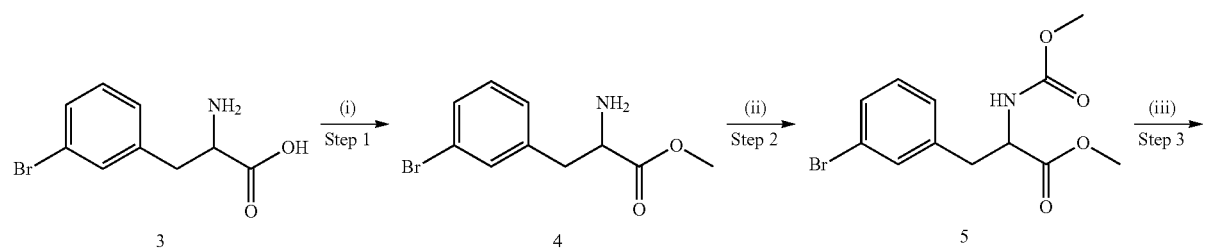

-continued

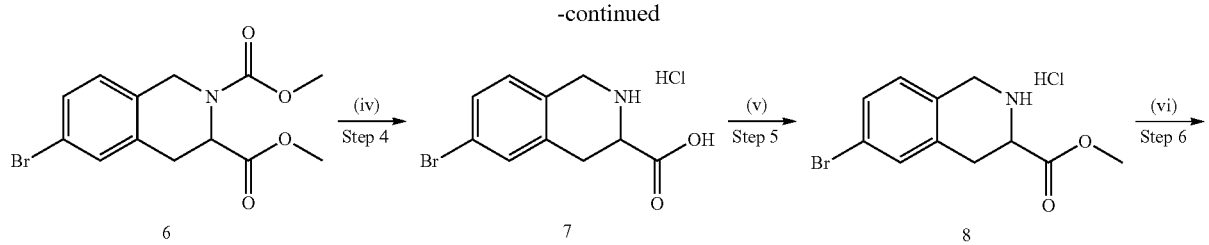

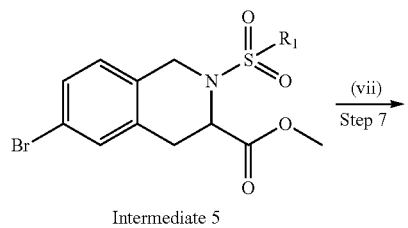

Intermediate 5

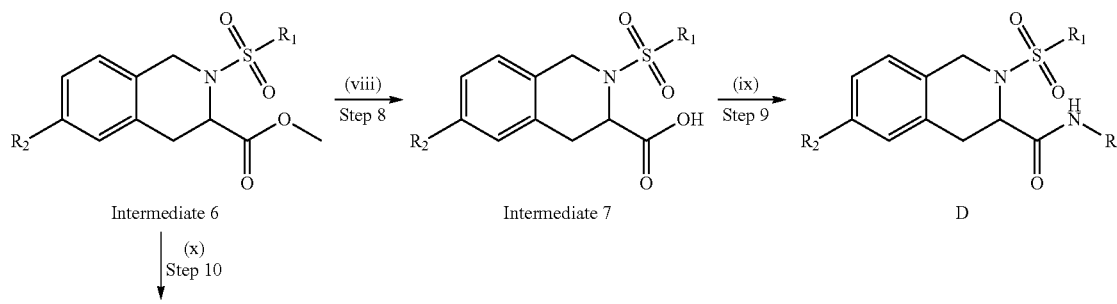

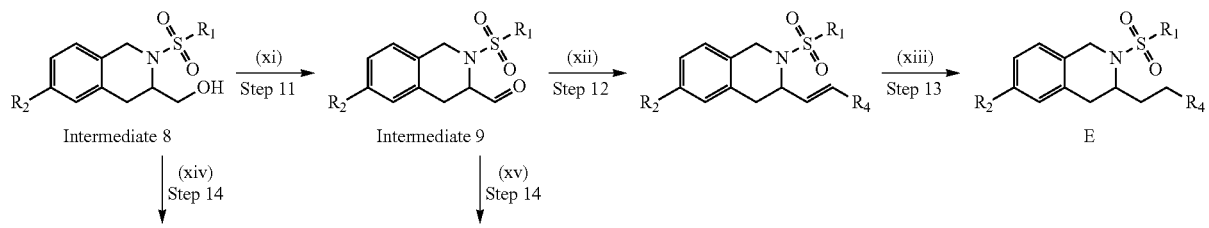

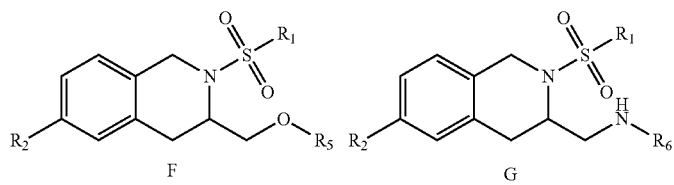

Reagents and conditions: (i) SOCl$_2$, MeOH, reflux, overnight; (ii) methylchloroformate, NaHCO$_3$, CH$_2$Cl$_2$—H$_2$O, rt, 2 h; (iii) paraformaldehyde, AcOH, conc. sulfuric acid, rt; (iv) 6N HCl, reflux, 3 d; (v) SOCl$_2$, MeOH, reflux; (vi) sulfonyl chloride, K$_2$CO$_3$, acetone, overnight; (vii) Boronic acid, Pd(dppf)Cl$_2$•DCM, Cs$_2$CO$_3$, dioxane, water, 70° C.; (viii) LiCl, MeOH, H$_2$O, rt, 2 h; (ix) amine, HBTU, Hunig's base, DMF, rt; (x) LiBH$_3$, THF, rt; (xi) MnO$_2$, DCM, rt; (xii) Phosphonium bromide, LDA, THF, -98° C.; (xiii) H$_2$, Pd—C 10%, MeOH; (xiv) Phenol, DIAD, PPh$_3$, DCE, rt; (xv) amines, sodium triacetoxyborohydride, AcOH, DCE, rt.

Compounds derived from an aminoquinoline scaffold of type H could be prepared in 2 steps as outlined in Scheme 3. The sulfonamide formation with 2-amino-6-bromoquinoline (9) could be achieved through addition of the requisite sulfonyl chloride in the presence of a mild base such as dimethylaminopyridine (DMAP). A Suzuki Myayura reaction with bromide intermediate 10 and requisite boronic acid with the appropriate palladium catalyst gave compounds of type H. Alternatively, aminoquinoline 9 could be treated with acid chlorides in the presence of a mild base such as DMAP to give the amide intermediate 11. Coupling of this intermediate under the Suzuki Myayura conditions with the desired boronic acids and appropriate catalyst gave the quinolone derivatives of type I. The compounds prepared in this example all fall within structure II.

Scheme 3. Synthesis of 6-substituted 2-aminoquinoline derivatives.

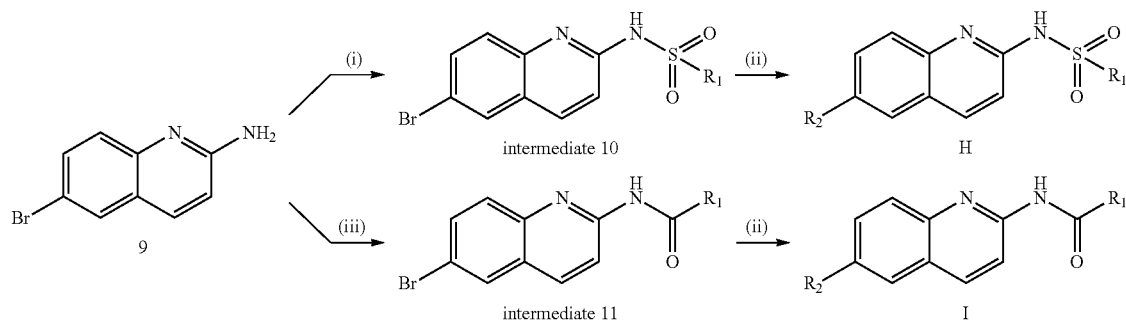

Reagents and Conditions: (i) R₁SO₂Cl, CH₃CN, DMAP, rt, 2 h (ii) Boronic acid, Pd(PPh₃)₄, DMF, Cs₂CO₃, 70° C.; 3 h (iii) R₁C(O)Cl, CH₃CN, DMAP, rt, 2 h.

Experimentals.
Compounds belonging to type A:

Synthesis of 2-(mesitylsulfonyl)-N-(4-(trifluoromethyl)benzyl)-1,2,3,4-tetrahydroisoquinoline-3-carboxamide

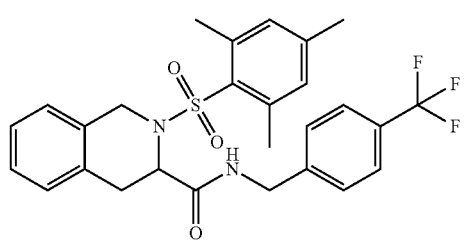

Step 1—methyl 2-(mesitylsulfonyl)-1,2,3,4-tetrahydroisoquinoline-3-carboxylate

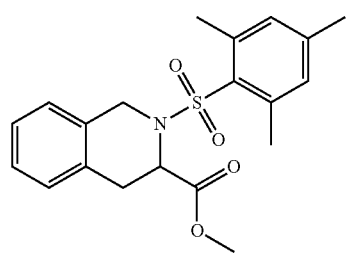 [SMILES: COC(=O)C1Cc2ccccc2CN1S(=O)(=O)c1c(C)cc(C)cc1C]

Methyl 1,2,3,4-tetrahydroisoquinoline-3-carboxylate hydrochloride (3 g, 13.17 mmol) and potassium carbonate (3.6 g, 26.34 mmol) were taken in acetone (250 mL). 2,4,6-trimethylbenzenesulfonyl chloride (3.5 g, 15.8 mmol) was added to the reaction mixture and stirred at ambient temperature for 16 h. Crude reaction mixture was concentrated under reduced pressure, extracted with saturated bicarbonate and brine, dried and concentrated. The crude mixture was purified on silica using ethyl acetate-hexane (40-60) to obtain the title compound (4.5 g, 92% yield). ¹H NMR (400 MHz, DMSO-d₆) δ ppm 2.27 (s, 3H) 2.54 (s, 6H) 3.14 (d, J=3.42 Hz, 3H) 4.32-4.50 (m, 2H) 4.77-4.83 (m, 1H) 7.08 (s, 2H) 7.17 (s, 4H). MS (m/z): 374.1 (M+H).

Step 2—Synthesis: 2-(mesitylsulfonyl)-1,2,3,4-tetrahydroisoquinoline-3-carboxylic Acid

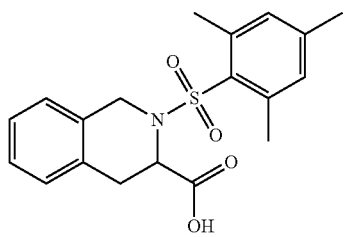 [SMILES: Cc1cc(C)c(S(=O)(=O)N2Cc3ccccc3CC2C(=O)O)c(C)c1]

Methyl 2-(mesitylsulfonyl)-1,2,3,4-tetrahydroisoquinoline-3-carboxylate (4.5 g, 12 mmol) was taken in methanol (100 mL). Lithium chloride (0.6 g, 24 mmol) in water (2 mL) was added to it and the reaction mixture was stirred at ambient temperature for 14 h. Crude reaction mixture was neutralized with 1N HCl. The precipitate formed was filtered and dried under reduced pressure to obtain the title compound (3.2 g, 74% yield). ¹H NMR (400 MHz, DMSO-d₆) δ ppm 2.27 (s, 3H) 2.55 (s, 6H) 3.02-3.20 (m, 3H) 4.36 (d, J=16.14 Hz, 2H) 4.49-4.57 (m, 2H) 4.66 (d, J=4.65 Hz, 2H) 7.07 (s, 4H) 7.16 (s, 8H). MS (m/z): 360.1 (M+H).

Step 3—Synthesis of 2-(mesitylsulfonyl)-N-(4-(trifluoromethyl)benzyl)-1,2,3,4-tetrahydroisoquinoline-3-carboxamide

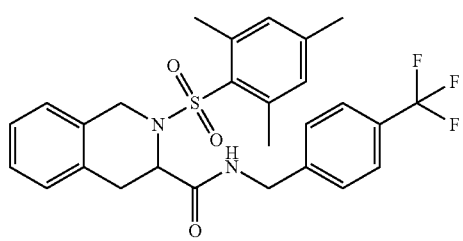

2-(mesitylsulfonyl)-1,2,3,4-tetrahydroisoquinoline-3-carboxylic acid (0.035 g, 0.1 mmol), TBTU (0.032 g, 0.1 mmol)

and Hunig's base (53 µl, 0.3 mmol) were taken in DMF (5 mL) and stirred for 30 min. (4-(trifluoromethyl)phenyl)methanamine (0.026 g, 0.15 mmol) was added to the reaction and stirred for 14 h. Reaction mixture was subsequently extracted with saturated bicarbonate and brine, dried and concentrated to get the crude mixture. The crude mixture was purified on silica using ethyl acetate-hexane (20-80) to obtain the title compound (0.045 g, 86% yield). $^1$H NMR (400 MHz, DMSO-$d_6$) δ ppm 2.27 (s, 3H) 2.54 (s, 6H) 3.06 (d, J=4.65 Hz, 2H) 4.16-4.32 (m, 2H) 4.44 (d, J=15.89 Hz, 1H) 4.61 (m, J=9.00 Hz, 1H) 4.70 (d, J=15.89 Hz, 1H) 7.07 (s, 2H) 7.13-7.26 (m, 6H) 7.57 (d, J=8.31 Hz, 2H) 8.51 (t, J=5.87 Hz, 1H). MS (m/z): 517.1 (M+H).

Compounds of Type B:

Synthesis of 2-(mesitylsulfonyl)-6-(3-(methylsulfonyl)phenyl)-1,2,3,4-tetrahydroisoquinoline

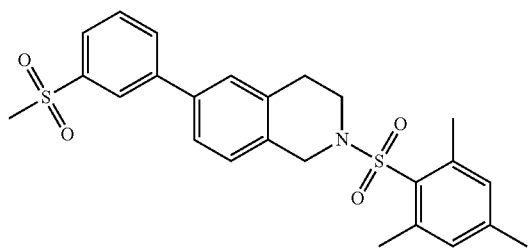

Step 1—Synthesis of 6-bromo-2-(mesitylsulfonyl)-1,2,3,4-tetrahydroisoquinoline

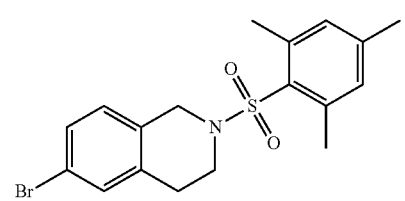 [SMILES: Cc1cc(C)c(S(=O)(=O)N2CCc3cc(Br)ccc3C2)c(C)c1]

6-bromo-1,2,3,4-tetrahydroisoquinoline hydrochloride (1.5 g, 6 mmol), and potassium carbonate (1.7 g, 12 mmol) were taken in acetone (100 mL). 2,4,6-trimethylbenzenesulfonyl chloride (1.6 g, 7.2 mmol) was added to the reaction mixture and stirred at ambient temperature for 16 h. Crude reaction mixture was concentrated under reduced pressure, extracted with saturated bicarbonate and brine, dried and concentrated. The crude mixture was purified on silica using ethyl acetate-hexane (30-70) to obtain the title compound (2.00 g, 85% yield). $^1$H NMR (400 MHz, DMSO-$d_6$) δ ppm 2.27-2.29 (m, 3H) 2.54 (s, 6H) 2.81 (t, J=6.00 Hz, 2H) 3.39 (t, J=5.99 Hz, 2H) 4.25 (s, 2H) 7.09 (s, 3H) 7.16 (d, J=8.31 Hz, 2H) 7.33-7.36 (m, 2H) 7.38 (m, J=2.00 Hz, 2H). MS (m/z): 396.0, 397.0 (M+H) for two bromine isomers.

Step 2—Synthesis of 2-(Mesitylsulfonyl)-6-(3-(methylsulfonyl)phenyl)-1,2,3,4-tetrahydroisoquinoline

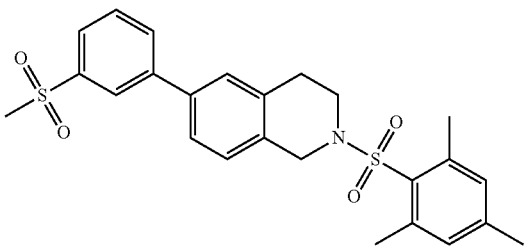

6-bromo-2-(mesitylsulfonyl)-1,2,3,4-tetrahydroisoquinoline (0.040 g, 0.1 mmol), (3-(methylsulfonyl)phenyl)boronic acid (0.025 g, 0.11 mmol), cesium carbonate (0.05 g, 0.14 mmol) and Pd(dppf)$_2$Cl$_2$·CH$_2$Cl$_2$ (0.01 g, 0.01 mmol) were taken in dioxane-water (5:1, 5 mL). The reaction mixture was heated at 60° C. for 14 h. Reaction mixture was subsequently extracted with saturated bicarbonate and brine, dried and concentrated to get the crude mixture. The crude mixture was purified on silica using ethyl acetate-hexane (30-70) to obtain the title compound (0.037 g, 80% yield). $^1$H NMR (400 MHz, DMSO-$d_6$) δ ppm 2.29 (s, 3H) 2.57 (s, 6H) 2.91 (t, J=5.75 Hz, 2H) 3.29 (s, 3H) 3.45 (t, J=5.87 Hz, 2H) 4.35 (s, 2H) 7.10 (d, J=0.49 Hz, 2H) 7.34 (d, J=8.80 Hz, 1H) 7.53-7.61 (m, 2H) 7.68-7.77 (m, 1H) 7.90 (ddd, J=7.83, 1.83, 1.10 Hz, 1H) 7.97-8.05 (m, 1H) 8.13 (s, 1H). MS (m/z): 470.1 (M+H).

Compounds of Type D:

Synthesis of methyl 2-(mesitylsulfonyl)-6-(3-(methylsulfonyl)phenyl)-1,2,3,4-tetrahydroisoquinoline-3-carboxylate

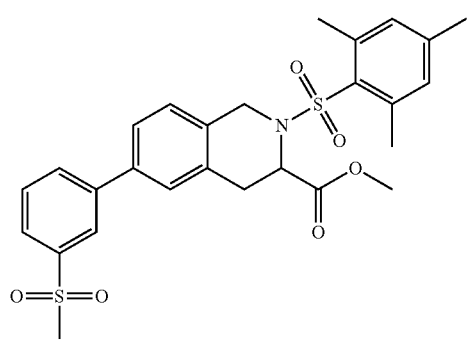

Step 1—methyl 2-amino-3-(3-bromophenyl)propanoate

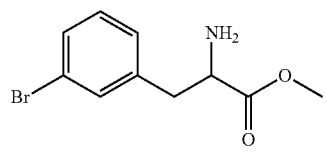

2-Bromo-D-phenylalanine (2 g, 8.19 mmol) was dissolved in methanol (50 mL) and cooled to 0° C. Thionyl chloride (1.5 mL, 20 mmol) was added drop-wise to the stirred reaction mixture. The reaction was allowed to warm up to the ambient temperature and heated for 14 h under reflux. Crude reaction mixture was concentrated under reduced pressure, extracted with saturated bicarbonate and brine, dried and concentrated to obtain the title compound (2.37 g, 98% yield). $^1$H NMR (400 MHz, DMSO-$d_6$) δ ppm 3.12 (m, J=1.00 Hz, 2H) 3.69 (s, 3H) 4.34 (t, J=6.72 Hz, 1H) 7.22-7.34 (m, 2H) 7.45-7.53 (m, 2H) 8.54 (br. s., 2H). MS (m/z): 258.0, 260.0 (M+H) for two bromine isomers.

Step 2—methyl 3-(3-bromophenyl)-2-((methoxycarbonyl)amino)propanoate

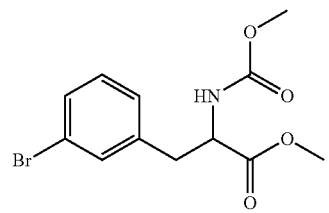 [SMILES: COC(=O)NC(Cc1cccc(Br)c1)C(=O)OC]

Methyl 2-amino-3-(3-bromophenyl)propanoate (2.35 g, 7.97 mmol) and sodium bicarbonate (1.3 g, 16 mmol) was taken in 50 mL of DCM and 10 mL of water at 0° C. Methyl chloroformate (1 mL, 13 mmol) is added slowly to the reaction mixture and stirred at ambient temperature for 2 h. Reaction mixture was subsequently extracted with saturated bicarbonate and brine, dried and concentrated to get the crude mixture. The crude mixture was purified on silica using ethyl acetate-hexane (30-70) to obtain the title compound (2.39 g, 95% yield). $^1$H NMR (400 MHz, DMSO-$d_6$) δ ppm 2.84 (dd, J=13.57, 10.39 Hz, 1H) 3.04 (dd, J=13.82, 5.01 Hz, 1H) 3.48 (s, 3H) 3.63 (s, 3H) 4.24 (ddd, J=10.45, 8.25, 5.01 Hz, 1H) 7.25 (d, J=5.14 Hz, 2H) 7.38-7.44 (m, 1H) 7.47 (s, 1H) 7.70 (d, J=8.31 Hz, 1H). MS (m/z): 316.0, 318.0 (M+H) for two bromine isomers.

Step 3: dimethyl 6-bromo-3,4-dihydroisoquinoline-2,3(1H)-dicarboxylate

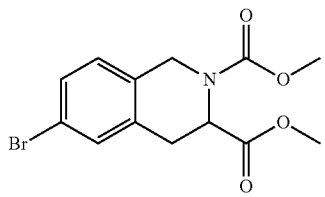 [SMILES: COC(=O)C1Cc2cc(Br)ccc2CN1C(=O)OC]

Methyl 3-(3-bromophenyl)-2-((methoxycarbonyl)amino)propanoate (2.29 g, 7.25 mmol) and paraformaldehyde (0.26 g, 8.7 mmol) were taken in acetic acid (9 mL). Conc. Sulfuric acid (1 mL) was added slowly to the reaction mixture and stirred for 16 h at ambient temperature. Concentrated to a slurry, neutralized with sat. sodium bicarbonate. Extracted with ethyl acetate and the organic layer was extracted with brine, dried and concentrated to get the crude mixture. The crude mixture was purified on silica using ethyl acetate-hexane (25-75) to obtain the title compound (2.08 g, 87% yield). $^1$H NMR (400 MHz, DMSO-$d_6$) δ ppm 3.13-3.26 (m, 2H) 3.60-3.77 (m, 3H) 4.31-4.48 (m, 1H) 4.54-4.68 (m, 1H) 4.89-5.11 (m, 1H) 7.14-7.30 (m, 2H) 7.39 (dd, J=8.19, 2.08 Hz, 1H) 7.44-7.55 (m, 1H). MS (m/z): 328.0, 333.0 (M+H) for two bromine isomers.

Step 4—6-bromo-1,2,3,4-tetrahydroisoquinoline-3-carboxylic Acid

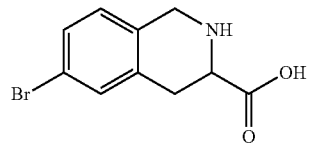 [SMILES: O=C(O)C1Cc2cc(Br)ccc2CN1]

Dimethyl 6-bromo-3,4-dihydroisoquinoline-2,3(1H)-dicarboxylate (2 g, 6.09 mmol) was taken in dioxane (10 mL) and 6N HCl (20 mL). The reaction mixture was refluxed for 3 d. The reaction mixture was concentrated to dryness to get the title compound (1.1 g, 56% yield). MS (m/z): 256.9, 257.9 (M+H) for two bromine isomers.

Step 5: methyl 6-bromo-1,2,3,4-tetrahydroisoquinoline-3-carboxylate

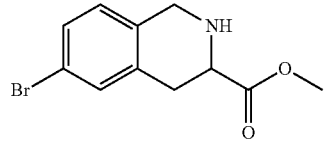

6-bromo-1,2,3,4-tetrahydroisoquinoline-3-carboxylic acid (1.1 g, 3.76 mmol) was dissolved in methanol (10 mL) and cooled to 0° C. Thionyl chloride (0.75 mL, 10 mmol) was added drop-wise to the stirred reaction mixture. The reaction was allowed to warm up to the ambient temperature and heated for 14 h under reflux. Crude reaction mixture was concentrated under reduced pressure, extracted with saturated bicarbonate and brine, dried and concentrated to obtain the title compound (1.0 g, 86% yield). MS (m/z): 256.0, 258.0 (M+H) for two bromine isomers.

Step 6—methyl 6-bromo-2-(mesitylsulfonyl)-1,2,3,4-tetrahydroisoquinoline-3-carboxylate

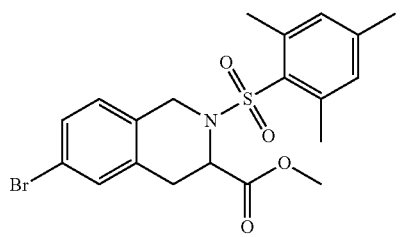 [SMILES: COC(=O)C1Cc2cc(Br)ccc2CN1S(=O)(=O)c1c(C)cc(C)cc1C]

Methyl 6-bromo-1,2,3,4-tetrahydroisoquinoline-3-carboxylate (0.5 g, 1.64 mmol) and potassium carbonate (0.45 g, 3.28 mmol) were taken in acetone (25 mL). 2,4,6-trimethylbenzenesulfonyl chloride (0.43 g, 1.96 mmol) was added to the reaction mixture and stirred at ambient temperature for 16 h. Crude reaction mixture was concentrated under reduced pressure, extracted with saturated bicarbonate and brine, dried and concentrated. The crude mixture was purified on silica using ethyl acetate-hexane (40-60) to obtain the title compound (0.55 g, 74% yield). $^1$H NMR (400 MHz, DMSO-d$_6$) δ ppm 2.27 (s, 3H) 2.53 (s, 6H) 3.11-3.18 (m, 2H) 3.51-3.57 (m, 3H) 4.38 (s, 2H) 4.80 (dd, J=6.24, 2.57 Hz, 1H) 7.09 (s, 2H) 7.17 (d, J=8.31 Hz, 1H) 7.36 (dd, J=8.19, 2.08 Hz, 1H) 7.44 (s, 1H). MS (m/z): 452.0, 454.0 (M+H) for two bromine isomers.

Step 7—methyl 2-(mesitylsulfonyl)-6-(3-(methylsulfonyl)phenyl)-1,2,3,4-tetrahydroisoquinoline-3-carboxylate, 3

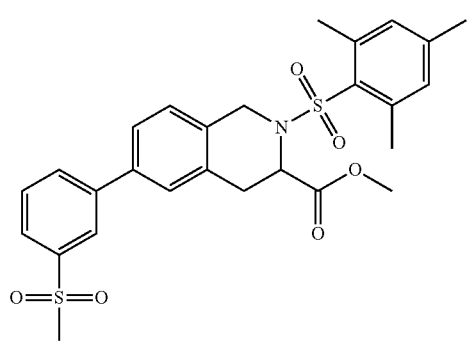

Methyl 6-bromo-2-(mesitylsulfonyl)-1,2,3,4-tetrahydroisoquinoline-3-carboxylate (0.4 g, 0.88 mmol), (3-(methylsulfonyl)phenyl)boronic acid (0.265 g, 1.33 mmol), potassium acetate (0.216 g, 2.2 mmol) and Pd(dppf)$_2$Cl$_2$·CH$_2$Cl$_2$ (0.072 g, 0.088 mmol) were taken in dioxane-water (5:1, 10 mL). The reaction mixture was heated at 60° C. for 14 h. Reaction mixture was subsequently extracted with saturated bicarbonate and brine, dried and concentrated to get the crude mixture. The crude mixture was purified on silica using ethyl acetate-hexane (30-70) to obtain the title compound (0.34 g, 73% yield). $^1$H NMR (400 MHz, DMSO-d$_6$) δ ppm 2.28 (s, 3H) 2.56 (s, 6H) 3.15-3.28 (m, 2H) 3.28 (s, 3H) 3.56 (s, 3H) 4.41-4.58 (m, 2H) 4.86 (dd, J=6.60, 2.45 Hz, 1H) 7.10 (s, 2H) 7.35 (d, J=7.83 Hz, 1H) 7.56-7.64 (m, 2H) 7.69-7.77 (m, 1H) 7.90 (d, J=7.83 Hz, 1H) 8.01 (d, J=7.58 Hz, 1H) 8.14 (s, 1H). MS (m/z): 528.1 (M+H).

Synthesis of 2-(mesitylsulfonyl)-6-(3-(methylsulfonyl)phenyl)-1,2,3,4-tetrahydroisoquinoline-3-carboxylic Acid, 4

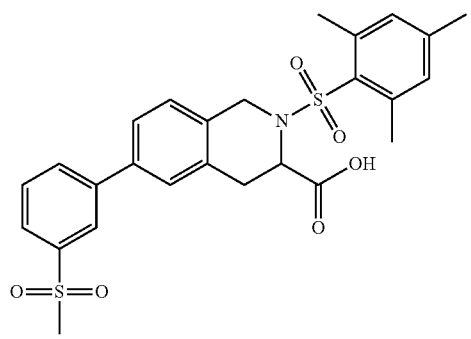

Methyl 2-(mesitylsulfonyl)-6-(3-(methylsulfonyl)phenyl)-1,2,3,4-tetrahydroisoquinoline-3-carboxylate (0.21 g, 0.38 mmol) was taken in methanol (10 mL). Lithium chloride (0.020 g, 0.76 mmol) in water (1 mL) was added to it and the reaction mixture was stirred at ambient temperature for 14 h. Crude reaction mixture was neutralized with 1N HCl. The precipitate formed was filtered and dried under reduced pressure to obtain the title compound (0.18 g, 92% yield). MS (m/z): 514.1 (M+H).

N-(4-cyanobenzyl)-2-(mesitylsulfonyl)-6-(3-(methylsulfonyl)phenyl)-1,2,3,4 tetrahydroisoquinoline-3-carboxamide, 5

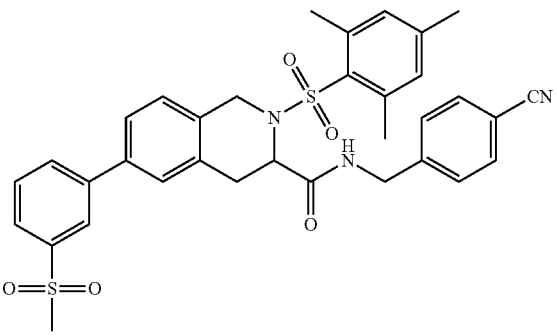

2-(mesitylsulfonyl)-6-(3-(methylsulfonyl)phenyl)-1,2,3,4-tetrahydroisoquinoline-3-carboxylic acid (0.04 g, 0.08 mmol), TBTU (0.025 g, 0.08 mmol) and Hunig's base (42 µl, 0.24 mmol) were taken in DMF (5 mL) and stirred for 30 min. 4-(aminomethyl)benzonitrile (0.013 g, 0.1 mmol) was added to the reaction and stirred for 14 h. Reaction mixture was subsequently extracted with saturated bicarbonate and brine, dried and concentrated to get the crude mixture. The crude mixture was purified on silica using ethyl acetate-hexane (40-60) to obtain the title compound (0.039 g, 77% yield). $^1$H NMR (400 MHz, DMSO-d$_6$) δ ppm 2.28 (s, 3H) 2.56 (s, 6H) 3.09-3.26 (m, 3H) 3.29 (s, 3H) 4.03 (q, J=7.09 Hz, 1H) 4.16-4.34 (m, 2H) 4.52 (d, J=15.89 Hz, 1H) 4.66 (dd, J=6.11, 3.18 Hz, 1H) 4.76 (d, J=16.14 Hz, 1H) 7.09 (s, 2H) 7.23 (d, J=8.31 Hz, 2H) 7.34 (d, J=7.82 Hz, 1H)

7.56-7.62 (m, 2H) 7.64-7.69 (m, 2H) 7.70-7.78 (m, 1H) 7.87-7.93 (m, 1H) 8.02 (d, J=7.82 Hz, 1H) 8.14 (t, J=1.71 Hz, 1H) 8.58 (t, J=5.87 Hz, 1H). MS (m/z): 628.1 (M+H).

Compounds of Type H:

Synthesis of 2,4,6-trimethyl-N-(6-(4-(methylsulfonyl)phenyl)quinolin-2-yl)benzenesulfonamide 6

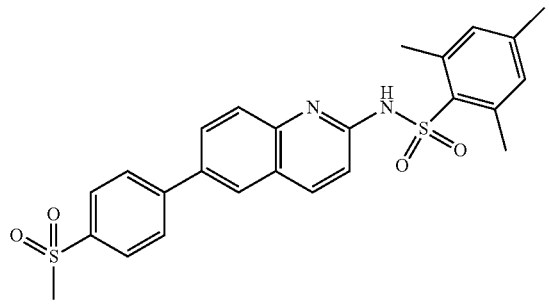

Step 1—Synthesis of N-(6-bromoquinolin-2-yl)-2,4,6-trimethylbenzenesulfonamide

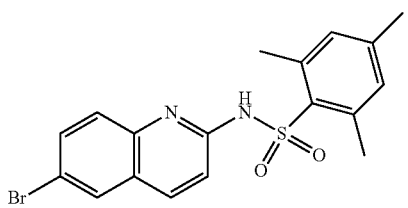 [SMILES: Cc1cc(C)c(S(=O)(=O)Nc2ccc3cc(Br)ccc3n2)c(C)c1]

To a solution of 2-amino-6-bromoquinoline (250 mg, 1.12 mmol, 1 eq.) in anhydrous acetonitrile (1.0 mL) was added DMAP (342 mg, 2.8 mmol, 3 eq.) and the resulting mixture was stirred at rt for 5 min. To this mixture was added 2,4,6-trimethylbenzenesulfonyl chloride (245 mg, 1.12 mmol, 1.0 eq). The reaction was stirred at rt for 2 h then heated to 70° C. for 12 h. The reaction was judged finished by HPLC. The solvent was then removed by passing a stream of air over the top of the vessel. Water was then added and the mixture was extracted with EtOAc (3×). The organics were combined, washed with brine, dried in vacuo. The crude material was purified by reverse phase chromatography (60 g C18 column, eluent H$_2$O—CH$_3$CN; 100% to 5-95%) to give the desired products. 1H-NMR (400 MHz, CDCl$_3$) δ 7.76-7.73 (m, 3H), 7.72 (s, 1H), 7.67 (dd, J=8.0, 2.0 Hz, 1H), 7.31 (d, J=8.0 Hz); 6.94 (m, 2H), 6.83 (d, J=8.0 Hz), 2.71 (s, 6H), 2.30 (s, 3H); LC/MS m/z calc M 404.2; obs M+H 405.0.

Step 2—Synthesis of 2,4,6-trimethyl-N-(6-(4-(methylsulfonyl)phenyl)quinolin-2-yl)benzenesulfonamide 6

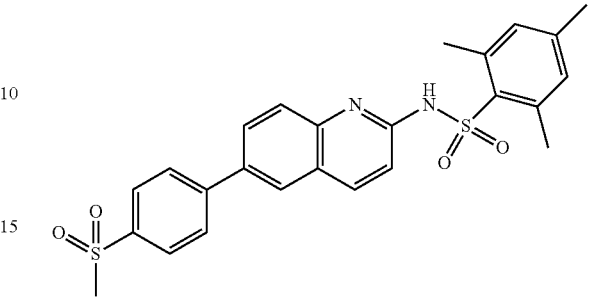

To a solution of the above sulfonamide (60 mg, 0.148 mmol, 1 eq.) in anhydrous DMF (1.0 mL) was added (4-(methylsulfonyl)phenyl)boronic acid (33 mg, 0.163 mmol, 1.1 eq.) and a 2.0M solution of Cs$_2$CO$_3$ (0.370 mL, 0.740 mmol, 5 eq.). The resulting mixture was degassed and backfilled with argon. To the degassed solution was added Pd(PPh$_3$)$_4$ (9.0 mg, 0.0074 mmol, 0.05 eq.) and the reaction was heated to 70° C. for 2.5. When the reaction was judged complete it was allowed to cool to rt, quenched with water and extracted with ethyl acetate (3×). The organics were combined, washed with brine, dried and concentrated in vacuo. The resulting crude material was purified by flash column chromatography on a 12 g silica cartridge. Eluting with Hexanes-EtOAc (100:0 to 60:40) gave the desired product. 1H-NMR (400 MHz, CDCl$_3$) δ 8.06 (m, 2H), 7.90 (d, J=8.6 Hz, 1H), 7.87-7.79 (m, 4H), 7.72 (s, 1H), 7.67 (dd, J=8.0, 2.0 Hz, 1H), 6.96 (m, 2H), 6.90 (d, J=8.6 Hz), 3.12 (S, 3H), 2.75 (s, 6H), 2.29 (s, 3H); LC/MS m/z calc M 480.1; obs M+H 481.0.

Synthesis of N-(6-(3-methoxyphenyl)quinolin-2-yl)-2,4,6-trimethylbenzenesulfonamide, 7

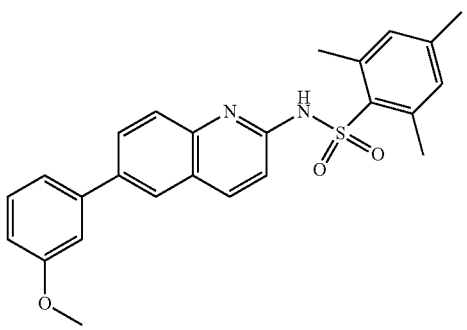 [SMILES: COc1cccc(-c2ccc3nc(NS(=O)(=O)c4c(C)cc(C)cc4C)ccc3c2)c1]

Compound 7 was prepared in a manner analogous to example 6 above. Purification by flash chromatography eluting with hexanes-EtOAc (100:0 to 70:30) gave the desired product. 1H-NMR (400 MHz, CDCl$_3$) δ 7.87 (d, J=8.6 Hz, 1H), 7.80 (dd, J=8.2, 2.0 Hz, 1H), 7.75 (d, J=2.0 Hz, 1H), 7.43 (d, J=8.6 Hz, 1H), 7.37-7.32 (m, 2H), 7.09-7.00 (m, 2H), 6.84 (d, J=8.6 Hz, 1H), 3.92 (s, 3H), 2.73 (s, 6H), 2.28 (s, 3H); LC/MS m/z calc M 432.2; obs M+H 433.1.

Synthesis of 2,4,6-trimethyl-N-(6-(1-methyl-1H-pyrazol-5-yl)quinolin-2-yl)benzenesulfonamide

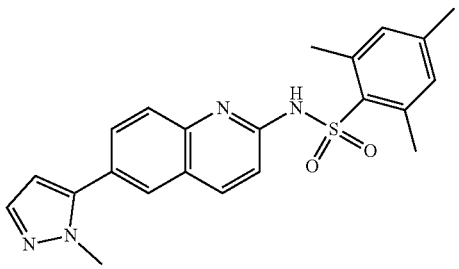 [SMILES: Cc1cc(C)c(S(=O)(=O)Nc2ccc3cc(-c4ccnn4C)ccc3n2)c(C)c1]

Compound 8 was prepared in a manner analogous to example 6 above. Purification by flash chromatography eluting with hexanes-EtOAc (100:0 to 30:70) gave the desired product. MHz 1H-NMR (400 MHz, CDCl$_3$) δ 7.90 (d, J=8.6 Hz, 1H), 7.69-7.66 (m, 2H), 7.56-7.54 (m, 2H), 6.96 (m, 3H), 6.35 (d, J=2.0 Hz, 1H), 3.96 (s, 3H), 2.74 (s, 6H), 2.29 (s, 3H); LC/MS m/z calc M 406.2; obs M+H 407.1.

Synthesis of tert-butyl (3-(2-((2,4,6-trimethylphenyl)sulfonamido)quinolin-6-yl)benzyl)carbamate

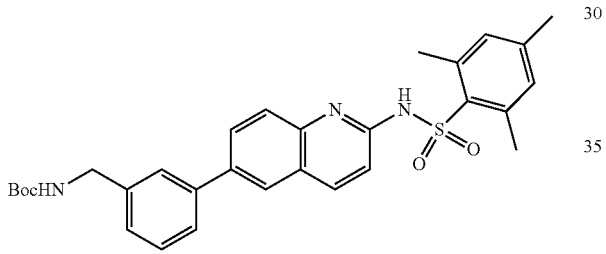

Compound 9 was prepared in a manner analogous to example 6 above. Purification by flash chromatography eluting with hexanes-EtOAc (100:0 to 60:40) gave the desired product. 1H-NMR (400 MHz, CDCl$_3$) δ 7.87 (d, J=9.2 Hz, 1H), 7.83 (dd, J=8.4, 2.0, 1H), 7.90-7.80 (m, 1H), 7.54-7.42 (m, 3H), 7.32-7.30 (m, 1H), 6.94 (m, 2H), 6.86 (d, J=9.2 Hz, 1H), 4.89 (s, 1H), 4.35 (m, 2H), 2.74 (s, 6H), 2.80 (s, 3H), 1.48 (s, 9H); LC/MS m/z calc M 530.1; obs M+H 531.1.

Synthesis of N-(6-(3-(aminomethyl)phenylquinolin-2-yl)-2,4,6-trimethylbenzenesulfonamide-hydrochloride Salt

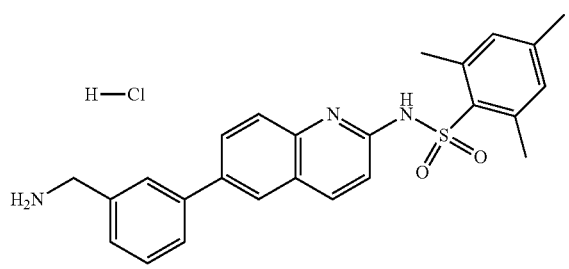 [SMILES: Cc1cc(C)c(S(=O)(=O)Nc2ccc3cc(-c4cccc(CN)c4)ccc3n2)c(C)c1 ; Cl]

Compound 9 (20 mg, 0.037 mmol, 1 eq.) from above was stirred at rt in a solution of 4N HCl-Dioxane (0.1 mL, 0.4 mmol, 10 eq.). The dioxane was removed by passing a stream of air over the reaction vial. The resulting residue was then slurried in MeOH and filtered to give the desired product in >95% purity. 1H-NMR (400 MHz, DMSOd$_6$) δ 8.40-8.30 (br s, 2H), 8.25 (d, J=9.2 Hz, 1H), 8.15 (m, 1H), 8.0 (m, 1H), 7.75 (d, J=8.4, 2H), 7.61-7.51 (m, 3H), 7.25-7.15 (br s, 1H), 7.54-7.42 (m, 3H), 6.94 (m, 2H), 4.15 (m, 2H), 2.74 (s, 6H), 2.25 (s, 3H), LC/MS m/z calc M 431.2; obs M+H 432.1.

Compounds of Type I:

Synthesis of 3,4-dimethyl-N-(6-(3-(methylsulfonyl)phenyl)quinolin-2-yl)benzamide

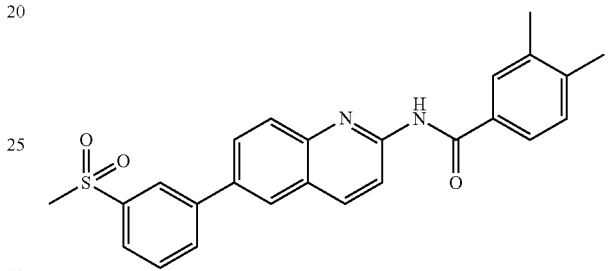

Step 1 Synthesis of N-(6-bromoquinolin-2-yl)-3,4-dimethylbenzamide

A suspension of 2-amino-6-bromoquinoline (50 mg, 0.224 mmol, 1 eq.) in anhydrous acetonitrile (1.0 mL) was treated with DMAP (36 mg, 0.291 mmol, 1.3 eq.) at rt. To this mixture was added 3,4-dimethylbenzoyl chloride (41 mg, 0.246 mmol, 1.1 eq.) which resulted in a homogeneous solution. The reaction was stirred at rt overnight. The reaction was judged complete by HPLC and quenched with addition of water. The aqueous solution was extracted with ethyl acetate (3×) and the organics were combined, washed with brine, dried and concentrated in vacuo. The crude material was purified by flash column chromatography on a 12 g silica cartridge. Elution with hexanes-ethyl acetate (100:0 to 60:40) led to isolation of the desired product. 1H-NMR (400 MHz, DMSO-d$_6$) δ 11.02 (s, 1H), 8.40-8.36 (m, 2H), 8.23 (d, J=2.0 Hz, 1H), 7.91 (d, J=2.0 Hz, 1H) 7.86-7.78 (m, 3H), 7.28 (d, J=8.0 Hz, 1H), 2.31 (s, 6H); LC/MS m/z calc M 354.0 & 356.0; obs (M+H) 355.0 & 357.0 for bromine.

Step 2—Synthesis of Synthesis of 3,4-dimethyl-N-(6-(3-(methylsulfonyl)phenyl)quinolin-2-yl)benzamide, X

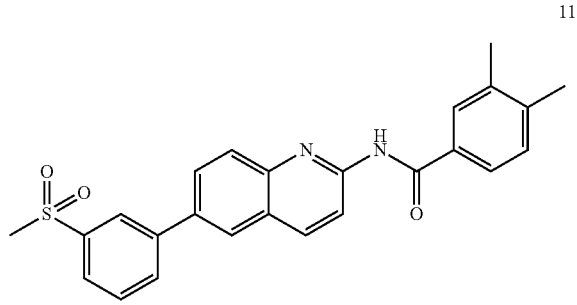

To a solution of N-(6-bromoquinolin-2-yl)-3,4-dimethyl-benzamide (40 mg, 0.11 mmol, 1 eq.) in anhydrous dioxane (1 mL) was added $Cs_2CO_3$ (55 mg, 0.16 mmol, 1.4 eq.) and the boronic acid (25 mg, 0.12 mmol, 1.1 eq.) at rt. The reaction suspension was then degassed and back filled with argon. To the reaction was then added $Pd(dppf)_2$-DCM (10 mg, 0.01 mmol, 0.1 eq.) which was then heated to 75° C. overnight. The reaction was judged complete by HPLC and quenched with water and extracted with ethyl acetate (3×). The combined organics were washed with brine, dried and concentrated in vacuo. The crude material was purified by flash column chromatography on a 12 g silica cartridge. Elution with hexanes-ethyl acetate (100:0 to 60:40) led to isolation of the desired product. 1H-NMR (400 MHz, DMSO-$d_6$) δ 11.05 (s, 1H), 8.51 (d, J=8.0, 2H), 8.48-8.35 (m, 3H), 8.21-8.15 (m, 2H), 8.0-7.91 (m, 3H) 7.81-7.75 (m, 2H), 7.25 (d, J=8.0 Hz, 1H), 2.35 (s, 6H); LC/MS m/z calc M 430.1; obs (M+H) 431.1.

TABLE 1

LXRa activity for selected compounds in the Lantha Screen

| Compound # | LXRα $IC_{50}$ (μM) |
|---|---|
| 38 | 0.661 |
| 12 | 0.02 |
| 3 | 5.0 |
| 104 | 4.3 |
| 113 | 5.2 |
| 5 | 8.3 |
| 14 | 2.1 |

TABLE 2

Additional Examples of Compounds according to formula I

| Example Number | Structure | MS (m/z): (M + H). |
|---|---|---|
| 12 | 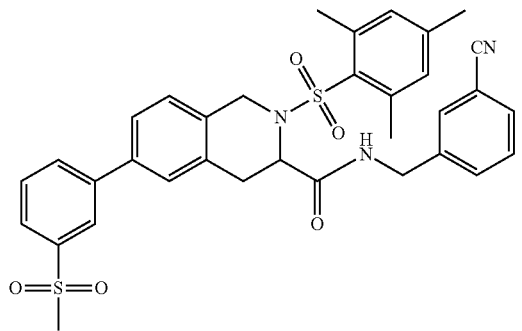 [SMILES: Cc1cc(C)c(S(=O)(=O)N2Cc3ccc(-c4cccc(S(C)(=O)=O)c4)cc3CC2C(=O)NCc2cccc(C#N)c2)c(C)c1] | 628.1 |
| 13 | 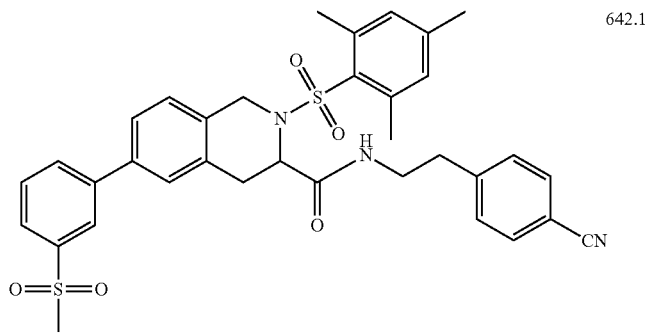 | 642.1 |

TABLE 2-continued

Additional Examples of Compounds according to formula I

| Example Number | Structure | MS (m/z): (M + H). |
|---|---|---|
| 14 | 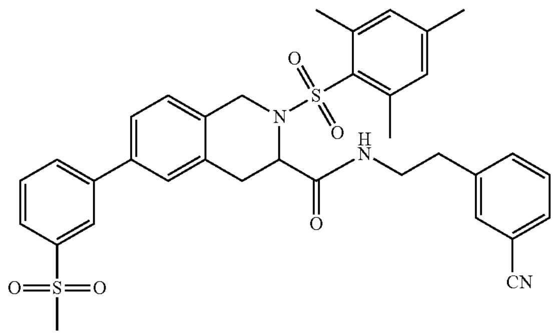 [SMILES: Cc1cc(C)c(S(=O)(=O)N2Cc3ccc(-c4cccc(S(C)(=O)=O)c4)cc3CC2C(=O)NCCc2cccc(C#N)c2)c(C)c1] | 642.1 |
| 15 | 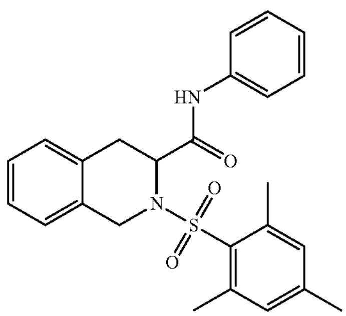 [SMILES: Cc1cc(C)c(S(=O)(=O)N2Cc3ccccc3CC2C(=O)Nc2ccccc2)c(C)c1] | 435.1 |
| 16 | 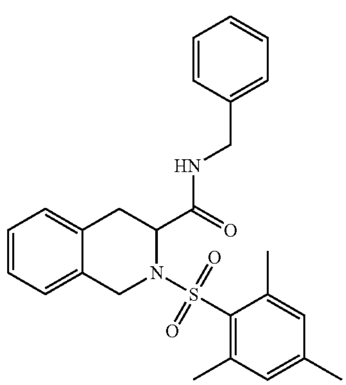 [SMILES: Cc1cc(C)c(S(=O)(=O)N2Cc3ccccc3CC2C(=O)NCc2ccccc2)c(C)c1] | 449.1 |
| 17 | 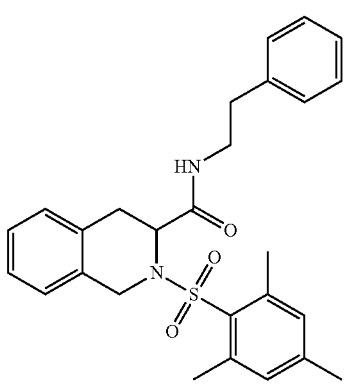 [SMILES: Cc1cc(C)c(S(=O)(=O)N2Cc3ccccc3CC2C(=O)NCCc2ccccc2)c(C)c1] | 463.1 |

TABLE 2-continued

Additional Examples of Compounds according to formula I

| Example Number | Structure | MS (m/z): (M + H). |
|---|---|---|
| 18 | 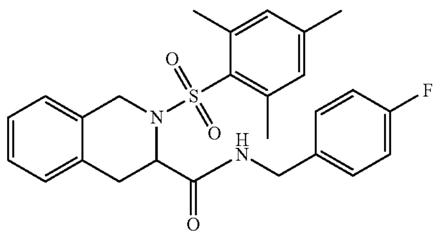 [SMILES: Cc1cc(C)c(S(=O)(=O)N2Cc3ccccc3CC2C(=O)NCc2ccc(F)cc2)c(C)c1] | 467.1 |
| 19 | 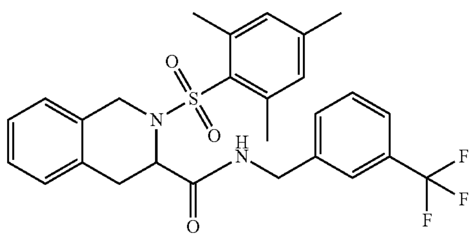 [SMILES: Cc1cc(C)c(S(=O)(=O)N2Cc3ccccc3CC2C(=O)NCc2cccc(C(F)(F)F)c2)c(C)c1] | 517.1 |
| 20 | 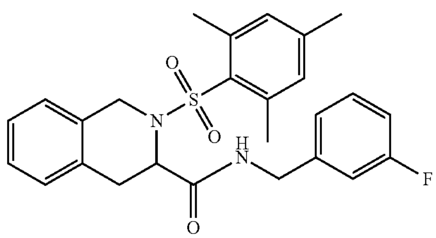 [SMILES: Cc1cc(C)c(S(=O)(=O)N2Cc3ccccc3CC2C(=O)NCc2cccc(F)c2)c(C)c1] | 467.1 |
| 21 | 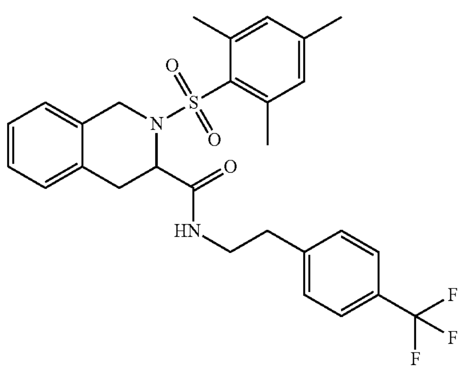 [SMILES: Cc1cc(C)c(S(=O)(=O)N2Cc3ccccc3CC2C(=O)NCCc2ccc(C(F)(F)F)cc2)c(C)c1] | 531.1 |
| 22 | 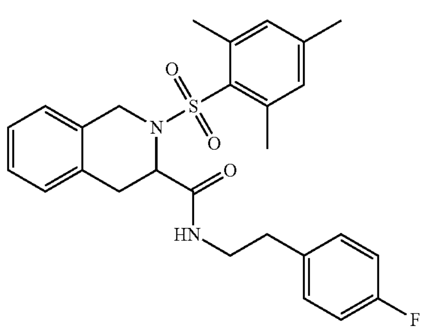 [SMILES: Cc1cc(C)c(S(=O)(=O)N2Cc3ccccc3CC2C(=O)NCCc2ccc(F)cc2)c(C)c1] | 481.1 |

TABLE 2-continued

Additional Examples of Compounds according to formula I

| Example Number | Structure | MS (m/z): (M + H). |
|---|---|---|
| 23 | 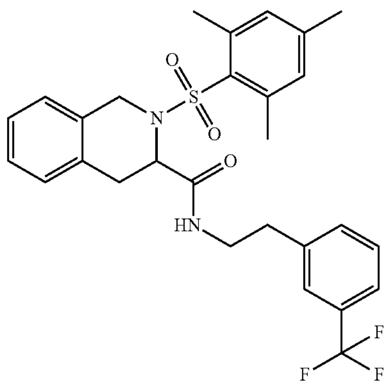 [SMILES: Cc1cc(C)c(S(=O)(=O)N2Cc3ccccc3CC2C(=O)NCCc2cccc(C(F)(F)F)c2)c(C)c1] | 531.1 |
| 24 | 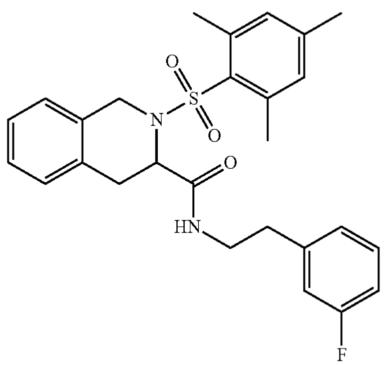 [SMILES: Cc1cc(C)c(S(=O)(=O)N2Cc3ccccc3CC2C(=O)NCCc2cccc(F)c2)c(C)c1] | 481.1 |
| 25 | 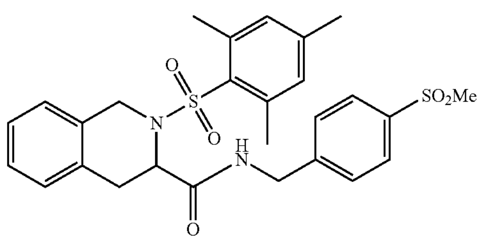 [SMILES: Cc1cc(C)c(S(=O)(=O)N2Cc3ccccc3CC2C(=O)NCc2ccc(S(C)(=O)=O)cc2)c(C)c1] | 527.1 |
| 26 | 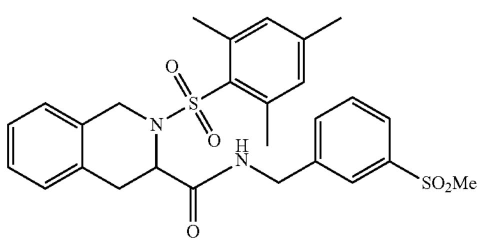 [SMILES: Cc1cc(C)c(S(=O)(=O)N2Cc3ccccc3CC2C(=O)NCc2cccc(S(C)(=O)=O)c2)c(C)c1] | 527.1 |
| 27 | 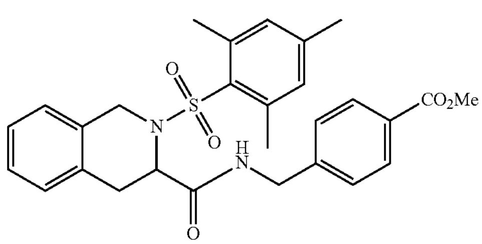 [SMILES: COC(=O)c1ccc(CNC(=O)C2Cc3ccccc3CN2S(=O)(=O)c2c(C)cc(C)cc2C)cc1] | 507.1 |

TABLE 2-continued
Additional Examples of Compounds according to formula I
| Example Number | Structure | MS (m/z): (M + H). |
|---|---|---|
| 28 | 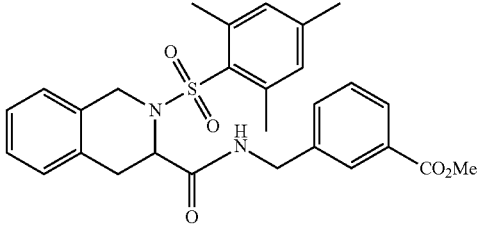 [SMILES: COC(=O)c1cccc(CNC(=O)C2Cc3ccccc3CN2S(=O)(=O)c2c(C)cc(C)cc2C)c1] | 507.1 |
| 29 | 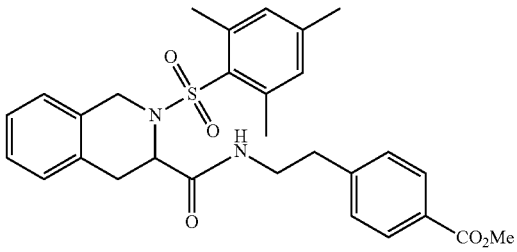 [SMILES: COC(=O)c1ccc(CCNC(=O)C2Cc3ccccc3CN2S(=O)(=O)c2c(C)cc(C)cc2C)cc1] | 521.1 |
| 30 | 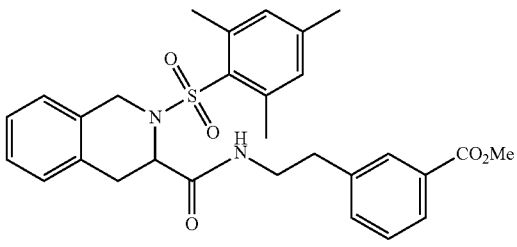 [SMILES: COC(=O)c1cccc(CCNC(=O)C2Cc3ccccc3CN2S(=O)(=O)c2c(C)cc(C)cc2C)c1] | 521.1 |
| 31 | 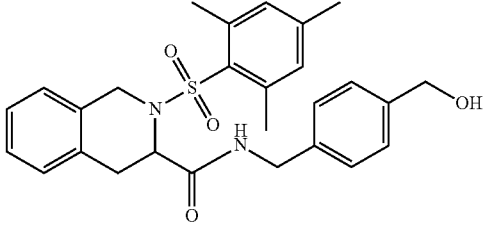 [SMILES: Cc1cc(C)c(S(=O)(=O)N2Cc3ccccc3CC2C(=O)NCc2ccc(CO)cc2)c(C)c1] | 479.1 |
| 32 | 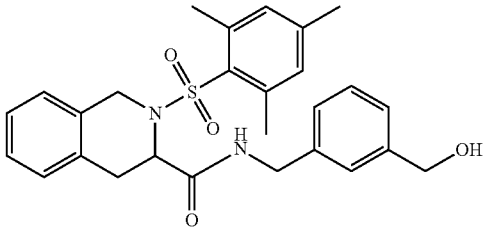 [SMILES: Cc1cc(C)c(S(=O)(=O)N2Cc3ccccc3CC2C(=O)NCc2cccc(CO)c2)c(C)c1] | 479.1 |
| 33 | 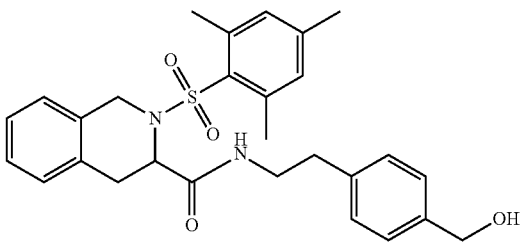 [SMILES: Cc1cc(C)c(S(=O)(=O)N2Cc3ccccc3CC2C(=O)NCCc2ccc(CO)cc2)c(C)c1] | 493.1 |

TABLE 2-continued
Additional Examples of Compounds according to formula I
| Example Number | Structure | MS (m/z): (M + H). |
|---|---|---|
| 34 | 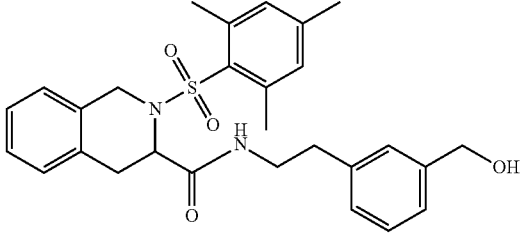 [SMILES: Cc1cc(C)c(S(=O)(=O)N2Cc3ccccc3CC2C(=O)NCCc2cccc(CO)c2)c(C)c1] | 493.1 |
| 35 | 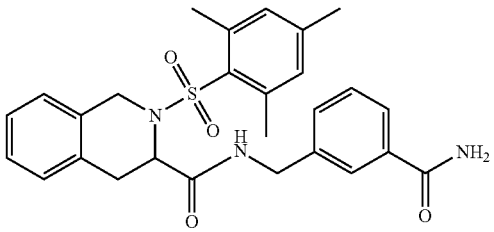 [SMILES: Cc1cc(C)c(S(=O)(=O)N2Cc3ccccc3CC2C(=O)NCc2cccc(C(N)=O)c2)c(C)c1] | 492.1 |
| 36 | 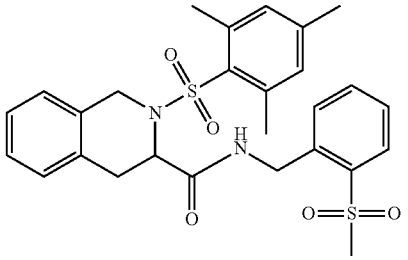 [SMILES: Cc1cc(C)c(S(=O)(=O)N2Cc3ccccc3CC2C(=O)NCc2ccccc2S(C)(=O)=O)c(C)c1] | 527.1 |
| 37 | 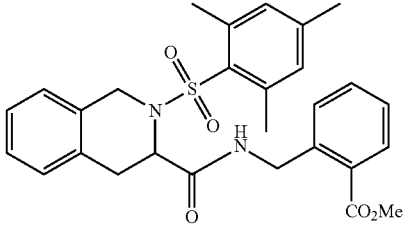 [SMILES: COC(=O)c1ccccc1CNC(=O)C1Cc2ccccc2CN1S(=O)(=O)c1c(C)cc(C)cc1C] | 507.1 |
| 38 | 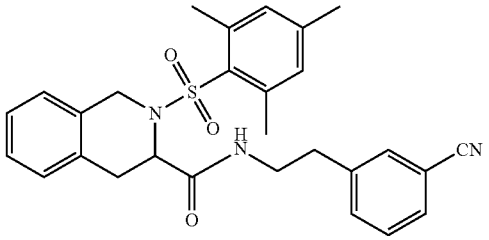 [SMILES: Cc1cc(C)c(S(=O)(=O)N2Cc3ccccc3CC2C(=O)NCCc2cccc(C#N)c2)c(C)c1] | 488.1 |
| 39 | 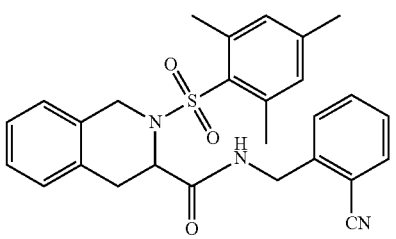 [SMILES: Cc1cc(C)c(S(=O)(=O)N2Cc3ccccc3CC2C(=O)NCc2ccccc2C#N)c(C)c1] | 474.1 |

TABLE 2-continued

Additional Examples of Compounds according to formula I

| Example Number | Structure | MS (m/z): (M + H). |
|---|---|---|
| 40 | 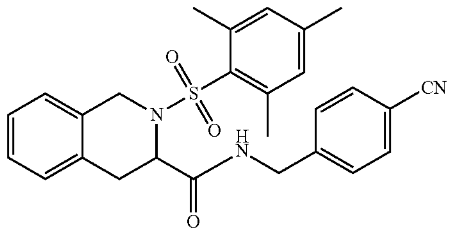 [SMILES: Cc1cc(C)c(S(=O)(=O)N2Cc3ccccc3CC2C(=O)NCc2ccc(C#N)cc2)c(C)c1] | 474.1 |
| 41 | 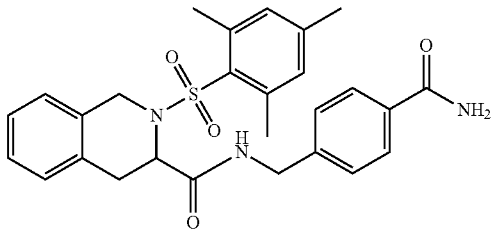 [SMILES: Cc1cc(C)c(S(=O)(=O)N2Cc3ccccc3CC2C(=O)NCc2ccc(C(N)=O)cc2)c(C)c1] | 492.1 |
| 42 | 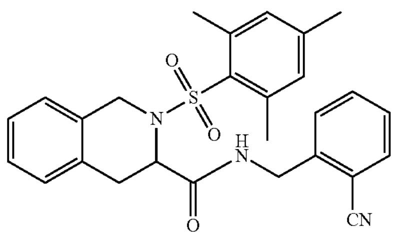 [SMILES: Cc1cc(C)c(S(=O)(=O)N2Cc3ccccc3CC2C(=O)NCc2ccccc2C#N)c(C)c1] | 474.1 |
| 43 | 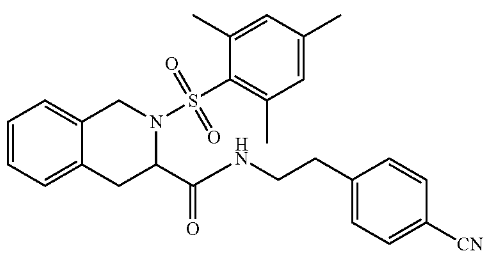 [SMILES: Cc1cc(C)c(S(=O)(=O)N2Cc3ccccc3CC2C(=O)NCCc2ccc(C#N)cc2)c(C)c1] | 488.1 |
| 44 | 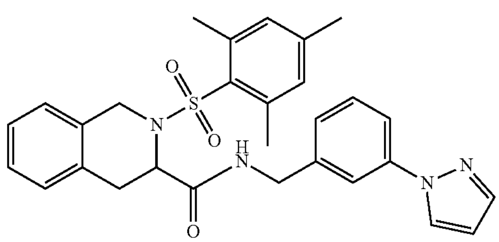 [SMILES: Cc1cc(C)c(S(=O)(=O)N2Cc3ccccc3CC2C(=O)NCc2cccc(-n3cccn3)c2)c(C)c1] | 515.1 |
| 45 | 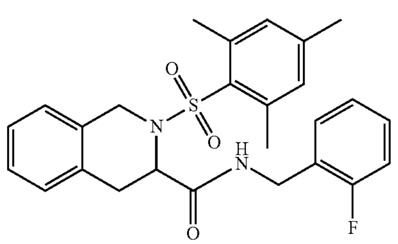 [SMILES: Cc1cc(C)c(S(=O)(=O)N2Cc3ccccc3CC2C(=O)NCc2ccccc2F)c(C)c1] | 467.1 |

TABLE 2-continued

Additional Examples of Compounds according to formula I

| Example Number | Structure | MS (m/z): (M + H). |
|---|---|---|
| 46 | 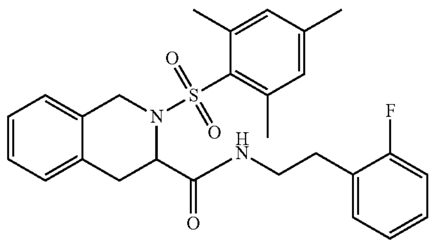 [SMILES: Cc1cc(C)c(S(=O)(=O)N2Cc3ccccc3CC2C(=O)NCCc2ccccc2F)c(C)c1] | 481.1 |
| 47 | 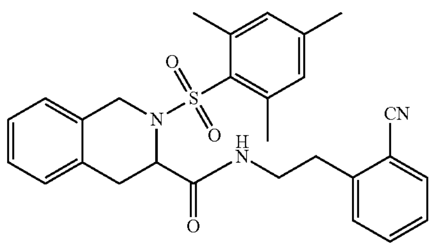 [SMILES: Cc1cc(C)c(S(=O)(=O)N2Cc3ccccc3CC2C(=O)NCCc2ccccc2C#N)c(C)c1] | 488.1 |
| 48 | 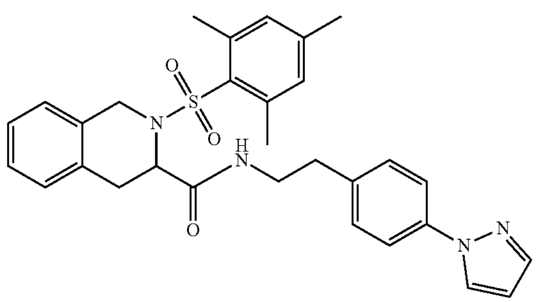 [SMILES: Cc1cc(C)c(S(=O)(=O)N2Cc3ccccc3CC2C(=O)NCCc2ccc(-n3cccn3)cc2)c(C)c1] | 529.1 |
| 49 | 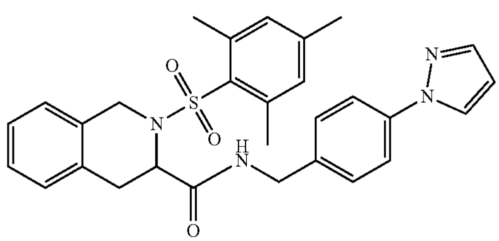 [SMILES: Cc1cc(C)c(S(=O)(=O)N2Cc3ccccc3CC2C(=O)NCc2ccc(-n3cccn3)cc2)c(C)c1] | 515.1 |
| 50 | 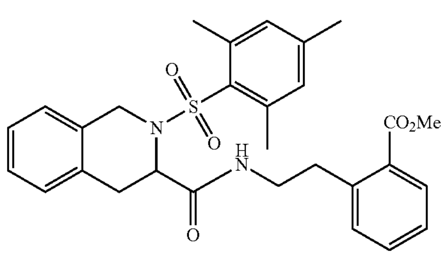 [SMILES: COC(=O)c1ccccc1CCNC(=O)C1Cc2ccccc2CN1S(=O)(=O)c1c(C)cc(C)cc1C] | 521.1 |

TABLE 2-continued

Additional Examples of Compounds according to formula I

| Example Number | Structure | MS (m/z): (M + H). |
|---|---|---|
| 51 | 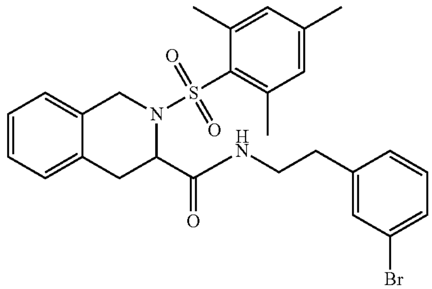 [SMILES: Cc1cc(C)c(S(=O)(=O)N2Cc3ccccc3CC2C(=O)NCCc2cccc(Br)c2)c(C)c1] | 541.1, 543.1 |
| 52 | 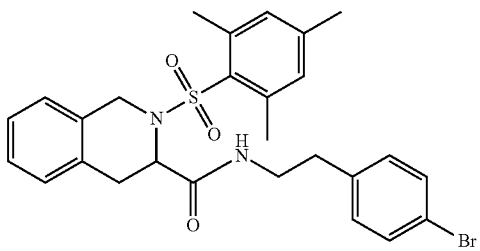 [SMILES: Cc1cc(C)c(S(=O)(=O)N2Cc3ccccc3CC2C(=O)NCCc2ccc(Br)cc2)c(C)c1] | 541.1, 543.1 |
| 53 | 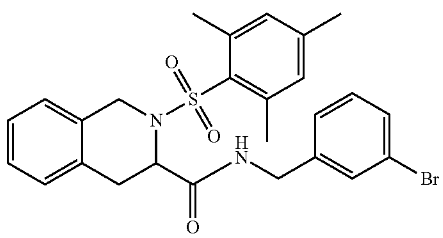 [SMILES: Cc1cc(C)c(S(=O)(=O)N2Cc3ccccc3CC2C(=O)NCc2cccc(Br)c2)c(C)c1] | 527.0, 529.0 |
| 54 | 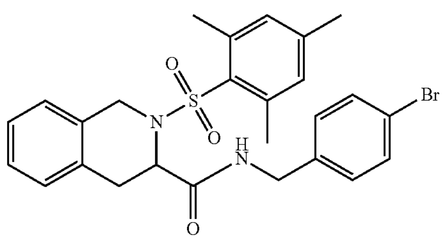 [SMILES: Cc1cc(C)c(S(=O)(=O)N2Cc3ccccc3CC2C(=O)NCc2ccc(Br)cc2)c(C)c1] | 527.1, 529.1 |
| 55 | 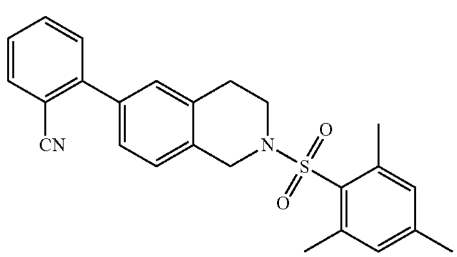 [SMILES: Cc1cc(C)c(S(=O)(=O)N2CCc3cc(-c4ccccc4C#N)ccc3C2)c(C)c1] | 417.1 |
| 56 | 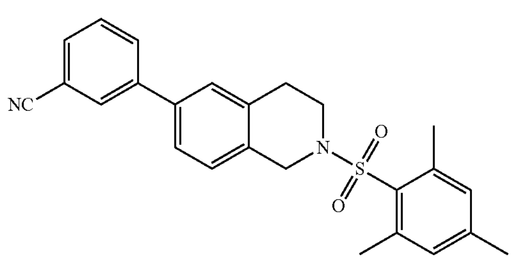 [SMILES: Cc1cc(C)c(S(=O)(=O)N2CCc3cc(-c4cccc(C#N)c4)ccc3C2)c(C)c1] | 417.1 |

TABLE 2-continued

Additional Examples of Compounds according to formula I

| Example Number | Structure | MS (m/z): (M + H). |
|---|---|---|
| 57 | 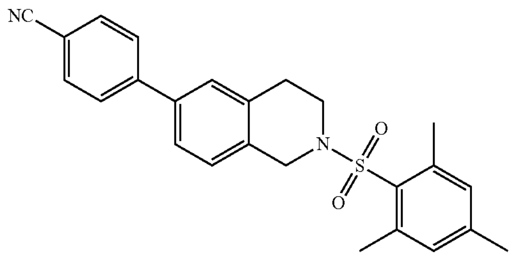 [SMILES: Cc1cc(C)c(S(=O)(=O)N2CCc3cc(-c4ccc(C#N)cc4)ccc3C2)c(C)c1] | 417.1 |
| 58 | 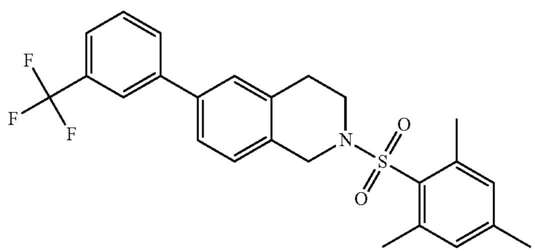 [SMILES: Cc1cc(C)c(S(=O)(=O)N2CCc3cc(-c4cccc(C(F)(F)F)c4)ccc3C2)c(C)c1] | 460.1 |
| 59 | 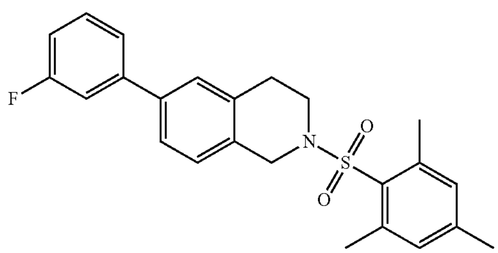 [SMILES: Cc1cc(C)c(S(=O)(=O)N2CCc3cc(-c4cccc(F)c4)ccc3C2)c(C)c1] | 410.1 |
| 60 | 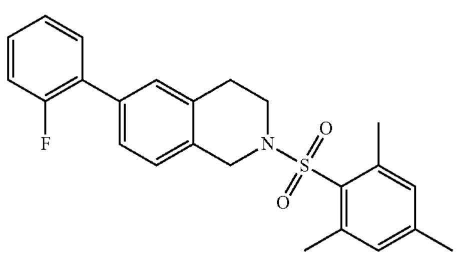 [SMILES: Cc1cc(C)c(S(=O)(=O)N2CCc3cc(-c4ccccc4F)ccc3C2)c(C)c1] | 410.1 |
| 61 | 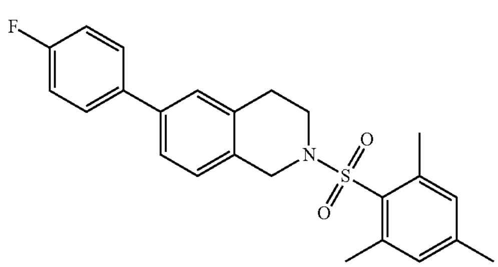 [SMILES: Cc1cc(C)c(S(=O)(=O)N2CCc3cc(-c4ccc(F)cc4)ccc3C2)c(C)c1] | 410.1 |

TABLE 2-continued

Additional Examples of Compounds according to formula I

| Example Number | Structure | MS (m/z): (M + H) |
|---|---|---|
| 62 | 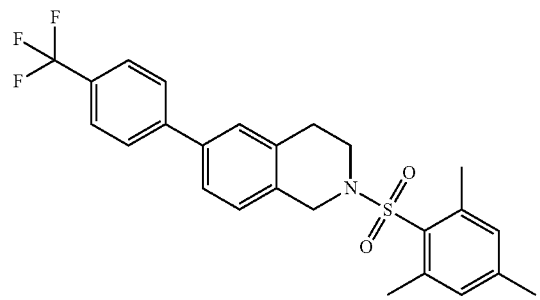 [SMILES: Cc1cc(C)c(S(=O)(=O)N2CCc3cc(-c4ccc(C(F)(F)F)cc4)ccc3C2)c(C)c1] | 460.1 |
| 63 | 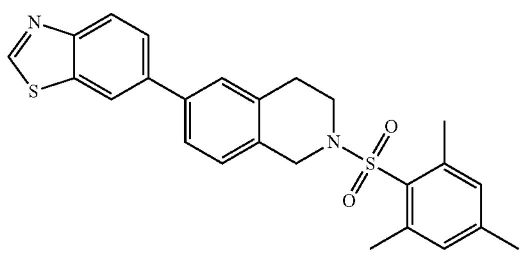 [SMILES: Cc1cc(C)c(S(=O)(=O)N2CCc3cc(-c4ccc5ncsc5c4)ccc3C2)c(C)c1] | 449.1 |
| 64 | 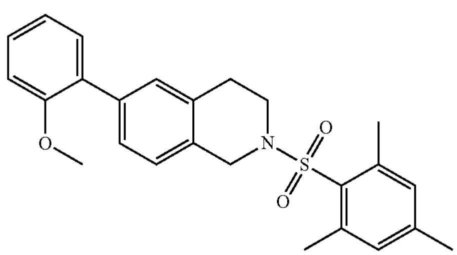 [SMILES: COc1ccccc1-c1ccc2c(c1)CCN(S(=O)(=O)c1c(C)cc(C)cc1C)C2] | 422.1 |
| 65 | 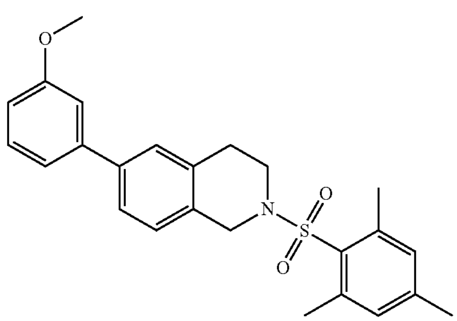 [SMILES: COc1cccc(-c2ccc3c(c2)CCN(S(=O)(=O)c2c(C)cc(C)cc2C)C3)c1] | 422.1 |
| 66 | 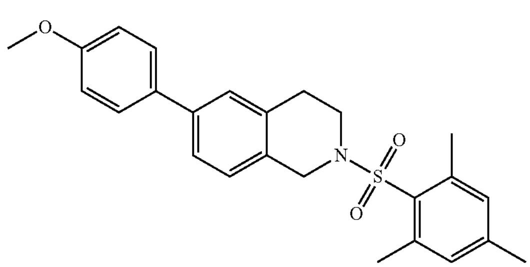 | 422.1 |

TABLE 2-continued

Additional Examples of Compounds according to formula I

| Example Number | Structure | MS (m/z): (M + H). |
|---|---|---|
| 67 | 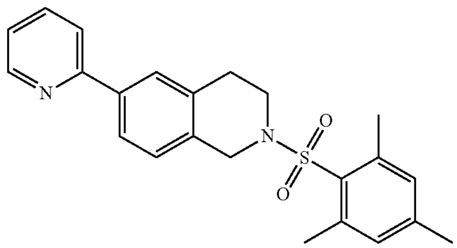 [SMILES: Cc1cc(C)c(S(=O)(=O)N2CCc3cc(-c4ccccn4)ccc3C2)c(C)c1] | 393.1 |
| 68 | 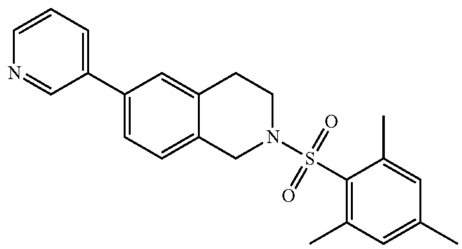 [SMILES: Cc1cc(C)c(S(=O)(=O)N2CCc3cc(-c4cccnc4)ccc3C2)c(C)c1] | 393.1 |
| 69 | 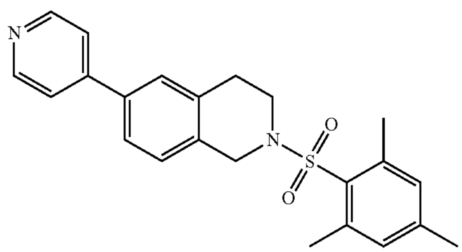 [SMILES: Cc1cc(C)c(S(=O)(=O)N2CCc3cc(-c4ccncc4)ccc3C2)c(C)c1] | 393.1 |
| 70 | 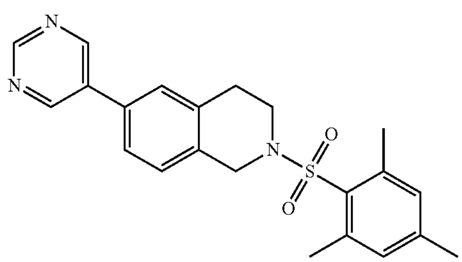 [SMILES: Cc1cc(C)c(S(=O)(=O)N2CCc3cc(-c4cncnc4)ccc3C2)c(C)c1] | 394.1 |
| 71 | 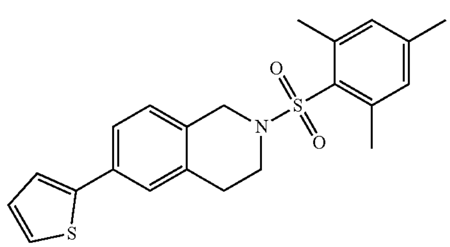 [SMILES: Cc1cc(C)c(S(=O)(=O)N2CCc3cc(-c4cccs4)ccc3C2)c(C)c1] | 398.0 |
| 72 | 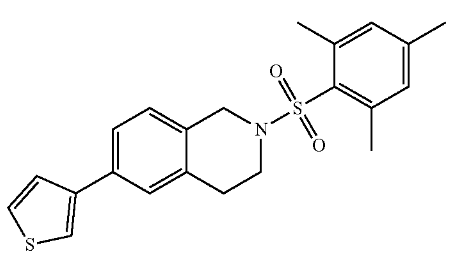 [SMILES: Cc1cc(C)c(S(=O)(=O)N2CCc3cc(-c4ccsc4)ccc3C2)c(C)c1] | 398.1 |

TABLE 2-continued

Additional Examples of Compounds according to formula I

| Example Number | Structure | MS (m/z): (M + H). |
|---|---|---|
| 73 | 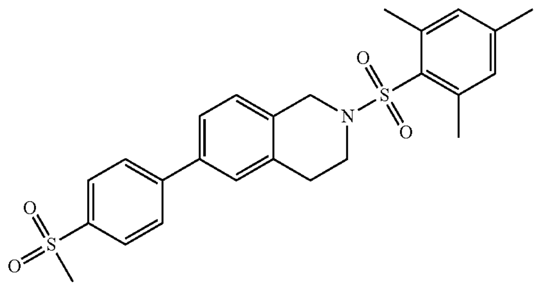 [SMILES: Cc1cc(C)c(S(=O)(=O)N2CCc3cc(-c4ccc(S(C)(=O)=O)cc4)ccc3C2)c(C)c1] | 470.1 |
| 74 | 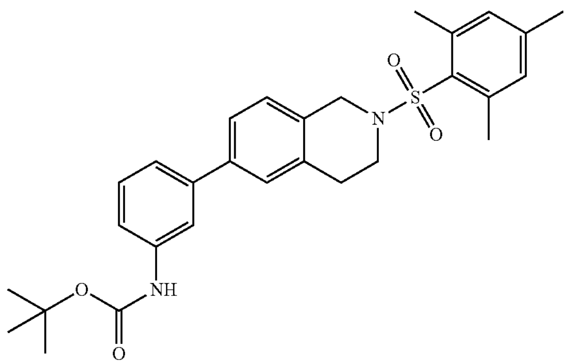 [SMILES: Cc1cc(C)c(S(=O)(=O)N2CCc3cc(-c4cccc(NC(=O)OC(C)(C)C)c4)ccc3C2)c(C)c1] | 507.2 |
| 75 | 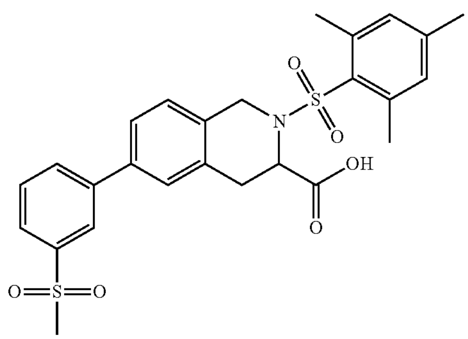 [SMILES: Cc1cc(C)c(S(=O)(=O)N2Cc3ccc(-c4cccc(S(C)(=O)=O)c4)cc3CC2C(=O)O)c(C)c1] | 514.1 |
| 76 | 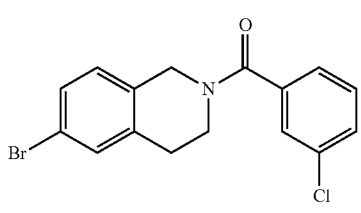 [SMILES: O=C(c1cccc(Cl)c1)N1CCc2cc(Br)ccc2C1] | 349.9, 351.9 |
| 77 | 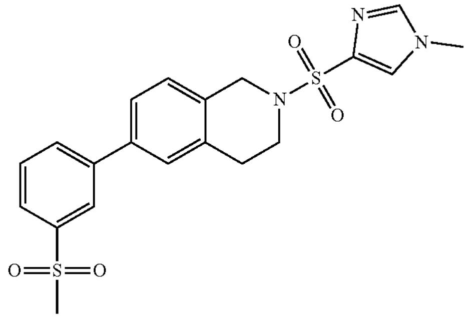 [SMILES: Cn1cnc(S(=O)(=O)N2CCc3cc(-c4cccc(S(C)(=O)=O)c4)ccc3C2)c1] | 432.0 |

TABLE 2-continued

Additional Examples of Compounds according to formula I

| Example Number | Structure | MS (m/z): (M + H). |
|---|---|---|
| 78 | 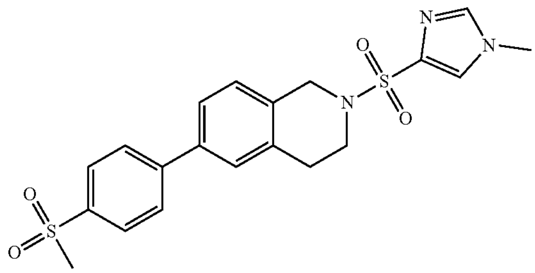 [SMILES: Cn1cnc(S(=O)(=O)N2CCc3cc(-c4ccc(S(C)(=O)=O)cc4)ccc3C2)c1] | 432.0 |
| 79 | 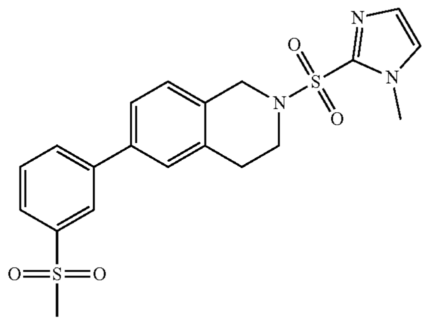 [SMILES: Cn1ccnc1S(=O)(=O)N1CCc2cc(-c3cccc(S(C)(=O)=O)c3)ccc2C1] | 432.0 |
| 80 | 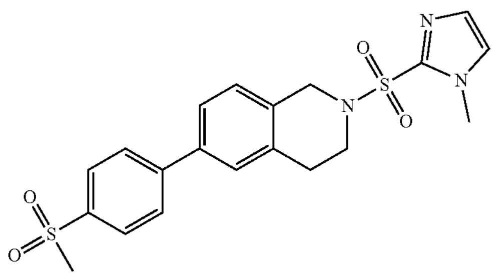 [SMILES: Cn1ccnc1S(=O)(=O)N1CCc2cc(-c3ccc(S(C)(=O)=O)cc3)ccc2C1] | 432.0 |
| 81 | 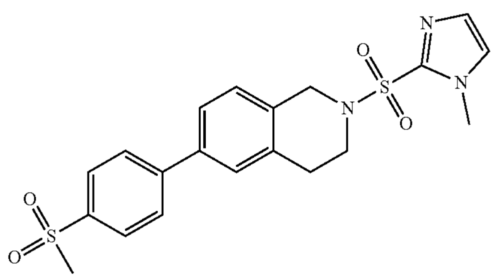 [SMILES: Cn1ccnc1S(=O)(=O)N1CCc2cc(-c3ccc(S(C)(=O)=O)cc3)ccc2C1] | 432.0 |
| 82 | 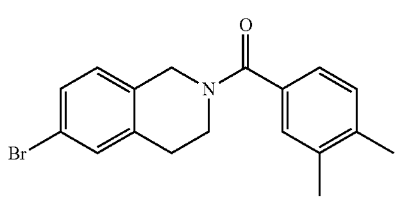 [SMILES: Cc1ccc(C(=O)N2CCc3cc(Br)ccc3C2)cc1C] | 344.0, 346.0 |
| 83 | 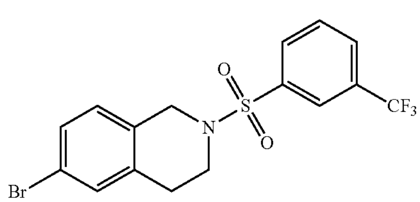 [SMILES: O=S(=O)(c1cccc(C(F)(F)F)c1)N1CCc2cc(Br)ccc2C1] | 419.9, 421.9 |

TABLE 2-continued
Additional Examples of Compounds according to formula I
| Example Number | Structure | MS (m/z): (M + H). |
|---|---|---|
| 84 | 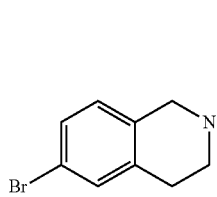 | 419.9, 421.9 |
| 85 | 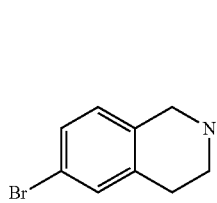 | 385.9, 387.9 |
| 86 | 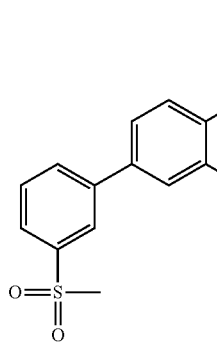 | 496.1 |
| 87 | 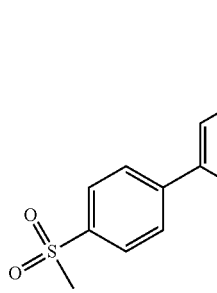 | 496.1 |
| 88 | 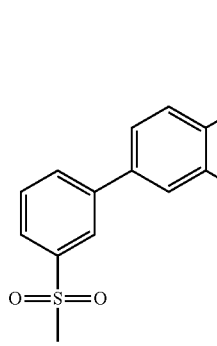 | 496.1 |

TABLE 2-continued
Additional Examples of Compounds according to formula I
| Example Number | Structure | MS (m/z): (M + H). |
|---|---|---|
| 89 | 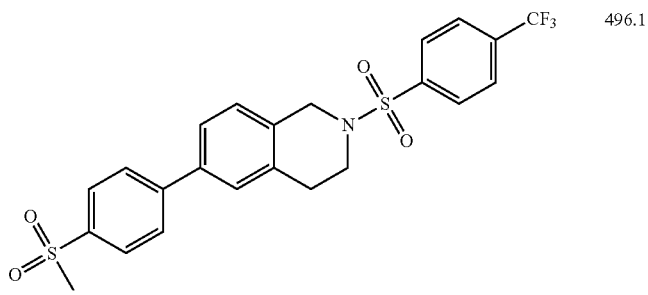 | 496.1 |
| 90 | 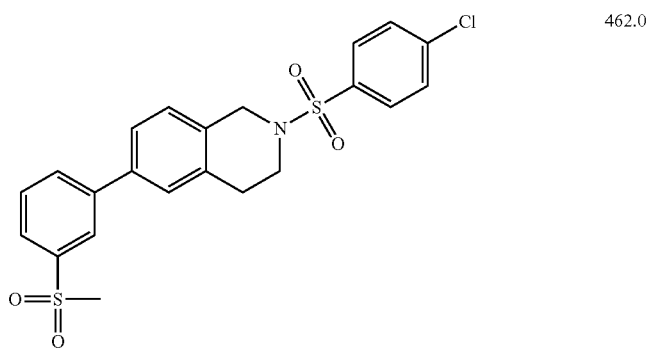 | 462.0 |
| 91 | 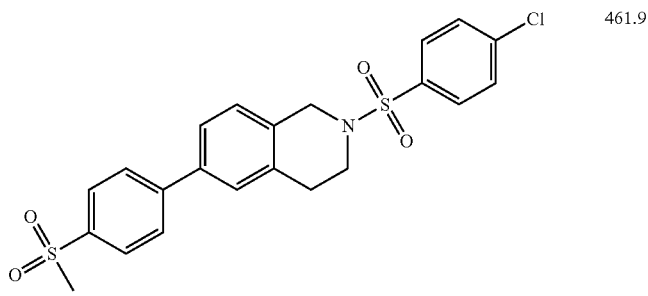 | 461.9 |
| 92 | 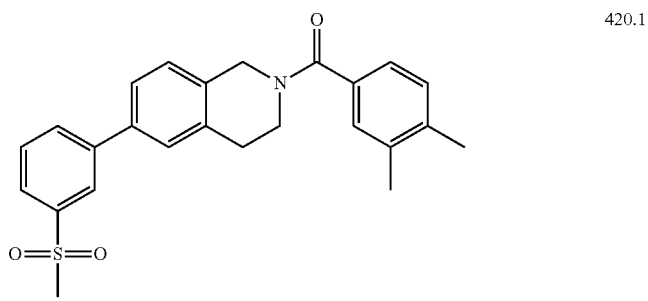 | 420.1 |
| 93 | 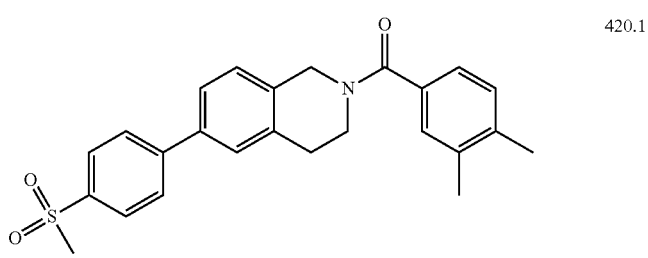 | 420.1 |

TABLE 2-continued
Additional Examples of Compounds according to formula I
| Example Number | Structure | MS (m/z): (M + H). |
|---|---|---|
| 94 | 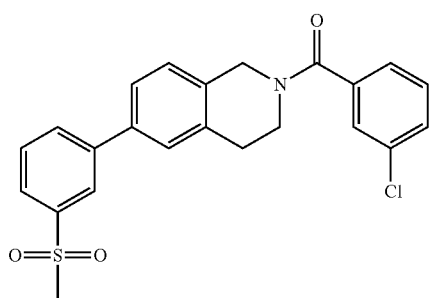 [SMILES: CS(=O)(=O)c1cccc(-c2ccc3c(c2)CCN(C(=O)c2cccc(Cl)c2)C3)c1] | 426.0 |
| 95 | 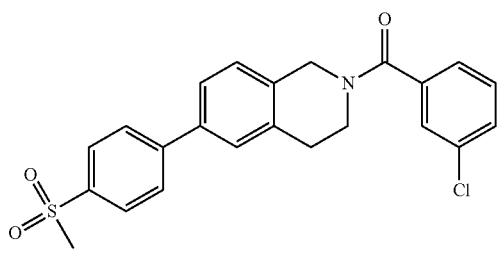 [SMILES: CS(=O)(=O)c1ccc(-c2ccc3c(c2)CCN(C(=O)c2cccc(Cl)c2)C3)cc1] | 426.0 |
| 96 | 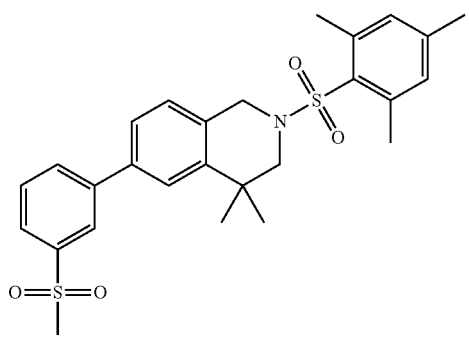 [SMILES: Cc1cc(C)c(S(=O)(=O)N2Cc3ccc(-c4cccc(S(C)(=O)=O)c4)cc3C(C)(C)C2)c(C)c1] | 498.1 |
| 97 | 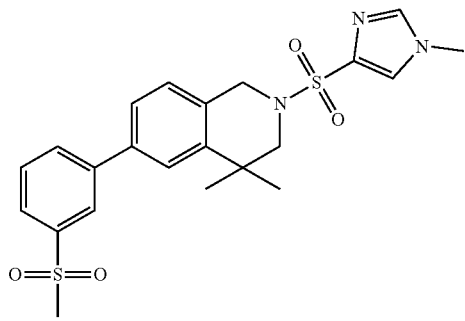 [SMILES: Cn1cnc(S(=O)(=O)N2Cc3ccc(-c4cccc(S(C)(=O)=O)c4)cc3C(C)(C)C2)c1] | 460.1 |

TABLE 2-continued

Additional Examples of Compounds according to formula I

| Example Number | Structure | MS (m/z): (M + H). |
|---|---|---|
| 98 | 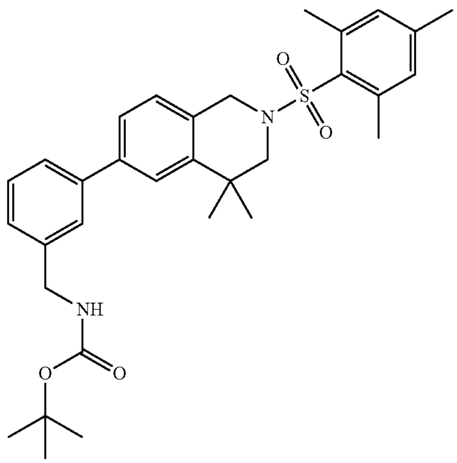 [SMILES: Cc1cc(C)c(S(=O)(=O)N2Cc3ccc(-c4cccc(CNC(=O)OC(C)(C)C)c4)cc3C(C)(C)C2)c(C)c1] | 549.3 |
| 99 | 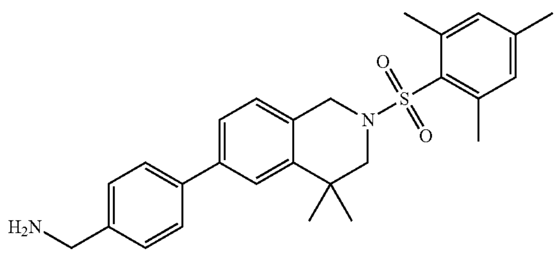 [SMILES: Cc1cc(C)c(S(=O)(=O)N2Cc3ccc(-c4ccc(CN)cc4)cc3C(C)(C)C2)c(C)c1] | 471.2 (M + Na⁺) |

TABLE 3

Additional Compounds of Formula II

| Example # | Structure | Obs m/z |
|---|---|---|
| 100 | 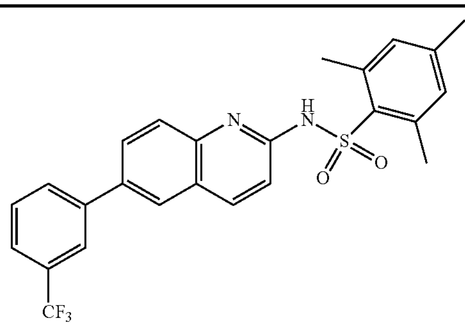 | 471.1 (M + H) |
| 101 | 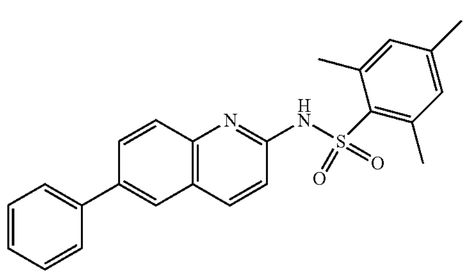 [SMILES: Cc1cc(C)c(S(=O)(=O)Nc2ccc3cc(-c4ccccc4)ccc3n2)c(C)c1] | 403.1 (M + H) |

TABLE 3-continued
Additional Compounds of Formula II
| Example # | Structure | Obs m/z |
|---|---|---|
| 102 | 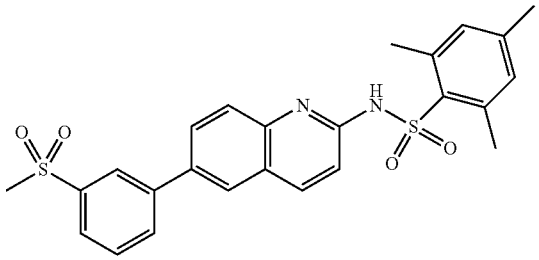 | 481.1 (M + H) |
| 103 | 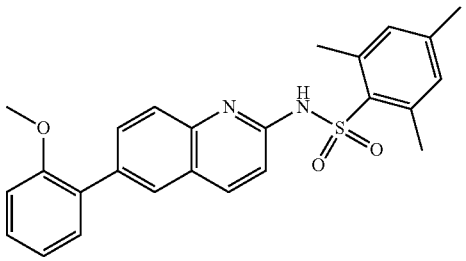 [SMILES: COc1ccccc1-c1ccc2nc(NS(=O)(=O)c3c(C)cc(C)cc3C)ccc2c1] | 433.1 (M + H) |
| 104 | 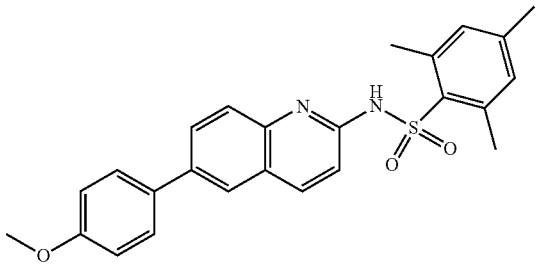 | 433.1 (M + H) |
| 105 | 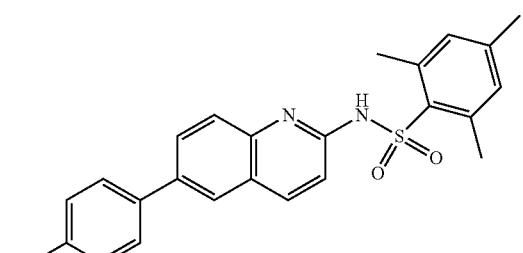 | 471.1 (M + H) |
| 106 | 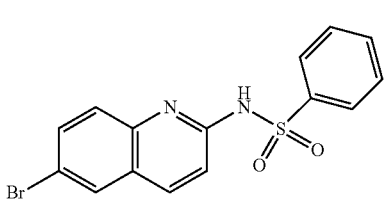 [SMILES: O=S(=O)(Nc1ccc2cc(Br)ccc2n1)c1ccccc1] | 362.9 364.0 (M + H) |
| 107 | 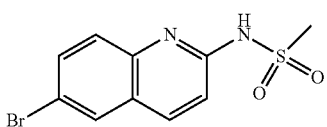 | 300.9, 302.9 (M + H) |

TABLE 3-continued

Additional Compounds of Formula II

| Example # | Structure | Obs m/z |
|---|---|---|
| 108 | 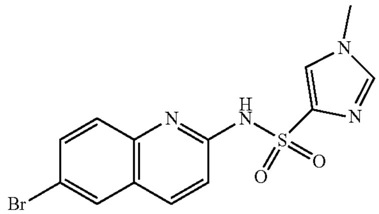 [SMILES: Cn1cnc(S(=O)(=O)Nc2ccc3cc(Br)ccc3n2)c1] | 366.9, 368.0 (M + H) |
| 109 | 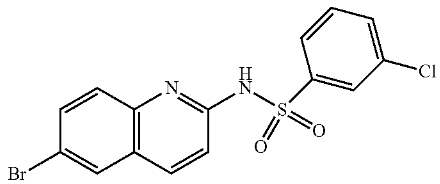 [SMILES: O=S(=O)(Nc1ccc2cc(Br)ccc2n1)c1cccc(Cl)c1] | 396.9, 398.0 (M + H) |
| 110 | 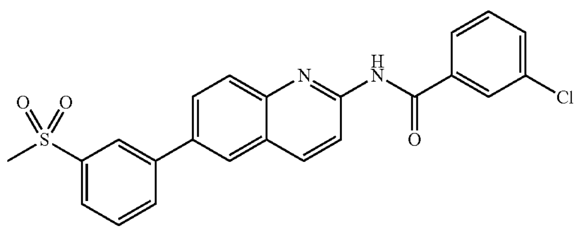 [SMILES: CS(=O)(=O)c1cccc(-c2ccc3nc(NC(=O)c4cccc(Cl)c4)ccc3c2)c1] | 437.1 (M + H) |
| 111 | 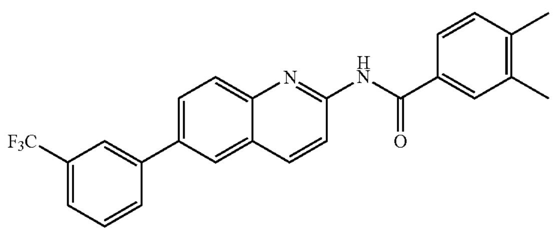 [SMILES: Cc1ccc(C(=O)Nc2ccc3cc(-c4cccc(C(F)(F)F)c4)ccc3n2)cc1C] | 421.1 (M + H) |
| 112 | 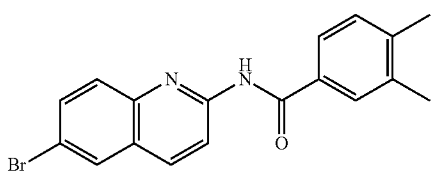 [SMILES: Cc1ccc(C(=O)Nc2ccc3cc(Br)ccc3n2)cc1C] | 357.0, 358.0 (M + H) |
| 113 | 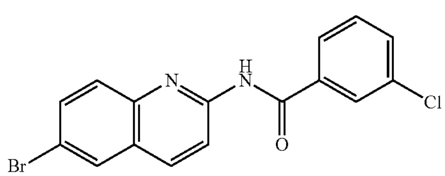 [SMILES: O=C(Nc1ccc2cc(Br)ccc2n1)c1cccc(Cl)c1] | 360.9, 362.9 (M + H) |
| 114 | 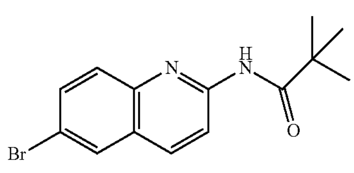 [SMILES: CC(C)(C)C(=O)Nc1ccc2cc(Br)ccc2n1] | 307.1, 309.0 (M + H) |

TABLE 3-continued
Additional Compounds of Formula II
| Example # | Structure | Obs m/z |
|---|---|---|
| 115 | 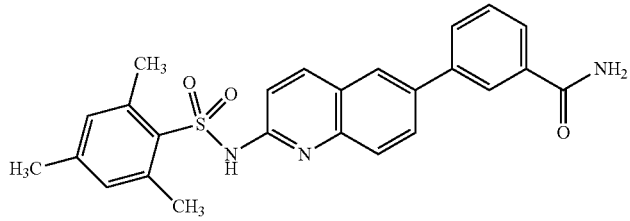 [SMILES: Cc1cc(C)c(S(=O)(=O)Nc2ccc3cc(-c4cccc(C(N)=O)c4)ccc3n2)c(C)c1] | 446.1 |
| 116 | 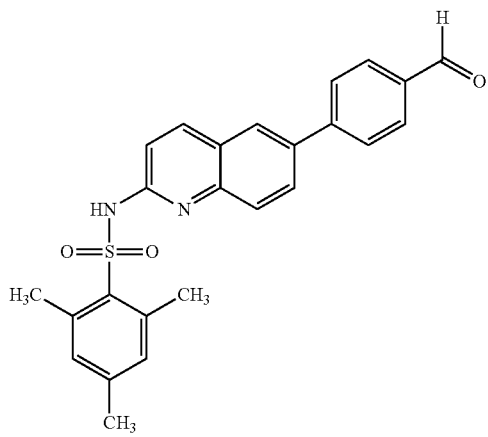 [SMILES: Cc1cc(C)c(S(=O)(=O)Nc2ccc3cc(-c4ccc(C=O)cc4)ccc3n2)c(C)c1] | 431.1 |
| 117 | 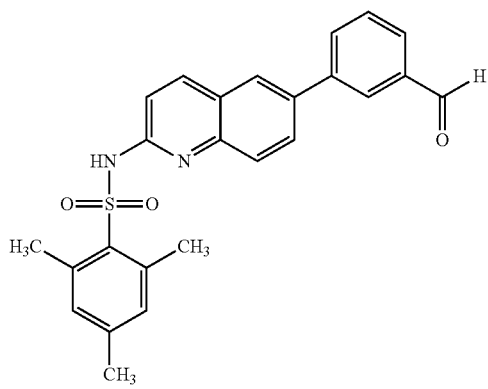 [SMILES: Cc1cc(C)c(S(=O)(=O)Nc2ccc3cc(-c4cccc(C=O)c4)ccc3n2)c(C)c1] | 431.1 |
| 118 | 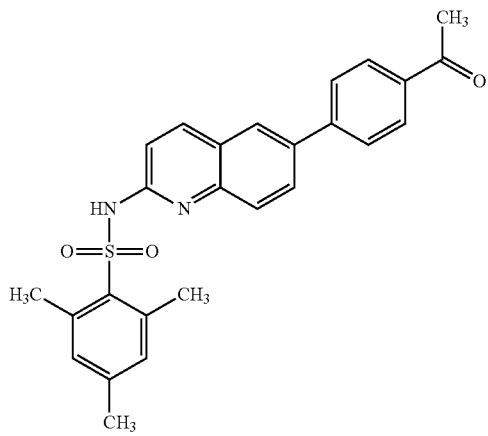 | 445.1 |

TABLE 3-continued

Additional Compounds of Formula II

| Example # | Structure | Obs m/z |
|---|---|---|
| 119 | 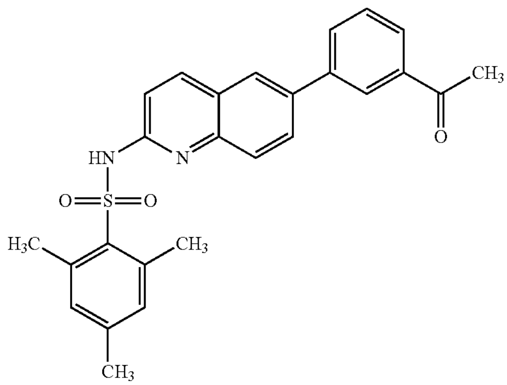 [SMILES: CC(=O)c1cccc(-c2ccc3nc(NS(=O)(=O)c4c(C)cc(C)cc4C)ccc3c2)c1] | 445.1 |
| 120 | 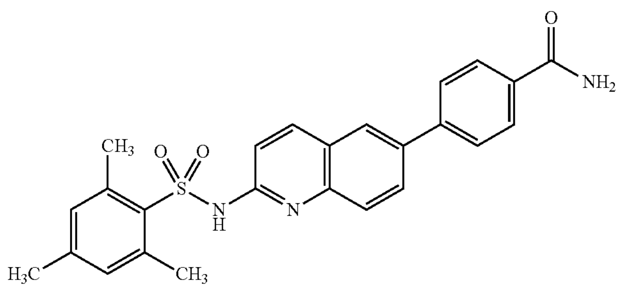 [SMILES: Cc1cc(C)c(S(=O)(=O)Nc2ccc3cc(-c4ccc(C(N)=O)cc4)ccc3n2)c(C)c1] | 446.1 |
| 121 | 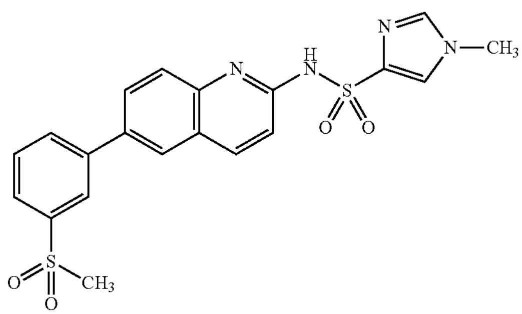 [SMILES: Cn1cnc(S(=O)(=O)Nc2ccc3cc(-c4cccc(S(C)(=O)=O)c4)ccc3n2)c1] | 443.0 |
| 122 | 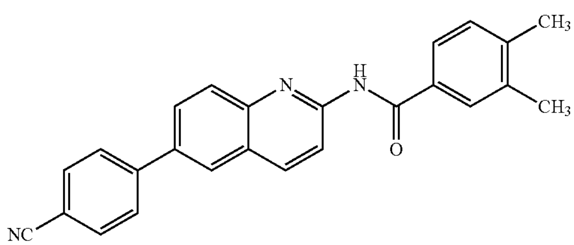 [SMILES: Cc1ccc(C(=O)Nc2ccc3cc(-c4ccc(C#N)cc4)ccc3n2)cc1C] | 378.1 |
| 123 | 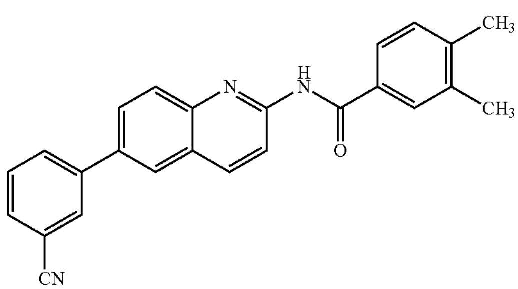 [SMILES: Cc1ccc(C(=O)Nc2ccc3cc(-c4cccc(C#N)c4)ccc3n2)cc1C] | 378.1 |

TABLE 3-continued

Additional Compounds of Formula II

| Example # | Structure | Obs m/z |
|---|---|---|
| 124 | 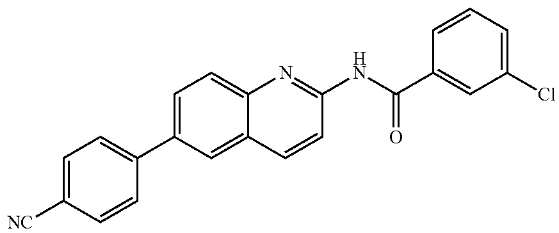 [SMILES: N#Cc1ccc(-c2ccc3nc(NC(=O)c4cccc(Cl)c4)ccc3c2)cc1] | 384.1 |
| 125 | 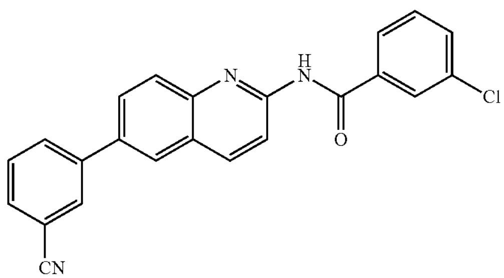 [SMILES: N#Cc1cccc(-c2ccc3nc(NC(=O)c4cccc(Cl)c4)ccc3c2)c1] | 384.1 |
| 126 | 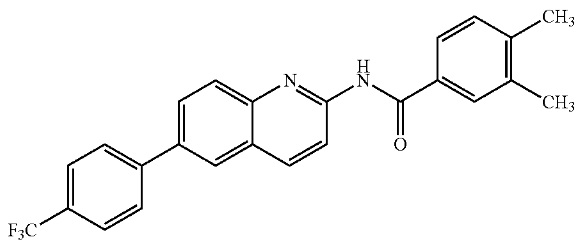 [SMILES: Cc1ccc(C(=O)Nc2ccc3cc(-c4ccc(C(F)(F)F)cc4)ccc3n2)cc1C] | 421.1 |
| 127 | 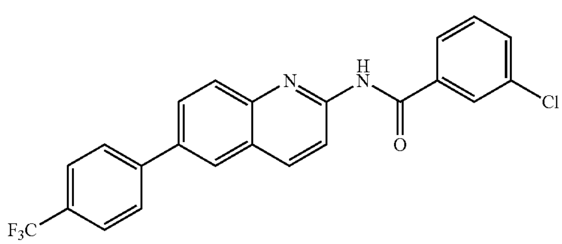 [SMILES: O=C(Nc1ccc2cc(-c3ccc(C(F)(F)F)cc3)ccc2n1)c1cccc(Cl)c1] | 427.0 |
| 128 | 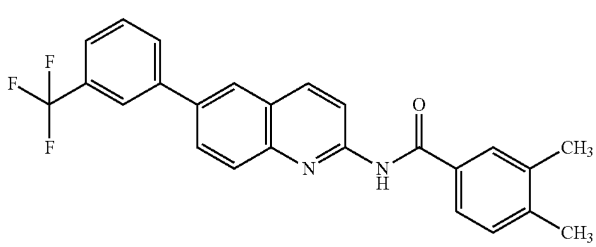 [SMILES: Cc1ccc(C(=O)Nc2ccc3cc(-c4cccc(C(F)(F)F)c4)ccc3n2)cc1C] | 421.1 |
| 129 | 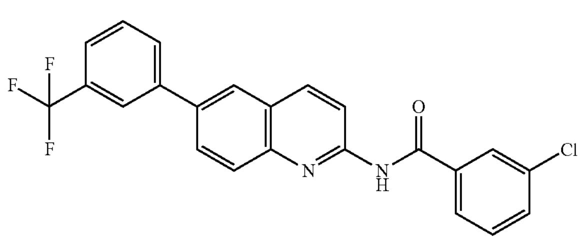 [SMILES: O=C(Nc1ccc2cc(-c3cccc(C(F)(F)F)c3)ccc2n1)c1cccc(Cl)c1] | 427.0 |

TABLE 3-continued

Additional Compounds of Formula II

| Example # | Structure | Obs m/z |
|---|---|---|
| 130 | 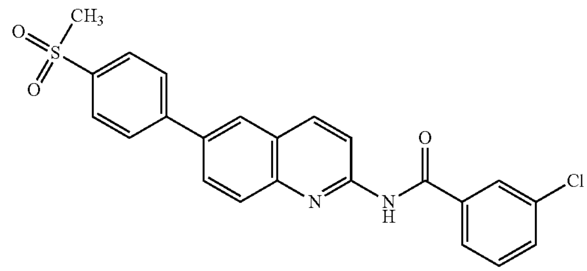 [SMILES: CS(=O)(=O)c1ccc(-c2ccc3nc(NC(=O)c4cccc(Cl)c4)ccc3c2)cc1] | 437.0 |
| 131 | 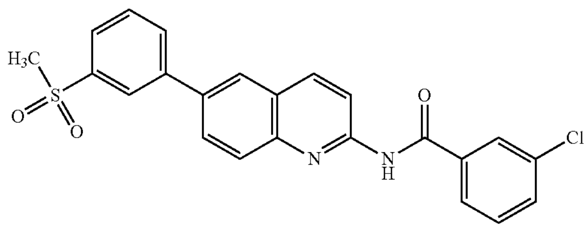 [SMILES: CS(=O)(=O)c1cccc(-c2ccc3nc(NC(=O)c4cccc(Cl)c4)ccc3c2)c1] | 437.0 |
| 132 | 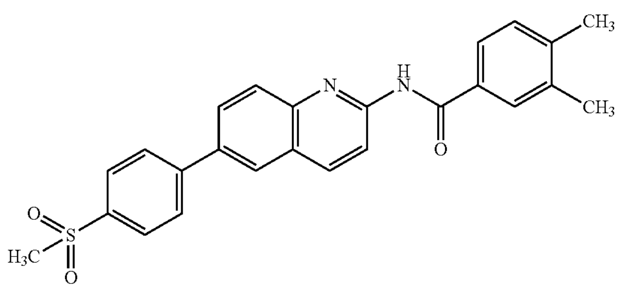 [SMILES: Cc1ccc(C(=O)Nc2ccc3cc(-c4ccc(S(C)(=O)=O)cc4)ccc3n2)cc1C] | 431.1 |
| 133 | 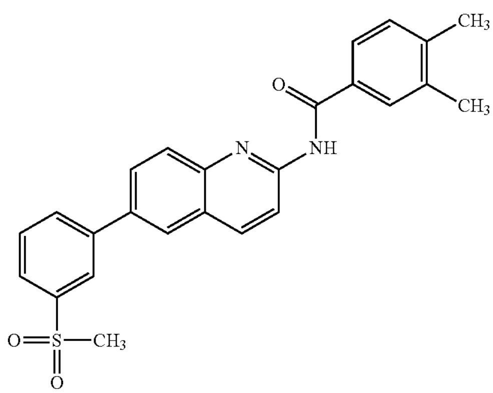 [SMILES: Cc1ccc(C(=O)Nc2ccc3cc(-c4cccc(S(C)(=O)=O)c4)ccc3n2)cc1C] | 431.1 |

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

IX. References

The following references, such that they provide exemplary procedural or other details supplementary to those set forth herein, are specifically incorporated by reference.

Anderson, *Practical Process Research & Development—A Guide for Organic Chemists*, $2^{nd}$ ed., Academic Press, New York, 2012.

Austin-Ward and Villaseca, *Rev. Med. Chil.*, 126(7):838-45, 1998.

Bukowski et al., *Clin. Cancer Res.*, 4(10):2337-47, 1998.
Christodoulides et al., *Microbiology*, 144(Pt 11):3027-37, 1998.
Davidson et al., *J. Immunother.*, 21(5):389-98, 1998.
*Handbook of Pharmaceutical Salts: Properties, and Use*, Stahl and Wermuth Eds., Verlag Helvetica Chimica Acta, 2002.
Hanibuchi et al., *Int. J. Cancer*, 78(4):480-485, 1998.
Hellstrand et al., *Acta Oncol.*, 37(4):347-353, 1998.
Hui and Hashimoto, *Infect. Immun.*, 66(11):5329-36, 1998.
Ju et al., *Gene Ther.*, 7(19):1672-1679, 2000.
Mitchell et al., *Ann. NY Acad Sci.*, 690:153-166, 1993.
Mitchell et al., *J. Clin. Oncol.*, 8(5):856-869, 1990.
Morton et al., *Arch. Surg.*, 127:392-399, 1992.
Pietras et al., *Oncogene*, 17(17):2235-49, 1998.
Qin et al., *Proc. Natl. Acad. Sci. USA*, 95(24):14411-14416, 1998.
Ravindranath and Morton, *Intern. Rev. Immunol.*, 7: 303-329, 1991.
Reagan-Shaw et al., *FASEB J.*, 22(3):659-661, 2008.
Rosenberg et al., *Ann. Surg.* 210(4):474-548, 1989.
Rosenberg et al., *N Engl. J. Med.*, 319:1676, 1988.
Smith, *March's Advanced Organic Chemistry: Reactions, Mechanisms, and Structure*, $7^{th}$ Ed., Wiley, 2013.
U.S. Pat. No. 5,739,169
U.S. Pat. No. 5,801,005
U.S. Pat. No. 5,824,311
U.S. Pat. No. 5,830,880
U.S. Pat. No. 5,846,945
Abdel-Magid et al. (1996). *J. Org. Chem.* 61(11): 3849-3862.
Beadle et al. (2014). WO2014/193781.
Hein et al. (2005). *J. Org. Chem.* 70: 9940-9946.
Horio et al., (1996). JP 08092268
House, H. O. (1972). *MODERN SYNTHETIC REACTIONS. SECOND EDITION*, W. A. Benzamin.
Kamenecka, T. M. and T. P. Burris (2015). WO2015/103527.
Mitsunobu, O. (1981). *Synthesis* 1: 1-28.
Wlochal, J. and A. Bailey (2015). *Tet. Lett.* 56: 6791-6794.

What is claimed is:

1. A compound of the formula:

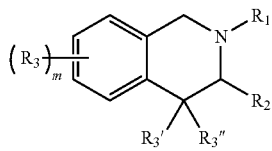

(I)

wherein:
R$_1$ is —C(O)R$_4$, —S(O)$_2$R$_4$, —S(O)R$_4$, or —CH$_2$R$_4$; wherein:
R$_4$ is aryl$_{(C \leq 12)}$, heteroaryl$_{(C \leq 12)}$, or a substituted version of either of these groups;
R$_2$ is —(CH$_2$)$_n$C(O)NR$_5$R$_6$; wherein:
R$_5$ and R$_6$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these five groups;
n is 0, 1, 2, or 3;
R$_3$ is aryl$_{(C \leq 12)}$, substituted aryl$_{(C \leq 12)}$, heteroaryl$_{(C \leq 12)}$, or substituted heteroaryl$_{(C \leq 12)}$;
R$_3$' and R$_3$" are each independently hydrogen, alkyl$_{(C \leq 8)}$, or substituted alkyl$_{(C \leq 8)}$; and
m is 1, 2, 3, or 4;
or a pharmaceutically acceptable salt thereof.

2. The compound of claim 1 further defined as:

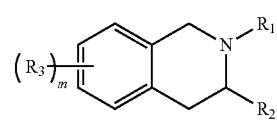

(III)

wherein:
R$_1$ is —C(O)R$_4$, —S(O)$_2$R$_4$, —S(O)R$_4$, or —CH$_2$R$_4$; wherein:
R$_4$ is aryl$_{(C \leq 12)}$, heteroaryl$_{(C \leq 12)}$, or a substituted version of either of these groups;
R$_2$ is —(CH$_2$)$_n$C(O)NR$_5$R$_6$; wherein:
R$_5$ and R$_6$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these five groups;
n is 0, 1, 2, or 3;
R$_3$ is aryl$_{(C \leq 12)}$, substituted aryl$_{(C \leq 12)}$, heteroaryl$_{(C \leq 12)}$, or substituted heteroaryl$_{(C \leq 12)}$; and
m is 1, 2, 3, or 4;
or a pharmaceutically acceptable salt thereof.

3. The compound of claim 1, further defined as:

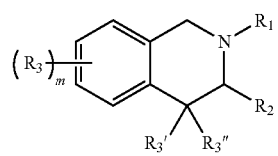

(I)

wherein:
R$_1$ is —C(O)R$_4$, —S(O)$_2$R$_4$, —S(O)R$_4$, or —CH$_2$R$_4$; wherein:
R$_4$ is aryl$_{(C \leq 12)}$, heteroaryl$_{(C \leq 12)}$, or a substituted version of either of these groups;
R$_2$ is —(CH$_2$)$_n$C(O)NR$_5$R$_6$; wherein:
R$_5$ and R$_6$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these five groups;
n is 0, 1, 2, or 3;
R$_3$ is aryl$_{(C \leq 12)}$, substituted aryl$_{(C \leq 12)}$, heteroaryl$_{(C \leq 12)}$, or substituted heteroaryl$_{(C \leq 12)}$;
R$_3$' and R$_3$" are each independently hydrogen, alkyl$_{(C \leq 8)}$, or substituted alkyl$_{(C \leq 8)}$; and
m is 1, 2, 3, or 4;
or a pharmaceutically acceptable salt thereof.

4. The compound of claim 3, further defined as:

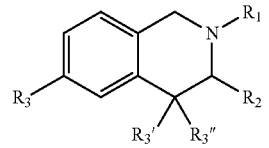

(IV)

wherein:

R$_1$ is —C(O)R$_4$, —S(O)$_2$R$_4$, —S(O)R$_4$, or —CH$_2$R$_4$; wherein:

R$_4$ is aryl$_{(C \leq 12)}$, heteroaryl$_{(C \leq 12)}$, or a substituted version of either of these groups;

R$_2$ is —(CH$_2$)$_n$C(O)NR$_5$R$_6$; wherein:

R$_5$ and R$_6$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these five groups; and n is 0, 1, 2, or 3;

R$_3$ is aryl$_{(C \leq 12)}$, substituted aryl$_{(C \leq 12)}$, heteroaryl$_{(C \leq 12)}$, or substituted heteroaryl$_{(C \leq 12)}$; and R$_3$' and R$_3$" are each independently hydrogen, alkyl$_{(C \leq 8)}$, or substituted alkyl$_{(C \leq 8)}$;

or a pharmaceutically acceptable salt thereof.

5. The compound according to claim 2, wherein R$_1$ is —S(O)$_2$R$_4$.

6. The compound according to claim 2, wherein R$_3$ is aryl$_{(C \leq 12)}$ or substituted aryl$_{(C \leq 12)}$.

7. The compound according to claim 2, wherein R$_3$ is heteroaryl$_{(C \leq 12)}$ or substituted heteroaryl$_{(C \leq 12)}$.

8. The compound according to claim 1, wherein R$_3$' is hydrogen.

9. The compound according to claim 1, wherein R$_3$' is alkyl$_{(C \leq 8)}$.

10. The compound according to claim 1, wherein R$_3$" is hydrogen.

11. The compound according to claim 1, wherein R$_3$" is alkyl$_{(C \leq 8)}$.

12. The compound according to claim 2, wherein R$_6$ is —C(O)R$_9$.

13. The compound according to claim 2, wherein R$_6$ is —S(O)$_2$R$_9$.

14. A pharmaceutical composition comprising:

(A) a compound of the formula:

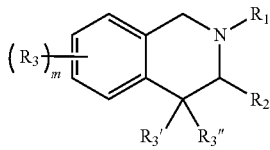

(I)

wherein:

R$_1$ is —C(O)R$_4$, —S(O)$_2$R$_4$, —S(O)R$_4$, or —CH$_2$R$_4$; wherein:

R$_4$ is aryl$_{(C \leq 12)}$, heteroaryl$_{(C \leq 12)}$, or a substituted version of either of these groups;

R$_2$ is —(CH$_2$)$_n$C(O)NR$_5$R$_6$; wherein:

R$_5$ and R$_6$ are each independently hydrogen or alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these five groups;

n is 0, 1, 2, or 3;

R$_3$ is aryl$_{(C \leq 12)}$, substituted aryl$_{(C \leq 12)}$, heteroaryl$_{(C \leq 12)}$, or substituted heteroaryl$_{(C \leq 12)}$;

R$_3$' and R$_3$" are each independently hydrogen, alkyl$_{(C \leq 8)}$, or substituted alkyl$_{(C \leq 8)}$; and m is 1, 2, 3, or 4;

or a pharmaceutically acceptable salt thereof;

and (B) an excipient, wherein the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

15. The pharmaceutical composition of claim 14, wherein the pharmaceutical composition is formulated for oral administration, intraarterial administration, intravenous administration, or intraperitoneal administration.

* * * * *

UNITED STATES PATENT AND TRADEMARK OFFICE
CERTIFICATE OF CORRECTION

| | | |
|---|---|---|
| PATENT NO. | : 11,746,097 B2 | Page 1 of 1 |
| APPLICATION NO. | : 16/311941 | |
| DATED | : September 5, 2023 | |
| INVENTOR(S) | : Burris et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 528 days.

Signed and Sealed this
Twelfth Day of November, 2024

Katherine Kelly Vidal
*Director of the United States Patent and Trademark Office*